United States Patent
Shelton, IV

(10) Patent No.: US 7,669,746 B2
(45) Date of Patent: *Mar. 2, 2010

(54) STAPLE CARTRIDGES FOR FORMING STAPLES HAVING DIFFERING FORMED STAPLE HEIGHTS

(75) Inventor: Frederick E. Shelton, IV, Hillsboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/216,562

(22) Filed: Aug. 31, 2005

(65) Prior Publication Data

US 2007/0045379 A1 Mar. 1, 2007

(51) Int. Cl.
*A61B 17/04* (2006.01)
(52) U.S. Cl. .................. 227/175.1; 227/19; 227/176.1; 227/178.1
(58) Field of Classification Search ............... 227/175.2, 227/176.1, 178.1, 180.1, 182.1, 19, 175.1, 227/179.1, 181.1; 606/48, 51
See application file for complete search history.

(56) References Cited

U.S. PATENT DOCUMENTS

| | | | |
|---|---|---|---|
| 2,037,727 A | 4/1936 | La Chapelle | |
| 2,853,074 A | 9/1958 | Olson | |
| 3,269,630 A | 8/1966 | Fleischer | |
| 3,490,675 A | 1/1970 | Green et al. | |
| 3,551,987 A | 1/1971 | Wilkinson | |
| 3,643,851 A | 2/1972 | Green et al. | |
| 3,662,939 A | 5/1972 | Bryan | |
| 3,717,294 A | 2/1973 | Green | |
| 3,734,207 A | 5/1973 | Fishbein | |
| 3,819,100 A | 6/1974 | Noiles et al. | |
| 3,894,174 A | 7/1975 | Cartun | |
| 3,940,844 A | 3/1976 | Colby et al. | |
| 4,317,451 A | 3/1982 | Cerwin et al. | |
| 4,321,002 A | 3/1982 | Froehlich | |
| 4,331,277 A | 5/1982 | Green | |
| 4,379,457 A | 4/1983 | Gravener et al. | |
| 4,380,312 A | 4/1983 | Landrus | |
| 4,383,634 A | 5/1983 | Green | |
| 4,396,139 A | 8/1983 | Hall et al. | |

(Continued)

FOREIGN PATENT DOCUMENTS

CA 2458946 A1 3/2003

(Continued)

OTHER PUBLICATIONS

U.S Appl. No. 11/712,315, filed Feb. 28, 2007.

(Continued)

*Primary Examiner*—Stephen Garbe
*Assistant Examiner*—Nathaniel Chukwurah

(57) ABSTRACT

A staple cartridge for use with a stapling device that has an actuator that is selectively actuatable in an axial direction and an anvil portion that is selectively movable between open and closed positions is disclosed. Various embodiments of the present invention include a cartridge body that movably supports first and second staple drivers. The staple drivers each support a staple thereon and serve to drive the staples into forming contact with the anvil upon actuation by the actuator. The various embodiments of the present invention enable the final formed heights of the staples to be varied without the need to use different sizes of staples.

23 Claims, 27 Drawing Sheets

U.S. PATENT DOCUMENTS

| | | |
|---|---|---|
| 4,402,445 A | 9/1983 | Green |
| 4,415,112 A | 11/1983 | Green |
| 4,428,376 A | 1/1984 | Mericle |
| 4,429,695 A | 2/1984 | Green |
| 4,442,964 A | 4/1984 | Becht |
| 4,475,679 A | 10/1984 | Fleury, Jr. |
| 4,485,816 A | 12/1984 | Krumme |
| 4,500,024 A | 2/1985 | DiGiovanni et al. |
| 4,505,273 A | 3/1985 | Braun et al. |
| 4,506,671 A | 3/1985 | Green |
| 4,520,817 A | 6/1985 | Green |
| 4,522,327 A | 6/1985 | Korthoff et al. |
| 4,526,174 A | 7/1985 | Froehlich |
| 4,530,453 A | 7/1985 | Green |
| 4,548,202 A | 10/1985 | Duncan |
| 4,566,620 A | 1/1986 | Green et al. |
| 4,573,622 A | 3/1986 | Green et al. |
| 4,580,712 A | 4/1986 | Green |
| 4,589,416 A | 5/1986 | Green |
| 4,605,001 A | 8/1986 | Rothfuss et al. |
| 4,606,343 A | 8/1986 | Conta et al. |
| 4,608,981 A | 9/1986 | Rothfuss et al. |
| 4,610,250 A | 9/1986 | Green |
| 4,610,383 A | 9/1986 | Rothfuss et al. |
| 4,619,262 A | 10/1986 | Taylor |
| 4,629,107 A | 12/1986 | Fedotov et al. |
| 4,633,874 A | 1/1987 | Chow et al. |
| 4,655,222 A | 4/1987 | Florez et al. |
| 4,664,305 A | 5/1987 | Blake, III et al. |
| 4,667,674 A | 5/1987 | Korthoff et al. |
| 4,671,445 A | 6/1987 | Barker et al. |
| 4,676,245 A | 6/1987 | Fukuda |
| 4,693,248 A | 9/1987 | Failla |
| 4,709,120 A | 11/1987 | Pearson |
| 4,715,520 A | 12/1987 | Roehr, Jr. et al. |
| 4,719,917 A | 1/1988 | Barrows et al. |
| 4,728,020 A | 3/1988 | Green et al. |
| 4,741,336 A | 5/1988 | Failla et al. |
| 4,754,909 A | 7/1988 | Barker et al. |
| 4,767,044 A | 8/1988 | Green |
| 4,805,617 A | 2/1989 | Bedi et al. |
| 4,805,823 A | 2/1989 | Rothfuss |
| 4,809,695 A | 3/1989 | Gwathmey et al. |
| 4,817,847 A | 4/1989 | Redtenbacher et al. |
| 4,821,939 A | 4/1989 | Green |
| 4,869,414 A | 9/1989 | Green et al. |
| 4,869,415 A | 9/1989 | Fox |
| 4,892,244 A | 1/1990 | Fox et al. |
| 4,915,100 A | 4/1990 | Green |
| 4,941,623 A * | 7/1990 | Pruitt ........................ 227/19 |
| 4,944,443 A | 7/1990 | Oddsen et al. |
| 4,955,959 A | 9/1990 | Tompkins et al. |
| 4,978,049 A * | 12/1990 | Green ..................... 227/178.1 |
| 5,009,661 A | 4/1991 | Michelson |
| 5,027,834 A | 7/1991 | Pruitt |
| 5,031,814 A | 7/1991 | Tompkins et al. |
| 5,040,715 A | 8/1991 | Green et al. |
| 5,062,563 A | 11/1991 | Green et al. |
| 5,065,929 A | 11/1991 | Schulze et al. |
| 5,071,430 A | 12/1991 | de Salis et al. |
| 5,080,556 A | 1/1992 | Carreno |
| 5,104,025 A | 4/1992 | Main et al. |
| 5,106,008 A | 4/1992 | Tompkins et al. |
| 5,111,987 A | 5/1992 | Moeinzadeh et al. |
| 5,116,349 A | 5/1992 | Aranyi |
| 5,129,570 A | 7/1992 | Schulze et al. |
| 5,137,198 A | 8/1992 | Nobis et al. |
| 5,139,513 A | 8/1992 | Segato |
| 5,156,315 A | 10/1992 | Green et al. |
| 5,158,567 A | 10/1992 | Green |
| 5,197,648 A | 3/1993 | Gingold |
| 5,200,280 A | 4/1993 | Karasa |
| 5,205,459 A | 4/1993 | Brinkerhoff et al. |
| 5,207,697 A | 5/1993 | Carusillo et al. |
| 5,211,649 A | 5/1993 | Kohler et al. |
| 5,219,111 A | 6/1993 | Bilotti et al. |
| 5,221,036 A | 6/1993 | Takase |
| 5,222,963 A | 6/1993 | Brinkerhoff et al. |
| 5,222,975 A | 6/1993 | Crainich |
| 5,222,976 A | 6/1993 | Yoon |
| 5,242,457 A | 9/1993 | Akopov et al. |
| 5,246,156 A | 9/1993 | Rothfuss et al. |
| 5,246,443 A | 9/1993 | Mai |
| 5,253,793 A | 10/1993 | Green et al. |
| 5,258,009 A | 11/1993 | Conners |
| 5,263,629 A | 11/1993 | Trumbull et al. |
| 5,263,973 A | 11/1993 | Cook |
| 5,271,544 A | 12/1993 | Fox et al. |
| RE34,519 E | 1/1994 | Fox et al. |
| 5,275,323 A | 1/1994 | Schulze et al. |
| 5,282,806 A | 2/1994 | Haber et al. |
| 5,282,829 A | 2/1994 | Hermes |
| 5,304,204 A | 4/1994 | Bregen |
| 5,307,976 A | 5/1994 | Olson et al. |
| 5,309,927 A | 5/1994 | Welch |
| 5,318,221 A | 6/1994 | Green et al. |
| 5,332,142 A | 7/1994 | Robinson et al. |
| 5,342,395 A | 8/1994 | Jarrett et al. |
| 5,342,396 A | 8/1994 | Cook |
| 5,344,060 A | 9/1994 | Gravener et al. |
| 5,350,400 A | 9/1994 | Esposito et al. |
| 5,352,238 A | 10/1994 | Green et al. |
| 5,358,510 A | 10/1994 | Luscombe et al. |
| 5,366,134 A | 11/1994 | Green et al. |
| 5,366,479 A | 11/1994 | McGarry et al. |
| 5,379,933 A | 1/1995 | Green et al. |
| 5,383,880 A | 1/1995 | Hooven |
| 5,389,098 A | 2/1995 | Tsuruta et al. |
| 5,392,979 A | 2/1995 | Green et al. |
| 5,395,030 A | 3/1995 | Kuramoto et al. |
| 5,395,033 A | 3/1995 | Byrne et al. |
| 5,397,046 A | 3/1995 | Savage et al. |
| 5,397,324 A | 3/1995 | Carroll et al. |
| 5,403,312 A | 4/1995 | Yates et al. |
| 5,411,508 A | 5/1995 | Bessler et al. |
| 5,413,267 A | 5/1995 | Solyntjes et al. |
| 5,413,268 A | 5/1995 | Green et al. |
| 5,415,334 A | 5/1995 | Williamson, IV et al. |
| 5,415,335 A | 5/1995 | Knodell, Jr. |
| 5,425,745 A | 6/1995 | Green et al. |
| 5,431,322 A | 7/1995 | Green et al. |
| 5,433,721 A | 7/1995 | Hooven et al. |
| 5,441,193 A | 8/1995 | Gravener |
| 5,445,304 A | 8/1995 | Plyley et al. |
| 5,445,644 A | 8/1995 | Pietrafitta et al. |
| 5,456,401 A | 10/1995 | Green et al. |
| 5,462,215 A | 10/1995 | Viola et al. |
| 5,465,895 A | 11/1995 | Knodel et al. |
| 5,465,896 A | 11/1995 | Allen et al. |
| 5,470,006 A | 11/1995 | Rodak |
| 5,472,132 A | 12/1995 | Savage et al. |
| 5,474,566 A | 12/1995 | Alesi et al. |
| 5,478,354 A | 12/1995 | Tovey et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,497,933 A | 3/1996 | DeFonzo et al. |
| 5,503,320 A | 4/1996 | Webster et al. |

| Patent | Date | Inventor | | Patent | Date | Inventor |
|---|---|---|---|---|---|---|
| 5,503,635 A | 4/1996 | Sauer et al. | | 5,678,748 A | 10/1997 | Plyley et al. |
| 5,503,638 A | 4/1996 | Cooper et al. | | 5,680,981 A | 10/1997 | Mililli et al. |
| 5,509,596 A | 4/1996 | Green et al. | | 5,680,982 A | 10/1997 | Schulze et al. |
| 5,518,163 A | 5/1996 | Hooven | | 5,680,983 A | 10/1997 | Plyley et al. |
| 5,518,164 A | 5/1996 | Hooven | | 5,685,474 A | 11/1997 | Seeber |
| 5,522,817 A | 6/1996 | Sander et al. | | 5,688,270 A | 11/1997 | Yates et al. |
| 5,529,235 A | 6/1996 | Boiarski et al. | | 5,690,269 A | 11/1997 | Bolanos et al. |
| 5,535,934 A | 7/1996 | Boiarski et al. | | 5,692,668 A | 12/1997 | Schulze et al. |
| 5,535,935 A | 7/1996 | Vidal et al. | | 5,693,042 A | 12/1997 | Boiarski et al. |
| 5,535,937 A | 7/1996 | Boiarski et al. | | 5,697,543 A | 12/1997 | Burdorff |
| 5,540,375 A | 7/1996 | Bolanos et al. | | 5,697,943 A | 12/1997 | Sauer et al. |
| 5,542,594 A | 8/1996 | McKean et al. | | 5,702,408 A | 12/1997 | Wales et al. |
| 5,547,117 A | 8/1996 | Hamblin et al. | | 5,704,534 A | 1/1998 | Huitema et al. |
| 5,549,628 A | 8/1996 | Cooper et al. | | 5,706,997 A | 1/1998 | Green et al. |
| 5,553,675 A | 9/1996 | Pitzen et al. | | 5,706,998 A | 1/1998 | Plyley et al. |
| 5,553,765 A | 9/1996 | Knodel et al. | | 5,709,680 A | 1/1998 | Yates et al. |
| 5,554,169 A | 9/1996 | Green et al. | | 5,711,472 A | 1/1998 | Bryan |
| 5,560,532 A | 10/1996 | DeFonzo et al. | | 5,713,505 A | 2/1998 | Huitema |
| 5,562,239 A | 10/1996 | Boiarski et al. | | 5,715,987 A | 2/1998 | Kelley et al. |
| 5,562,241 A | 10/1996 | Knodel et al. | | 5,715,988 A | 2/1998 | Palmer |
| 5,562,682 A | 10/1996 | Oberlin et al. | | 5,716,366 A | 2/1998 | Yates |
| 5,564,615 A | 10/1996 | Bishop et al. | | 5,718,359 A | 2/1998 | Palmer et al. |
| 5,571,090 A | 11/1996 | Sherts | | 5,725,536 A | 3/1998 | Oberlin et al. |
| 5,571,116 A | 11/1996 | Bolanos et al. | | 5,725,554 A | 3/1998 | Simon et al. |
| 5,573,543 A | 11/1996 | Akopov et al. | | 5,732,871 A | 3/1998 | Clark et al. |
| 5,574,431 A | 11/1996 | McKeown et al. | | 5,735,445 A | 4/1998 | Vidal et al. |
| 5,575,799 A | 11/1996 | Bolanos et al. | | 5,738,474 A | 4/1998 | Blewett |
| 5,575,803 A | 11/1996 | Cooper et al. | | 5,743,456 A | 4/1998 | Jones et al. |
| 5,577,654 A | 11/1996 | Bishop | | 5,747,953 A | 5/1998 | Philipp |
| 5,580,067 A | 12/1996 | Hamblin et al. | | 5,752,644 A | 5/1998 | Bolanos et al. |
| 5,582,611 A | 12/1996 | Tsuruta et al. | | 5,752,965 A | 5/1998 | Francis et al. |
| 5,584,425 A | 12/1996 | Savage et al. | | 5,758,814 A | 6/1998 | Gallagher et al. |
| 5,586,711 A * | 12/1996 | Plyley et al. ............. 227/176.1 | | 5,762,255 A | 6/1998 | Chrisman et al. |
| 5,588,579 A | 12/1996 | Schnut et al. | | 5,762,256 A | 6/1998 | Mastri et al. |
| 5,588,580 A | 12/1996 | Paul et al. | | 5,766,188 A | 6/1998 | Igaki |
| 5,588,581 A | 12/1996 | Conlon et al. | | 5,779,130 A | 7/1998 | Alesi et al. |
| 5,597,107 A | 1/1997 | Knodel et al. | | 5,779,132 A | 7/1998 | Knodel et al. |
| 5,601,224 A | 2/1997 | Bishop et al. | | 5,782,396 A | 7/1998 | Mastri et al. |
| 5,603,443 A | 2/1997 | Clark et al. | | 5,782,397 A | 7/1998 | Koukline |
| 5,605,272 A | 2/1997 | Witt et al. | | 5,785,232 A | 7/1998 | Vidal et al. |
| 5,605,273 A | 2/1997 | Hamblin et al. | | 5,794,834 A | 8/1998 | Hamblin et al. |
| 5,607,094 A | 3/1997 | Clark et al. | | 5,796,188 A | 8/1998 | Bays |
| 5,607,095 A | 3/1997 | Smith et al. | | 5,797,536 A | 8/1998 | Smith et al. |
| 5,609,285 A | 3/1997 | Grant et al. | | 5,797,537 A | 8/1998 | Oberlin et al. |
| 5,624,452 A | 4/1997 | Yates | | 5,797,538 A | 8/1998 | Heaton et al. |
| 5,628,446 A | 5/1997 | Geiste et al. | | 5,799,857 A | 9/1998 | Robertson et al. |
| 5,630,539 A | 5/1997 | Plyley et al. | | 5,807,393 A | 9/1998 | Williamson, IV et al. |
| 5,630,540 A | 5/1997 | Blewett | | 5,817,093 A | 10/1998 | Williamson, IV et al. |
| 5,632,432 A | 5/1997 | Schulze et al. | | 5,820,009 A | 10/1998 | Melling et al. |
| 5,632,433 A | 5/1997 | Grant et al. | | 5,823,066 A | 10/1998 | Huitema et al. |
| 5,634,584 A | 6/1997 | Okorocha et al. | | 5,826,776 A | 10/1998 | Schulze et al. |
| 5,636,779 A | 6/1997 | Palmer | | 5,829,662 A | 11/1998 | Allen et al. |
| 5,636,780 A | 6/1997 | Green et al. | | 5,833,690 A | 11/1998 | Yates et al. |
| 5,639,008 A | 6/1997 | Gallagher et al. | | 5,833,695 A | 11/1998 | Yoon |
| 5,645,209 A | 7/1997 | Green et al. | | 5,836,503 A | 11/1998 | Ehrenfels et al. |
| 5,647,526 A | 7/1997 | Green et al. | | 5,839,639 A | 11/1998 | Sauer et al. |
| 5,649,937 A | 7/1997 | Bito et al. | | 5,843,132 A | 12/1998 | Ilvento |
| 5,651,491 A | 7/1997 | Heaton et al. | | 5,846,254 A | 12/1998 | Schulze et al. |
| 5,653,373 A | 8/1997 | Green et al. | | 5,855,311 A | 1/1999 | Hamblin et al. |
| 5,653,374 A | 8/1997 | Young et al. | | 5,865,361 A | 2/1999 | Milliman et al. |
| 5,653,721 A | 8/1997 | Knodel et al. | | 5,868,760 A | 2/1999 | McGuckin, Jr. |
| 5,655,698 A | 8/1997 | Yoon | | 5,871,135 A * | 2/1999 | Williamson, IV et al. 227/178.1 |
| 5,657,921 A | 8/1997 | Young et al. | | 5,878,937 A | 3/1999 | Green et al. |
| 5,658,300 A | 8/1997 | Bito et al. | | 5,878,938 A | 3/1999 | Bittner et al. |
| 5,662,258 A | 9/1997 | Knodel et al. | | 5,891,160 A | 4/1999 | Williamson, IV et al. |
| 5,662,260 A | 9/1997 | Yoon | | 5,893,506 A | 4/1999 | Powell |
| 5,662,662 A | 9/1997 | Bishop et al. | | 5,894,979 A | 4/1999 | Powell |
| 5,667,517 A | 9/1997 | Hooven | | 5,897,562 A | 4/1999 | Bolanos et al. |
| 5,667,527 A | 9/1997 | Cook | | 5,901,895 A | 5/1999 | Heaton et al. |
| 5,669,544 A | 9/1997 | Schulze et al. | | 5,902,312 A | 5/1999 | Frater et al. |
| 5,673,840 A | 10/1997 | Schulze et al. | | 5,906,625 A | 5/1999 | Bito et al. |
| 5,673,841 A | 10/1997 | Schulze et al. | | 5,911,353 A | 6/1999 | Bolanos et al. |
| 5,673,842 A | 10/1997 | Bittner et al. | | 5,915,616 A | 6/1999 | Viola et al. |

| | | | |
|---|---|---|---|
| 5,918,791 A | 7/1999 | Sorrentino et al. | |
| 5,919,198 A | 7/1999 | Graves, Jr. et al. | |
| 5,941,442 A | 8/1999 | Geiste et al. | |
| 5,954,259 A | 9/1999 | Viola et al. | |
| 5,988,479 A | 11/1999 | Palmer | |
| 6,010,054 A | 1/2000 | Johnson et al. | |
| 6,017,356 A | 1/2000 | Frederick et al. | |
| 6,022,352 A | 2/2000 | Vandewalle | |
| 6,024,741 A | 2/2000 | Williamson, IV et al. | |
| 6,024,748 A | 2/2000 | Manzo et al. | |
| 6,032,849 A | 3/2000 | Mastri et al. | |
| 6,045,560 A | 4/2000 | McKean et al. | |
| 6,050,472 A | 4/2000 | Shibata | |
| 6,079,606 A | 6/2000 | Milliman et al. | |
| 6,083,234 A | 7/2000 | Nicholas et al. | |
| 6,083,242 A | 7/2000 | Cook | |
| 6,086,600 A | 7/2000 | Kortenbach | |
| 6,099,537 A | 8/2000 | Sugai et al. | |
| 6,102,271 A | 8/2000 | Longo et al. | |
| 6,109,500 A | 8/2000 | Alli et al. | |
| 6,119,913 A | 9/2000 | Adams et al. | |
| H1904 H | 10/2000 | Yates et al. | |
| 6,126,058 A | 10/2000 | Adams et al. | |
| 6,126,670 A | 10/2000 | Walker et al. | |
| 6,131,789 A | 10/2000 | Schulze et al. | |
| 6,155,473 A | 12/2000 | Tompkins et al. | |
| 6,156,056 A | 12/2000 | Kearns et al. | |
| 6,171,316 B1 | 1/2001 | Kovac et al. | |
| 6,171,330 B1 | 1/2001 | Benchetrit | |
| 6,202,914 B1 | 3/2001 | Geiste et al. | |
| 6,223,835 B1 | 5/2001 | Habedank et al. | |
| 6,241,139 B1 | 6/2001 | Milliman et al. | |
| 6,250,532 B1 | 6/2001 | Green et al. | |
| 6,258,107 B1 | 7/2001 | Balázs et al. | |
| 6,264,086 B1 | 7/2001 | McGuckin, Jr. | |
| 6,264,087 B1 | 7/2001 | Whitman | |
| 6,273,897 B1 | 8/2001 | Dalessandro et al. | |
| 6,302,311 B1 | 10/2001 | Adams et al. | |
| 6,315,184 B1 | 11/2001 | Whitman | |
| 6,320,123 B1 | 11/2001 | Reimers | |
| 6,325,810 B1 | 12/2001 | Hamilton et al. | |
| 6,330,965 B1 | 12/2001 | Milliman et al. | |
| 6,358,224 B1 | 3/2002 | Tims et al. | |
| 6,387,113 B1 | 5/2002 | Hawkins et al. | |
| 6,387,114 B2 | 5/2002 | Adams | |
| 6,398,797 B2 | 6/2002 | Bombard et al. | |
| 6,416,486 B1 | 7/2002 | Wampler | |
| RE37,814 E | 8/2002 | Allgeyer | |
| 6,436,107 B1 | 8/2002 | Wang et al. | |
| 6,440,146 B2 | 8/2002 | Nicholas et al. | |
| 6,443,973 B1 | 9/2002 | Whitman | |
| 6,488,197 B1 | 12/2002 | Whitman | |
| 6,491,201 B1 | 12/2002 | Whitman | |
| 6,503,257 B2 | 1/2003 | Grant et al. | |
| 6,503,259 B2 | 1/2003 | Huxel et al. | |
| 6,505,768 B2 | 1/2003 | Whitman | |
| 6,511,468 B1 | 1/2003 | Cragg et al. | |
| 6,517,565 B1 | 2/2003 | Whitman et al. | |
| 6,522,101 B2 | 2/2003 | Malackowski | |
| 6,551,333 B2 | 4/2003 | Kuhns et al. | |
| 6,578,751 B2 | 6/2003 | Hartwick | |
| 6,592,597 B2 | 7/2003 | Grant et al. | |
| 6,601,749 B2 | 8/2003 | Sullivan et al. | |
| 6,602,252 B2 | 8/2003 | Mollenauer | |
| 6,616,686 B2 | 9/2003 | Coleman et al. | |
| 6,619,529 B2 | 9/2003 | Green et al. | |
| 6,620,166 B1 | 9/2003 | Wenstrom, Jr. et al. | |
| 6,629,988 B2 | 10/2003 | Weadock | |
| 6,644,532 B2 | 11/2003 | Green et al. | |
| 6,656,193 B2 | 12/2003 | Grant et al. | |
| 6,669,073 B2 | 12/2003 | Milliman et al. | |
| 6,681,978 B2 | 1/2004 | Geiste et al. | |
| 6,681,979 B2 | 1/2004 | Whitman | |
| 6,682,528 B2 | 1/2004 | Frazier et al. | |
| 6,695,199 B2 | 2/2004 | Whitman | |
| 6,698,643 B2 | 3/2004 | Whitman | |
| 6,704,210 B1 | 3/2004 | Myers | |
| 6,716,223 B2 | 4/2004 | Leopold et al. | |
| 6,716,233 B1 | 4/2004 | Whitman | |
| 6,747,121 B2 | 6/2004 | Gogolewski | |
| 6,755,338 B2 | 6/2004 | Hahnen et al. | |
| 6,767,356 B2 | 7/2004 | Kanner et al. | |
| 6,773,438 B1 | 8/2004 | Knodel et al. | |
| 6,786,382 B1 * | 9/2004 | Hoffman | 227/178.1 |
| 6,793,652 B1 | 9/2004 | Whitman et al. | |
| 6,805,273 B2 | 10/2004 | Bilotti et al. | |
| 6,806,808 B1 | 10/2004 | Watters et al. | |
| 6,814,741 B2 | 11/2004 | Bowman et al. | |
| 6,817,508 B1 | 11/2004 | Racenet et al. | |
| 6,817,509 B2 | 11/2004 | Geiste et al. | |
| 6,821,273 B2 | 11/2004 | Mollenauer | |
| 6,828,902 B2 | 12/2004 | Casden | |
| 6,830,174 B2 | 12/2004 | Hillstead et al. | |
| 6,835,199 B2 | 12/2004 | McGuckin, Jr. et al. | |
| 6,843,403 B2 | 1/2005 | Whitman | |
| 6,846,307 B2 | 1/2005 | Whitman et al. | |
| 6,846,308 B2 | 1/2005 | Whitman et al. | |
| 6,846,309 B2 | 1/2005 | Whitman et al. | |
| 6,849,071 B2 | 2/2005 | Whitman et al. | |
| RE38,708 E | 3/2005 | Bolanos et al. | |
| 6,872,214 B2 | 3/2005 | Sonnenschein et al. | |
| 6,877,647 B2 | 4/2005 | Green et al. | |
| 6,905,057 B2 | 6/2005 | Swayze et al. | |
| 6,913,608 B2 | 7/2005 | Liddicoat et al. | |
| 6,939,358 B2 | 9/2005 | Palacios et al. | |
| 6,945,444 B2 | 9/2005 | Gresham et al. | |
| 6,953,138 B1 | 10/2005 | Dworak et al. | |
| 6,953,139 B2 | 10/2005 | Milliman et al. | |
| 6,959,852 B2 | 11/2005 | Shelton, IV et al. | |
| 6,960,220 B2 | 11/2005 | Marino et al. | |
| 6,964,363 B2 | 11/2005 | Wales et al. | |
| 6,974,462 B2 | 12/2005 | Sater | |
| 6,978,921 B2 * | 12/2005 | Shelton et al. | 227/176.1 |
| 6,978,922 B2 | 12/2005 | Bilotti et al. | |
| 6,981,628 B2 | 1/2006 | Wales | |
| 6,981,941 B2 | 1/2006 | Whitman et al. | |
| 6,986,451 B1 | 1/2006 | Mastri et al. | |
| 6,988,649 B2 * | 1/2006 | Shelton et al. | 227/175.2 |
| 6,988,650 B2 | 1/2006 | Schwemberger et al. | |
| 7,000,818 B2 * | 2/2006 | Shelton et al. | 227/176.1 |
| 7,000,819 B2 | 2/2006 | Swayze et al. | |
| 7,008,435 B2 | 3/2006 | Cummins | |
| 7,032,798 B2 | 4/2006 | Whitman et al. | |
| 7,032,799 B2 | 4/2006 | Viola et al. | |
| 7,044,352 B2 | 5/2006 | Shelton, IV et al. | |
| 7,044,353 B2 | 5/2006 | Mastri et al. | |
| 7,048,687 B1 | 5/2006 | Reuss et al. | |
| 7,055,730 B2 | 6/2006 | Ehrenfels et al. | |
| 7,055,731 B2 | 6/2006 | Shelton, IV et al. | |
| 7,056,330 B2 | 6/2006 | Gayton | |
| 7,059,508 B2 | 6/2006 | Shelton, IV et al. | |
| 7,063,712 B2 | 6/2006 | Vargas et al. | |
| 7,066,944 B2 | 6/2006 | Laufer et al. | |
| 7,070,083 B2 | 7/2006 | Jankowski | |
| 7,077,856 B2 | 7/2006 | Whitman | |
| 7,083,075 B2 | 8/2006 | Swayze et al. | |
| 7,090,673 B2 | 8/2006 | Dycus et al. | |
| 7,090,684 B2 | 8/2006 | McGuckin, Jr. et al. | |
| 7,097,089 B2 | 8/2006 | Marczyk | |
| 7,098,794 B2 | 8/2006 | Lindsay et al. | |
| 7,108,701 B2 | 9/2006 | Evens et al. | |
| 7,108,709 B2 | 9/2006 | Cummins | |
| 7,111,769 B2 | 9/2006 | Wales et al. | |
| 7,112,214 B2 | 9/2006 | Peterson et al. | |
| 7,114,642 B2 | 10/2006 | Whitman | |
| 7,118,582 B1 | 10/2006 | Wang et al. | |

| Patent No. | Date | Inventor(s) |
|---|---|---|
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,160,299 B2 | 1/2007 | Bally |
| 7,168,604 B2 | 1/2007 | Milliman et al. |
| 7,188,758 B2 | 3/2007 | Viola et al. |
| 7,207,471 B2 | 4/2007 | Heinrich et al. |
| 7,207,472 B2 | 4/2007 | Wukusick et al. |
| 7,210,609 B2 | 5/2007 | Leiboff et al. |
| 7,220,272 B2 | 5/2007 | Weadock |
| 7,225,964 B2 | 6/2007 | Mastri et al. |
| 7,235,302 B2 | 6/2007 | Jing et al. |
| 7,246,734 B2 | 7/2007 | Shelton, IV |
| 7,258,262 B2 | 8/2007 | Mastri et al. |
| 7,278,563 B1 | 10/2007 | Green |
| 7,296,724 B2 | 11/2007 | Green et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,328,829 B2 | 2/2008 | Arad et al. |
| 7,377,928 B2 | 5/2008 | Zubik et al. |
| 7,404,508 B2 | 7/2008 | Smith et al. |
| 7,404,509 B2 | 7/2008 | Ortiz et al. |
| 7,422,136 B1 | 9/2008 | Marczyk |
| 7,424,965 B2 | 9/2008 | Racenet et al. |
| 7,431,188 B1 | 10/2008 | Marczyk |
| 7,434,715 B2 | 10/2008 | Shelton, IV et al. |
| 7,434,717 B2 | 10/2008 | Shelton, IV et al. |
| 7,438,209 B1 | 10/2008 | Hess et al. |
| 7,441,685 B1 | 10/2008 | Boudreaux |
| 7,464,847 B2 | 12/2008 | Viola et al. |
| 7,490,749 B2 | 2/2009 | Schall et al. |
| 7,494,039 B2 | 2/2009 | Racenet et al. |
| 7,506,790 B2 | 3/2009 | Shelton, IV |
| 2002/0117534 A1 | 8/2002 | Green et al. |
| 2002/0165541 A1 | 11/2002 | Whitman |
| 2003/0105478 A1 | 6/2003 | Whitman et al. |
| 2003/0130677 A1 | 7/2003 | Whitman et al. |
| 2003/0216778 A1 | 11/2003 | Weadock |
| 2003/0220660 A1 | 11/2003 | Kortenbach et al. |
| 2004/0002726 A1 | 1/2004 | Nunez et al. |
| 2004/0006372 A1 | 1/2004 | Racenet et al. |
| 2004/0028502 A1 | 2/2004 | Cummins |
| 2004/0034357 A1 | 2/2004 | Beane et al. |
| 2004/0034369 A1 | 2/2004 | Sauer et al. |
| 2004/0044364 A1 | 3/2004 | DeVries et al. |
| 2004/0094597 A1 | 5/2004 | Whitman et al. |
| 2004/0097987 A1 | 5/2004 | Pugsley et al. |
| 2004/0101822 A1 | 5/2004 | Weisner et al. |
| 2004/0108357 A1 | 6/2004 | Milliman et al. |
| 2004/0111081 A1 | 6/2004 | Whitman et al. |
| 2004/0122471 A1 | 6/2004 | Toby et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0222268 A1 | 11/2004 | Bilotti et al. |
| 2004/0232196 A1 | 11/2004 | Shelton, IV et al. |
| 2004/0232199 A1* | 11/2004 | Shelton et al. ............ 227/175.2 |
| 2004/0232201 A1 | 11/2004 | Wenchell et al. |
| 2004/0243151 A1 | 12/2004 | Demmy et al. |
| 2004/0243176 A1 | 12/2004 | Hahnen et al. |
| 2004/0254608 A1 | 12/2004 | Huitema et al. |
| 2005/0006434 A1 | 1/2005 | Wales et al. |
| 2005/0021026 A1 | 1/2005 | Baily |
| 2005/0023324 A1 | 2/2005 | Doll et al. |
| 2005/0059997 A1 | 3/2005 | Bauman et al. |
| 2005/0070929 A1 | 3/2005 | Dalessandro et al. |
| 2005/0070958 A1 | 3/2005 | Swayze et al. |
| 2005/0072827 A1 | 4/2005 | Mollenauer |
| 2005/0080454 A1 | 4/2005 | Drews et al. |
| 2005/0103819 A1 | 5/2005 | Racenet et al. |
| 2005/0107824 A1 | 5/2005 | Hillstead et al. |
| 2005/0119669 A1 | 6/2005 | Demmy |
| 2005/0125009 A1 | 6/2005 | Perry et al. |
| 2005/0131390 A1 | 6/2005 | Heinrich et al. |
| 2005/0143759 A1 | 6/2005 | Kelly |
| 2005/0145671 A1 | 7/2005 | Viola |
| 2005/0165415 A1 | 7/2005 | Wales |
| 2005/0169974 A1 | 8/2005 | Tenerz et al. |
| 2005/0173490 A1 | 8/2005 | Shelton, IV |
| 2005/0184121 A1 | 8/2005 | Heinrich |
| 2005/0187576 A1* | 8/2005 | Whitman et al. ............ 606/219 |
| 2005/0189397 A1 | 9/2005 | Jankowski |
| 2005/0203550 A1 | 9/2005 | Laufer et al. |
| 2005/0216055 A1 | 9/2005 | Scirica et al. |
| 2005/0230453 A1 | 10/2005 | Viola |
| 2005/0245965 A1 | 11/2005 | Orban, III et al. |
| 2005/0263562 A1 | 12/2005 | Shelton, IV et al. |
| 2005/0263563 A1 | 12/2005 | Racenet et al. |
| 2005/0274768 A1 | 12/2005 | Cummins et al. |
| 2006/0011699 A1* | 1/2006 | Olson et al. ............ 227/180.1 |
| 2006/0025812 A1 | 2/2006 | Shelton, IV |
| 2006/0025813 A1 | 2/2006 | Shelton et al. |
| 2006/0025816 A1 | 2/2006 | Shelton |
| 2006/0047307 A1 | 3/2006 | Ortiz et al. |
| 2006/0047308 A1 | 3/2006 | Ortiz et al. |
| 2006/0049229 A1 | 3/2006 | Milliman et al. |
| 2006/0052825 A1 | 3/2006 | Ransick et al. |
| 2006/0060630 A1 | 3/2006 | Shelton, IV et al. |
| 2006/0085033 A1 | 4/2006 | Criscuolo et al. |
| 2006/0087442 A1 | 4/2006 | Smith et al. |
| 2006/0100643 A1 | 5/2006 | Laufer et al. |
| 2006/0108393 A1 | 5/2006 | Heinrich et al. |
| 2006/0122636 A1 | 6/2006 | Bailly et al. |
| 2006/0142772 A1 | 6/2006 | Ralph et al. |
| 2006/0151567 A1 | 7/2006 | Roy |
| 2006/0173470 A1 | 8/2006 | Oray et al. |
| 2006/0180634 A1 | 8/2006 | Shelton, IV et al. |
| 2006/0183246 A1 | 8/2006 | Wiesner et al. |
| 2006/0190028 A1 | 8/2006 | Wales et al. |
| 2006/0226196 A1 | 10/2006 | Hueil et al. |
| 2006/0245971 A1 | 11/2006 | Burns et al. |
| 2006/0273135 A1 | 12/2006 | Beetel |
| 2006/0278680 A1 | 12/2006 | Viola et al. |
| 2006/0278681 A1 | 12/2006 | Viola et al. |
| 2006/0289602 A1 | 12/2006 | Wales et al. |
| 2006/0291981 A1 | 12/2006 | Viola et al. |
| 2007/0023477 A1 | 2/2007 | Whitman et al. |
| 2007/0034666 A1* | 2/2007 | Holsten et al. ............ 227/176.1 |
| 2007/0034668 A1 | 2/2007 | Holsten et al. |
| 2007/0073340 A1 | 3/2007 | Shelton, IV et al. |
| 2007/0075114 A1 | 4/2007 | Shelton, IV et al. |
| 2007/0083234 A1 | 4/2007 | Shelton, IV et al. |
| 2007/0084897 A1 | 4/2007 | Shelton, IV et al. |
| 2007/0102452 A1 | 5/2007 | Shelton, IV et al. |
| 2007/0102453 A1 | 5/2007 | Morgan et al. |
| 2007/0102472 A1 | 5/2007 | Shelton, IV |
| 2007/0102473 A1 | 5/2007 | Shelton, IV et al. |
| 2007/0102474 A1 | 5/2007 | Shelton, IV et al. |
| 2007/0102475 A1 | 5/2007 | Ortiz et al. |
| 2007/0102476 A1 | 5/2007 | Shelton, IV et al. |
| 2007/0106317 A1 | 5/2007 | Shelton, IV et al. |
| 2007/0114261 A1 | 5/2007 | Ortiz et al. |
| 2007/0131732 A1* | 6/2007 | Holsten et al. ............ 227/179.1 |
| 2007/0158385 A1 | 7/2007 | Hueil et al. |
| 2007/0170225 A1 | 7/2007 | Shelton, IV et al. |
| 2007/0175949 A1 | 8/2007 | Shelton, IV et al. |
| 2007/0175950 A1 | 8/2007 | Shelton, IV et al. |

| Publication No. | Date | Inventor |
|---|---|---|
| 2007/0175951 A1 | 8/2007 | Shelton, IV et al. |
| 2007/0175952 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0175956 A1 | 8/2007 | Swayze et al. |
| 2007/0175957 A1 | 8/2007 | Shelton, IV et al. |
| 2007/0175958 A1 | 8/2007 | Shelton, IV et al. |
| 2007/0175959 A1 | 8/2007 | Shelton, IV et al. |
| 2007/0175960 A1 | 8/2007 | Shelton, IV et al. |
| 2007/0175961 A1 | 8/2007 | Shelton, IV et al. |
| 2007/0175962 A1 | 8/2007 | Shelton, IV et al. |
| 2007/0175964 A1 | 8/2007 | Shelton, IV et al. |
| 2007/0179476 A1 | 8/2007 | Shelton, IV et al. |
| 2007/0181632 A1 | 8/2007 | Milliman |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0194082 A1 | 8/2007 | Morgan et al. |
| 2007/0213750 A1 | 9/2007 | Weadock |
| 2007/0233053 A1 | 10/2007 | Shelton, IV et al. |
| 2007/0262116 A1 | 11/2007 | Hueil et al. |
| 2007/0295780 A1 | 12/2007 | Shelton et al. |
| 2008/0015598 A1 | 1/2008 | Prommersberger |
| 2008/0029570 A1 | 2/2008 | Shelton et al. |
| 2008/0029571 A1 | 2/2008 | Shelton et al. |
| 2008/0029572 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0029577 A1 | 2/2008 | Shelton et al. |
| 2008/0035701 A1 | 2/2008 | Racenet et al. |
| 2008/0041917 A1 | 2/2008 | Racenet et al. |
| 2008/0078800 A1 | 4/2008 | Hess et al. |
| 2008/0078801 A1 | 4/2008 | Shelton et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078805 A1 | 4/2008 | Omaits et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082115 A1 | 4/2008 | Morgan et al. |
| 2008/0082124 A1 | 4/2008 | Hess et al. |
| 2008/0082125 A1 | 4/2008 | Murray et al. |
| 2008/0082126 A1 | 4/2008 | Murray et al. |
| 2008/0083813 A1 | 4/2008 | Zemlok et al. |
| 2008/0164296 A1 | 7/2008 | Shelton et al. |
| 2008/0167522 A1 | 7/2008 | Giordano et al. |
| 2008/0167644 A1 | 7/2008 | Shelton et al. |
| 2008/0167670 A1 | 7/2008 | Shelton et al. |
| 2008/0167671 A1 | 7/2008 | Giordano et al. |
| 2008/0167672 A1 | 7/2008 | Giordano et al. |
| 2008/0167736 A1 | 7/2008 | Swayze et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0210738 A1 | 9/2008 | Shelton et al. |
| 2008/0237296 A1 | 10/2008 | Boudreaux et al. |
| 2008/0237298 A1 | 10/2008 | Schall et al. |
| 2008/0296343 A1 | 12/2008 | Schall et al. |
| 2008/0296345 A1 | 12/2008 | Shelton, IV et al. |
| 2008/0296346 A1 | 12/2008 | Shelton, IV et al. |
| 2008/0296347 A1 | 12/2008 | Shelton, IV et al. |
| 2008/0300579 A1 | 12/2008 | Broehl et al. |
| 2008/0300580 A1 | 12/2008 | Shelton, IV et al. |
| 2008/0300613 A1 | 12/2008 | Shelton, IV et al. |
| 2008/0308601 A1 | 12/2008 | Timm et al. |
| 2008/0308602 A1 | 12/2008 | Timm et al. |
| 2008/0308603 A1 | 12/2008 | Shelton, IV et al. |
| 2008/0308604 A1 | 12/2008 | Timm et al. |
| 2008/0308606 A1 | 12/2008 | Timm et al. |
| 2008/0308607 A1 | 12/2008 | Timm et al. |
| 2008/0314954 A1 | 12/2008 | Boudreaux |
| 2008/0314955 A1 | 12/2008 | Boudreaux et al. |
| 2008/0314956 A1 | 12/2008 | Boudreaux |
| 2008/0314957 A1 | 12/2008 | Boudreaux |
| 2008/0314961 A1 | 12/2008 | Boudreaux et al. |
| 2008/0314962 A1 | 12/2008 | Boudreaux |
| 2009/0001121 A1 | 1/2009 | Hess et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012556 A1 | 1/2009 | Boudreaux et al. |
| 2009/0076534 A1 | 3/2009 | Shelton, IV et al. |
| 2009/0200355 A1 | 8/2009 | Baxter, III et al. |
| 2009/0206123 A1 | 8/2009 | Doll et al. |
| 2009/0206124 A1 | 8/2009 | Hall et al. |
| 2009/0206125 A1 | 8/2009 | Huitema et al. |
| 2009/0206126 A1 | 8/2009 | Huitema et al. |
| 2009/0206128 A1 | 8/2009 | Hueil et al. |
| 2009/0206129 A1 | 8/2009 | Doll et al. |
| 2009/0206130 A1 | 8/2009 | Hall et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206134 A1 | 8/2009 | Swayze et al. |
| 2009/0206135 A1 | 8/2009 | Hall et al. |
| 2009/0206136 A1 | 8/2009 | Moore et al. |
| 2009/0206137 A1 | 8/2009 | Hall et al. |
| 2009/0206138 A1 | 8/2009 | Smith et al. |
| 2009/0206139 A1 | 8/2009 | Hall et al. |
| 2009/0206140 A1 | 8/2009 | Scheib et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0206144 A1 | 8/2009 | Doll et al. |
| 2009/0209946 A1 | 8/2009 | Swayze et al. |

FOREIGN PATENT DOCUMENTS

| | | |
|---|---|---|
| CA | 2512960 A1 | 1/2006 |
| CA | 2514274 A1 | 1/2006 |
| DE | 273689 C | 5/1914 |
| DE | 1775926 A | 1/1972 |
| DE | 9412228 U | 9/1994 |
| DE | 19924311 A1 | 11/2000 |
| DE | 69328576 T2 | 1/2001 |
| DE | 20111837 U1 | 10/2001 |
| DE | 20121753 U1 | 4/2003 |
| DE | 10314072 A1 | 10/2004 |
| EP | 0122046 A1 | 10/1984 |
| EP | 0033548 B1 | 5/1986 |
| EP | 0276104 A2 | 7/1988 |
| EP | 0593920 A1 | 4/1994 |
| EP | 0600182 A2 | 6/1994 |
| EP | 0630612 A1 | 12/1994 |
| EP | 0634144 A1 | 1/1995 |
| EP | 0646356 A2 | 4/1995 |
| EP | 0646357 A1 | 4/1995 |
| EP | 0669104 A1 | 8/1995 |
| EP | 0392547 B1 | 12/1995 |
| EP | 0685204 A1 | 12/1995 |
| EP | 0699418 A1 | 3/1996 |
| EP | 0702937 A1 | 3/1996 |
| EP | 0705571 A1 | 4/1996 |
| EP | 0484677 B2 | 6/1996 |

| | | | | | | |
|---|---|---|---|---|---|---|
| EP | 0541987 B1 | 7/1996 | | WO | WO 96/35464 A1 | 11/1996 |
| EP | 0770355 A1 | 5/1997 | | WO | WO 97/34533 A1 | 9/1997 |
| EP | 0503662 B1 | 6/1997 | | WO | WO 98/30153 A1 | 7/1998 |
| EP | 0625335 B1 | 11/1997 | | WO | WO 99/12483 A1 | 3/1999 |
| EP | 0552423 B1 | 1/1998 | | WO | WO 99/15086 A1 | 4/1999 |
| EP | 0592244 B1 | 1/1998 | | WO | WO 99/34744 A1 | 7/1999 |
| EP | 0648476 B1 | 1/1998 | | WO | WO 99/45849 A1 | 9/1999 |
| EP | 0603472 B1 | 11/1998 | | WO | WO 00/24322 A1 | 5/2000 |
| EP | 0605351 B1 | 11/1998 | | WO | WO 00/57796 A1 | 10/2000 |
| EP | 0878169 A1 | 11/1998 | | WO | WO 00/64365 A1 | 11/2000 |
| EP | 0879742 A1 | 11/1998 | | WO | WO 00/72762 A1 | 12/2000 |
| EP | 0537572 B1 | 6/1999 | | WO | WO 00/72765 A1 | 12/2000 |
| EP | 0552050 B1 | 5/2000 | | WO | WO 01/05702 A1 | 1/2001 |
| EP | 1090592 A1 * | 4/2001 | | WO | WO 01/10482 A1 | 2/2001 |
| EP | 0908152 B1 | 1/2002 | | WO | WO 01/54594 A1 | 8/2001 |
| EP | 0872213 B1 | 5/2002 | | WO | WO 01/62158 A2 | 8/2001 |
| EP | 1238634 A2 | 9/2002 | | WO | WO 01/62162 A1 | 8/2001 |
| EP | 0656188 B1 | 1/2003 | | WO | WO 01/62164 A2 | 8/2001 |
| EP | 0829235 B1 | 6/2003 | | WO | WO 01/91646 A1 | 12/2001 |
| EP | 0813843 B1 | 10/2003 | | WO | WO 02/07618 A1 | 1/2002 |
| EP | 0741996 B1 | 2/2004 | | WO | WO 02/17799 A1 | 3/2002 |
| EP | 0705570 B1 | 4/2004 | | WO | WO 02/19920 A1 | 3/2002 |
| EP | 1086713 B1 | 5/2004 | | WO | WO 02/30297 A2 | 4/2002 |
| EP | 1426012 A1 | 6/2004 | | WO | WO 02/32322 A2 | 4/2002 |
| EP | 0888749 B1 | 9/2004 | | WO | WO 02/43571 A2 | 6/2002 |
| EP | 1477119 A1 | 11/2004 | | WO | WO 02/058568 A1 | 8/2002 |
| EP | 1479345 A1 | 11/2004 | | WO | WO 02/067785 A2 | 9/2002 |
| EP | 1479347 A1 | 11/2004 | | WO | WO 02/098302 A1 | 12/2002 |
| EP | 1479348 A1 | 11/2004 | | WO | WO 03/000138 A2 | 1/2003 |
| EP | 1520521 A1 | 4/2005 | | WO | WO 03/001329 A1 | 1/2003 |
| EP | 1520523 A1 | 4/2005 | | WO | WO 03/013363 A1 | 2/2003 |
| EP | 1522264 A1 | 4/2005 | | WO | WO 03/020106 A2 | 3/2003 |
| EP | 1557129 A1 | 7/2005 | | WO | WO 03/079909 A3 | 3/2003 |
| EP | 1157666 B1 | 9/2005 | | WO | WO 03/030743 A2 | 4/2003 |
| EP | 1621138 A2 | 2/2006 | | WO | WO 03/037193 A1 | 5/2003 |
| EP | 1621145 A2 | 2/2006 | | WO | WO 03/047436 A3 | 6/2003 |
| EP | 1652481 A2 | 5/2006 | | WO | WO 03/057048 A1 | 7/2003 |
| EP | 1382303 B1 | 6/2006 | | WO | WO 03/057058 A1 | 7/2003 |
| EP | 1702567 A2 | 9/2006 | | WO | WO 03/063694 A1 | 8/2003 |
| EP | 1728473 A1 | 12/2006 | | WO | WO 03/077769 A1 | 9/2003 |
| EP | 1728475 A2 | 12/2006 | | WO | WO 03/082126 A1 | 10/2003 |
| EP | 1484024 B1 | 1/2007 | | WO | WO 03/088845 A2 | 10/2003 |
| EP | 1754445 A2 | 2/2007 | | WO | WO 03/090630 A2 | 11/2003 |
| EP | 1759812 A1 | 3/2007 | | WO | WO 03/094743 A1 | 11/2003 |
| EP | 1300117 B1 | 8/2007 | | WO | WO 03/094745 A1 | 11/2003 |
| EP | 1813199 A1 | 8/2007 | | WO | WO 03/094746 A1 | 11/2003 |
| EP | 1813207 A1 | 8/2007 | | WO | WO 2003/094747 A1 | 11/2003 |
| EP | 1872727 A1 | 1/2008 | | WO | WO 03/101313 A1 | 12/2003 |
| EP | 1839596 A2 | 2/2008 | | WO | WO 03/105698 A2 | 12/2003 |
| EP | 1897502 A1 | 3/2008 | | WO | WO 03/105702 A2 | 12/2003 |
| EP | 1749486 B1 | 3/2009 | | WO | WO 2004/006980 A2 | 1/2004 |
| FR | 999646 A | 2/1952 | | WO | WO 2004/028585 A2 | 4/2004 |
| FR | 1112936 A | 3/1956 | | WO | WO 2004/032754 A2 | 4/2004 |
| FR | 2765794 A | 1/1999 | | WO | WO 2004/032760 A2 | 4/2004 |
| GB | 939929 A | 10/1963 | | WO | WO 2004/032762 A1 | 4/2004 |
| GB | 2336214 A | 10/1999 | | WO | WO 2004/032763 A2 | 4/2004 |
| JP | 6007357 A | 1/1994 | | WO | WO 2004/047653 A2 | 6/2004 |
| JP | 8033641 A | 2/1996 | | WO | WO 2004/049956 A2 | 6/2004 |
| JP | 8229050 A | 9/1996 | | WO | WO 2004/086987 A1 | 10/2004 |
| JP | 2000287987 A | 10/2000 | | WO | WO 2004/096057 A2 | 11/2004 |
| JP | 2001286477 A | 10/2001 | | WO | WO 2004/112618 A2 | 12/2004 |
| JP | 2002369820 A | 12/2002 | | WO | WO 2004/112652 A2 | 12/2004 |
| JP | 2005505322 | 2/2005 | | WO | WO 2005/027983 A2 | 3/2005 |
| JP | 2005103293 A | 4/2005 | | WO | WO 2005/037329 A2 | 4/2005 |
| RU | 2187249 C2 | 8/2002 | | WO | WO 2005/096954 A2 | 10/2005 |
| RU | 2225170 C2 | 3/2004 | | WO | WO 2005/112808 A1 | 12/2005 |
| SU | 1377053 A1 | 2/1988 | | WO | WO 2005/115251 A2 | 12/2005 |
| SU | 1561964 A1 | 5/1990 | | WO | WO 2006/044490 A2 | 4/2006 |
| SU | 1722476 A1 | 3/1992 | | WO | WO 2006/044581 A2 | 4/2006 |
| WO | WO 93/08755 A1 | 5/1993 | | WO | WO 2006/044810 A2 | 4/2006 |
| WO | WO 95/18572 A1 | 7/1995 | | WO | WO 2006/083748 A1 | 8/2006 |
| WO | WO 95/23557 A1 | 9/1995 | | WO | WO 2006/132992 A1 | 12/2006 |
| WO | WO 95/29639 A1 | 11/1995 | | WO | WO 2007/016290 A2 | 2/2007 |

| | | |
|---|---|---|
| WO | WO 2007/121579 A1 | 11/2007 |
| WO | WO 2007/142625 A2 | 12/2007 |
| WO | WO 2008/045383 A2 | 4/2008 |

OTHER PUBLICATIONS

U.S Appl. No. 11/541,151, filed Sep. 29, 2006.
Disclosed Anonymously, "Motor-Driven Surgical Stapler Improvements," Research Disclosure Database No. 526041, Published: Feb. 2008.
U.S. Appl. No. 11/824,251, filed Jun. 29, 2007.
U.S. Appl. No. 12/038,939, filed Feb. 28, 2008.
U.S. Appl. No. 11/652,165, filed Jan. 11, 2007.
U.S. Appl. No. 11/824,446, filed Jun. 29, 2007.
U.S. Appl. No. 11/824,389, filed Jun. 29, 2007.
U.S. Appl. No. 11/824,415, filed Jun. 29, 2007.
U.S. Appl. No. 11/824,274, filed Jun. 29, 2007.
U.S. Appl. No. 11/824,275, filed Jun. 29, 2007.
U.S. Appl. No. 11/823,988, filed Jun. 29, 2007.
U.S. Appl. No. 11/824,079, filed Jun. 29, 2007.
U.S. Appl. No. 11/824,524, filed Jun. 29, 2007.
U.S. Appl. No. 11/824,298, filed Jun. 29, 2007.
U.S. Appl. No. 11/824,252, filed Jun. 29, 2007.

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000. 7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
Partial European Search Report, Application No. 08250661.9, dated May 7, 2009 (6 pages).
European Search Report, Application No. 08250667.6, dated May 14, 2009 (6 pages).
Partial European Search Report, Application No. 08250664.3, dated May 7, 2009 (6 pages).
Examination Report for European Patent Application No. 08250671.8, dated Mar. 24, 2009 (6 pages).
European Search Report, Application No. 08250668.4, dated May 4, 2009 (7 pages).

* cited by examiner

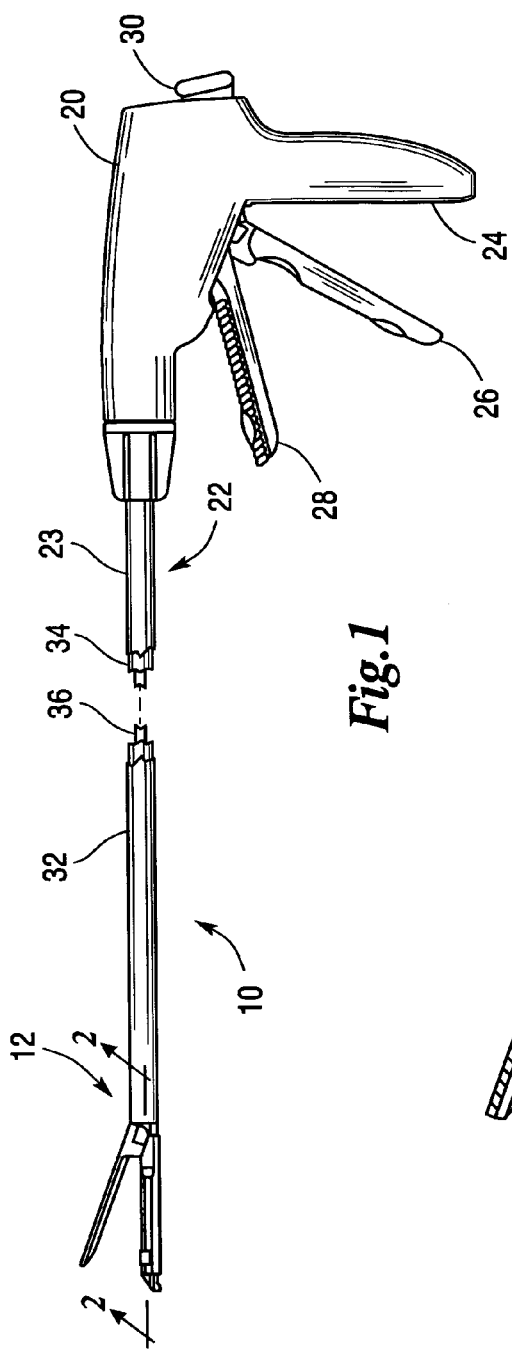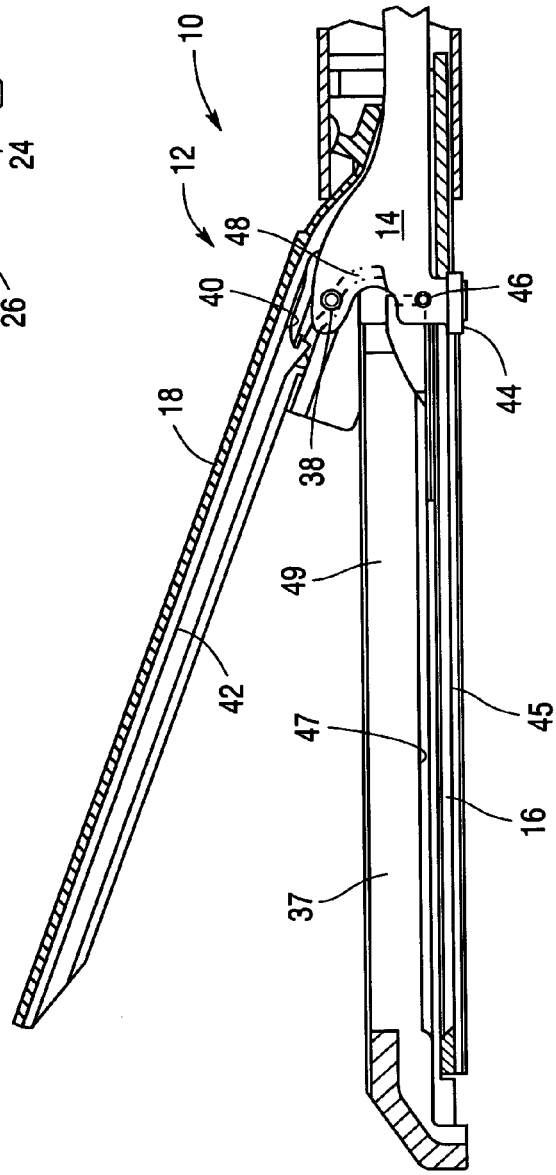

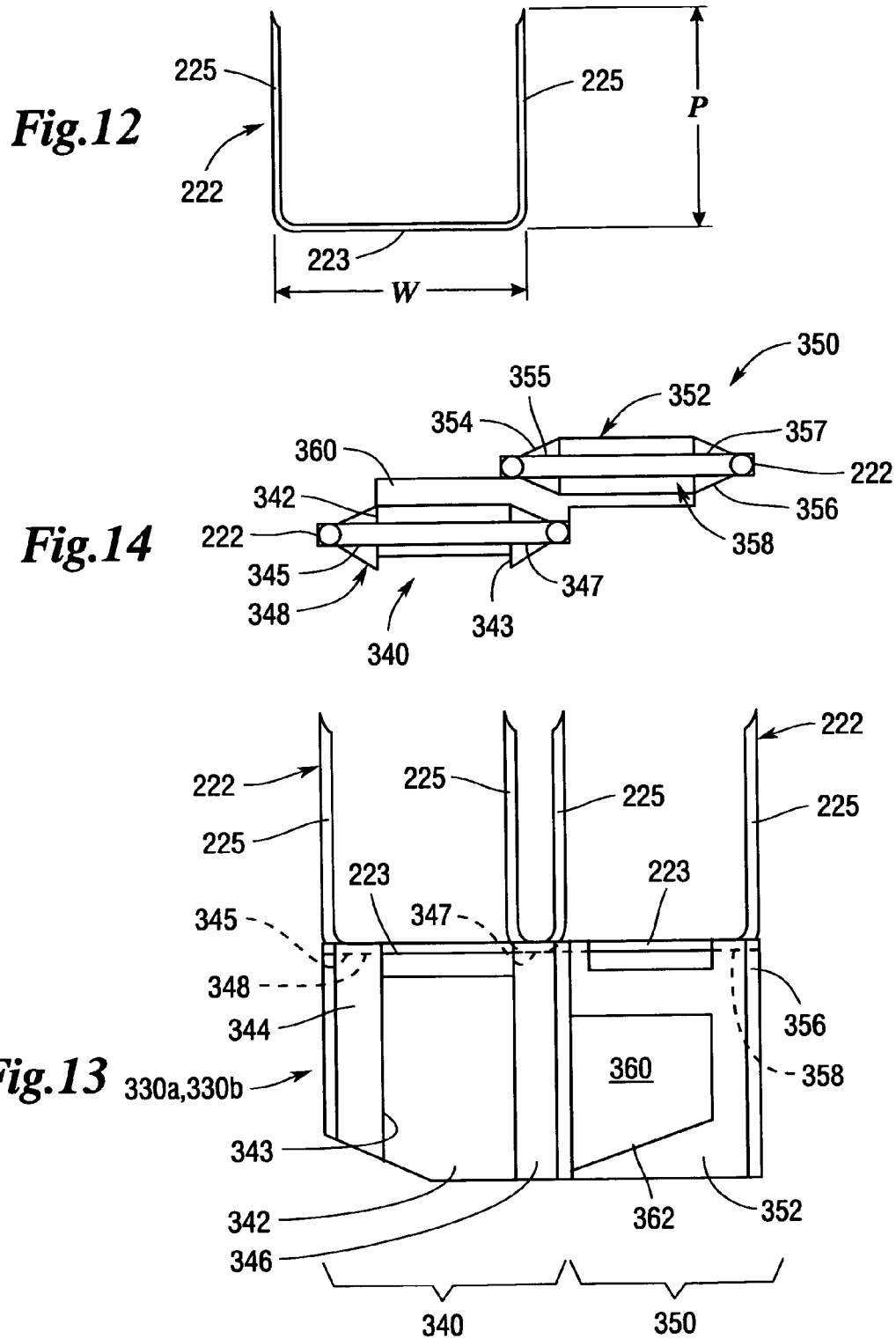

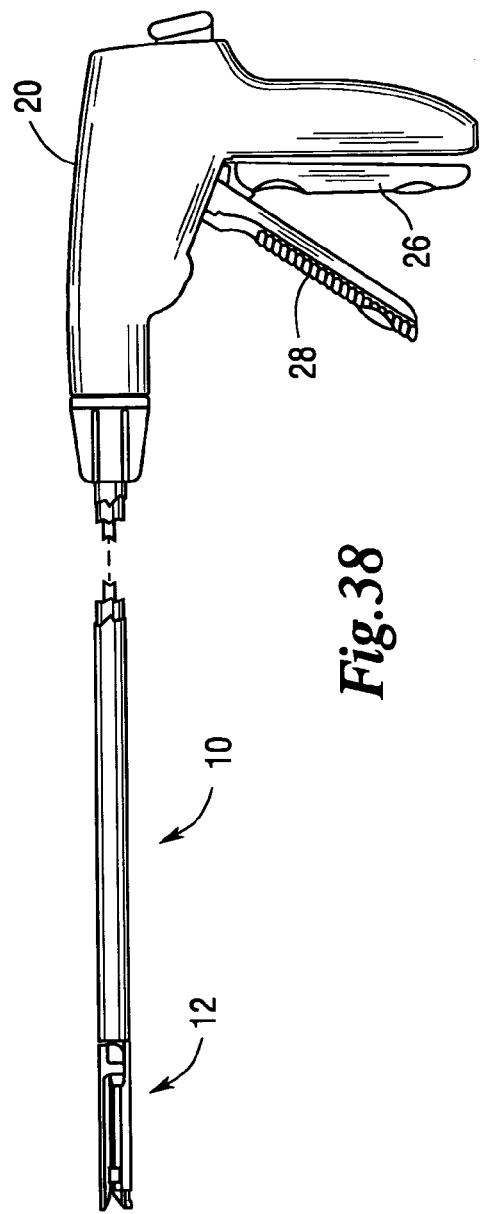
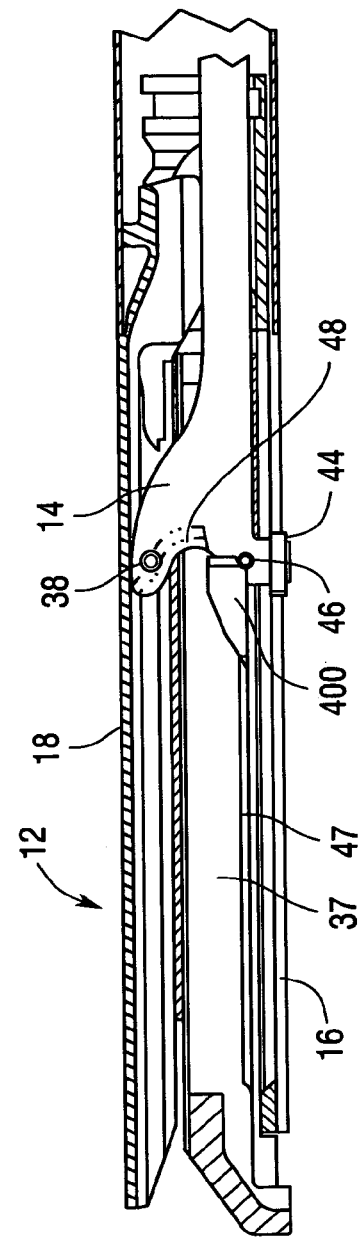
Fig. 38
Fig. 39

STAPLE CARTRIDGES FOR FORMING STAPLES HAVING DIFFERING FORMED STAPLE HEIGHTS

FIELD OF THE INVENTION

The present invention relates in general to stapling instruments that are capable of applying lines of staples and, more particularly, to improvements relating to staple cartridges for use with surgical stapling instruments that are capable of applying lines of staples having differing formed staple heights to tissue while simultaneously cutting the tissue.

BACKGROUND OF THE INVENTION

Surgical staplers have been used in the prior art to simultaneously make a longitudinal incision in tissue and apply lines of staples on opposing sides of the incision. Such instruments commonly include a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of reciprocating wedges that, when driven distally, pass through openings in the staple cartridge and engage drivers supporting the staples to effect the firing of the staples toward the anvil.

An example of a surgical stapler suitable for endoscopic applications is described in U.S. Patent Application No. US 2004/0232196 A1, the disclosure of which is herein incorporated by reference in its entirety. In use, a clinician is able to close the jaw members of the stapler upon tissue to position the tissue prior to firing. Once the clinician has determined that the jaw members are properly gripping tissue, the clinician can then fire the surgical stapler, thereby severing and stapling the tissue. The simultaneous severing and stapling avoids complications that may arise when performing such actions sequentially with different surgical tools that respectively only sever or staple.

Whenever a transection of tissue is across an area of varied tissue composition, it would be advantageous for the staples that are closest to the cut line to have one formed height that is less than the formed height of those staples that are farthest from the cut line. In practice, the rows of inside staples serve to provide a hemostatic barrier, while the outside rows of staples with larger formed heights provide a cinching effect where the tissue transitions from the tightly compressed hemostatic section to the non-compressed adjacent section. In other applications, it may be useful for the staples in a single line of staples to have differing formed heights.

U.S. Pat. Nos. 4,941,623 and 5,027,834 to Pruitt disclose surgical stapler and cartridge arrangements that employ staples that have different prong lengths to ultimately achieve lines of staples that have differing formed heights. Likewise, WO 2003/094747A1 discloses a surgical stapler and cartridge that has six rows of staples wherein the outer two rows of staples comprise staples that are larger than the staples employed in the inner two rows and middle rows of staples. Thus, all of these approaches require the use of different sizes of staples in the same cartridge.

Consequently, a significant need exists for an improved cartridge for a stapling instrument that can form lines of staples that have differing formed heights without the need to employ different sizes of staples in the same cartridge.

BRIEF SUMMARY OF THE INVENTION

In accordance with one embodiment of the present invention there is a provided a staple cartridge for use with a stapling device that has an actuator that is selectively actuatable in an axial direction and an anvil portion that is selectively movable between open and closed positions. In one embodiment, the staple cartridge comprises a cartridge body that is supportable within the stapling device for selective confronting relationship with the anvil portion thereof when in a closed position. The cartridge body is configured to axially receive the actuator therein. The staple cartridge further comprises at least one first staple driver that is movably supported within the cartridge body for contact by the actuator such that, as the actuator is axially advanced through the cartridge body, the first staple drivers are driven in a direction towards the anvil when the anvil is in the closed position. Each of the first staple drivers has a first staple support cradle therein for supporting a staple thereon. The first staple support cradle is located a first staple forming distance from a corresponding portion of the closed anvil. At least one second staple driver is movably supported within the cartridge body for contact by the actuator such that as the actuator is axially advanced through the cartridge body, the second staple drivers are driven in the direction towards the closed anvil. Each second staple driver has a second staple support cradle therein for supporting another staple thereon. The second staple support cradle is located a second staple forming distance from another portion of the closed anvil. The second staple forming distance differs from the first staple forming distance.

In accordance with another embodiment of the present invention, there is provided a staple cartridge for use with a surgical instrument that has an end effector that includes an anvil portion that is pivotally attached thereto for travel between open and closed positions. The instrument further includes a firing bar that is selectively axially reciprocatable within the end effector. One embodiment of the staple cartridge comprises a cartridge body that is sized to be supported within the end effector. The cartridge body has a longitudinally extending slot therein for reciprocatingly receiving the firing bar therein. The cartridge further comprises a first plurality of inside staple drivers that are axially aligned in a first row of inside staple drivers on a first side of the longitudinally extending slot in the body. A second plurality of inside staple drivers are also axially aligned in a second row of inside staple drivers on a second side of the longitudinally extending slot. The inside staple drivers are movably supported within the cartridge body for selective movement towards the anvil when the anvil is in a closed position. Each inside staple driver has a first staple support cradle for supporting a staple thereon. The first staple support cradles are each located a first staple forming distance from a corresponding portion of the anvil when the anvil is in a closed position. The cartridge further comprises a first plurality of outside staple drivers that are axially aligned in a first row of outside staple drivers. The first row of outside staple drivers is located on the first side of the longitudinally extending slot and is adjacent to the first row of the inside staple drivers. The cartridge further includes a second plurality of outside staple drivers axially aligned in a second row of outside staple drivers. The second row of outside staple drivers is located on the second side of said elongated slot and is adjacent to the second row of inside staple drivers. Each of the outside staple drivers is movably supported within the cartridge body for selective driving movement towards the anvil when the anvil is in the closed position. Each of the outside staple drivers have a second staple support cradle for supporting another one of the staples thereon. Each second staple support cradle is located a second staple forming distance from another corresponding portion of the anvil when the anvil is in the closed position. The second staple forming distance differs from the first staple forming distance. A wedge sled is supported within the cartridge body for driving contact by the firing bar and actuating contact with the first and second pluralities of inside and outside staple drivers such that, as the firing bar moves within the elongated slot in a first axial direction, the wedge sled drives each of the inside and outside drivers toward the anvil to bring the staples supported thereon into forming contact with the anvil when the anvil is in the closed position.

In accordance with another embodiment of the present invention there is provided a staple cartridge for use with a surgical instrument that has an end effector that includes an anvil portion that is pivotally attached thereto for travel between open and closed positions and which further includes a firing bar that is selectively axially reciprocatable therein. One embodiment of the staple cartridge comprises a cartridge body that is sized to be supported within the end effector. The cartridge body has a longitudinally extending slot therein for reciprocatingly receiving the firing bar therein. A plurality of first inside staple drivers is axially aligned in a first row of first inside staple drivers on a first side of the longitudinally extending slot within the cartridge body. Each of the first inside staple drivers is movably supported within the cartridge body for selective movement towards the anvil when the anvil is in a closed position. Each of the first inside staple drivers supports at least one staple thereon. This embodiment further includes a plurality of first outside staple drivers that are axially aligned in a first row of first outside staple drivers that is adjacent to the first row of the first inside staple drivers. Each of the first outside staple drivers is movably supported within the cartridge body for selective driving movement toward the anvil when the anvil is in the closed position. Each of the first outside staple drivers supports another one of the staples thereon. The cartridge further comprises a wedge sled that is supported within the cartridge body for contact by the firing bar. The wedge sled comprises a first inside sled cam that has a first sled cam height. The first inside sled cam is oriented for sequential sliding actuating contact with the first inside staple drivers in the first row of first inside staple drivers when the firing bar is axially advanced through the elongated slot in a first axial direction such that the first inside staple drivers are driven toward the anvil a first distance equal to the first sled cam height. The wedge sled further comprises a first outside sled cam that has a second sled cam height that differs from the first sled cam height. The first outside sled cam is oriented for sequential actuating contact with the first outside staple drivers in the first row of the first outside staple drivers when the firing bar is axially advanced through the elongated slot in the first axial direction such that the first outside staple drivers are driven towards the anvil a second distance equal to the second sled cam height.

One feature of various embodiments of the present invention is to provide a staple cartridge for a stapling device that employs rows or other pluralities of identically sized staples while facilitating the ability of forming the staples with differing formed (final) heights. In some embodiments, the final heights may be varied across adjacent rows of staples. In other embodiments, the formed heights of the staples may be varied from staple to staple in a single row of staples. Accordingly, various embodiments of the invention provide solutions to the shortcomings of other staple cartridges and stapling devices that must employ different sizes of staples to achieve staples that have varying formed heights. Those of ordinary skill in the art will readily appreciate, however, that these and other details, features and advantages will become further apparent as the following detailed description proceeds.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 1 depicts a partially cut away side elevation view of a surgical stapling and severing instrument in an open position.

FIG. 2 depicts a cross-sectional side elevation detail view along the line 2-2 of FIG. 1 of an end effector of the surgical stapling and severing instrument.

FIG. 12 is a side view of a staple that may be employed with various embodiments of the present invention.

FIG. 13 is a front elevational view of one inside double driver of one embodiment of the present invention supporting two staples thereon.

FIG. 14 is a top view of the inside double driver and staples of FIG. 13.

FIG. 38 depicts a view in centerline section of the distal end of the surgical stapling and severing instrument of FIG. 1 in a partially fired position.

FIG. 39 depicts a partially cut away side elevation view of the surgical stapling and severing instrument of FIG. 1 in a partially fired position.

DETAILED DESCRIPTION OF THE INVENTION

Figure 3:
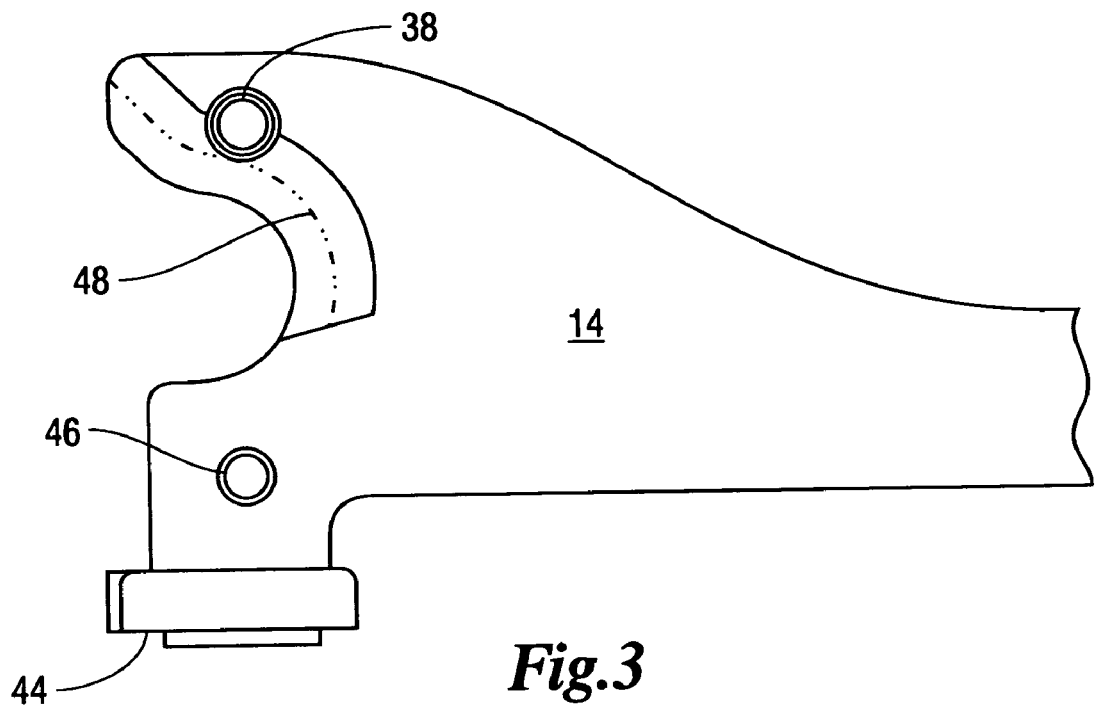
FIG. 3 depicts an enlarged side elevation view of the firing bar of the surgical stapling and severing instrument of FIG. 2.

Turning to the Drawings, wherein like numerals denote like components throughout the several views, FIGS. 1 and 2 depict one embodiment of a surgical stapling and severing instrument 10 that is capable of practicing the unique benefits of the present invention. As the present Detailed Description proceeds, the reader will appreciate, however, that the unique and novel aspects of the present invention may be advantageously employed in connection with a variety of other staplers and stapler instruments without departing from the spirit and scope of the present invention. Accordingly, the scope of protection afforded to the various embodiments of the present invention should not be limited to use only with the specific type of surgical stapling and severing instruments described herein.

As can be seen in FIGS. 1 and 2, the surgical stapling and severing instrument 10 incorporates an end effector 12 having an actuator or E-beam firing mechanism ("firing bar") 14 that advantageously controls the spacing of the end effector 12. In particular, an elongate channel 16 and a pivotally translatable anvil 18 are maintained at a spacing that assures effective stapling and severing. The problems are avoided associated with varying amounts of tissue being captured in the end effector 12.

It will be appreciated that the terms "proximal" and "distal" are used herein with reference to a clinician gripping a handle of an instrument. Thus, the end effector 12 is distal with respect to the more proximal handle portion 20. It will be further appreciated that for convenience and clarity, spatial terms such as "vertical" and "horizontal" are used herein with respect to the drawings. However, surgical instruments are used in many orientations and positions, and these terms are not intended to be limiting and absolute.

The surgical and stapling and severing instrument 10 includes a handle portion 20 that is connected to an implement portion 22, the latter further comprising a shaft 23 distally terminating in the end effector 12. The handle portion 20 includes a pistol grip 24 toward which a closure trigger 26 is pivotally drawn by the clinician to cause clamping, or closing, of the anvil 18 toward the elongate channel 16 of the end effector 12. A firing trigger 28 is farther outboard of the closure trigger 26 and is pivotally drawn by the clinician to cause the stapling and severing of clamped tissue in the end effector 12.

In practice, closure trigger 26 is actuated first. Once the clinician is satisfied with the positioning of the end effector 12, the clinician may draw back the closure trigger 26 to its fully closed, locked position proximate to the pistol grip 24. Then, the firing trigger 28 is actuated. The firing trigger 28 springedly returns when the clinician removes pressure. A release button 30 when depressed on the proximal end of the handle portion 20 releases any locked closure trigger 26.

A closure sleeve 32 encloses a frame 34, which in turn encloses a firing drive member 36 that is positioned by the firing trigger 28. The frame 34 connects the handle portion 20 to the end effector 12. With the closure sleeve 32 withdrawn proximally by the closure trigger 26 as depicted, the anvil 18 springedly opens, pivoting away from the elongate channel 16 and translating proximally with the closure sleeve 32. The elongate channel 16 receives a staple cartridge 37.

Figure 4:
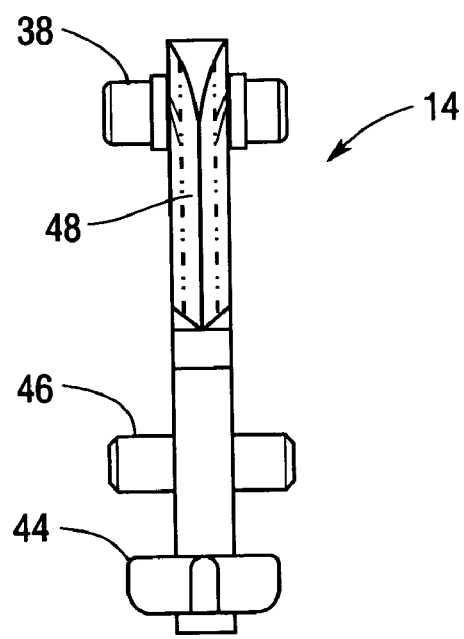
FIG. 4 depicts an enlarged front view of the firing bar of the surgical stapling and severing instrument of FIG. 2.

With particular reference to FIGS. 2-4, the firing bar 14 includes three vertically spaced pins that control the spacing of the end effector 12 during firing. In particular, an upper pin 38 is staged to enter an anvil pocket 40 near the pivot between the anvil 18 and elongate channel 16. When fired with the anvil 18 closed, the upper pin 38 advances distally within a longitudinal anvil slot 42 extending distally through anvil 18. Any minor upward deflection in the anvil 18 is overcome by a downward force imparted by the upper pin 38. Firing bar 14 also includes a lowermost pin, or firing bar cap, 44 that upwardly engages a channel slot 45 in the elongate channel 16, thereby cooperating with the upper pin 38 to draw the anvil 18 and the elongate channel 16 slightly closer together in the event of excess tissue clamped therebetween.

Figure 5:
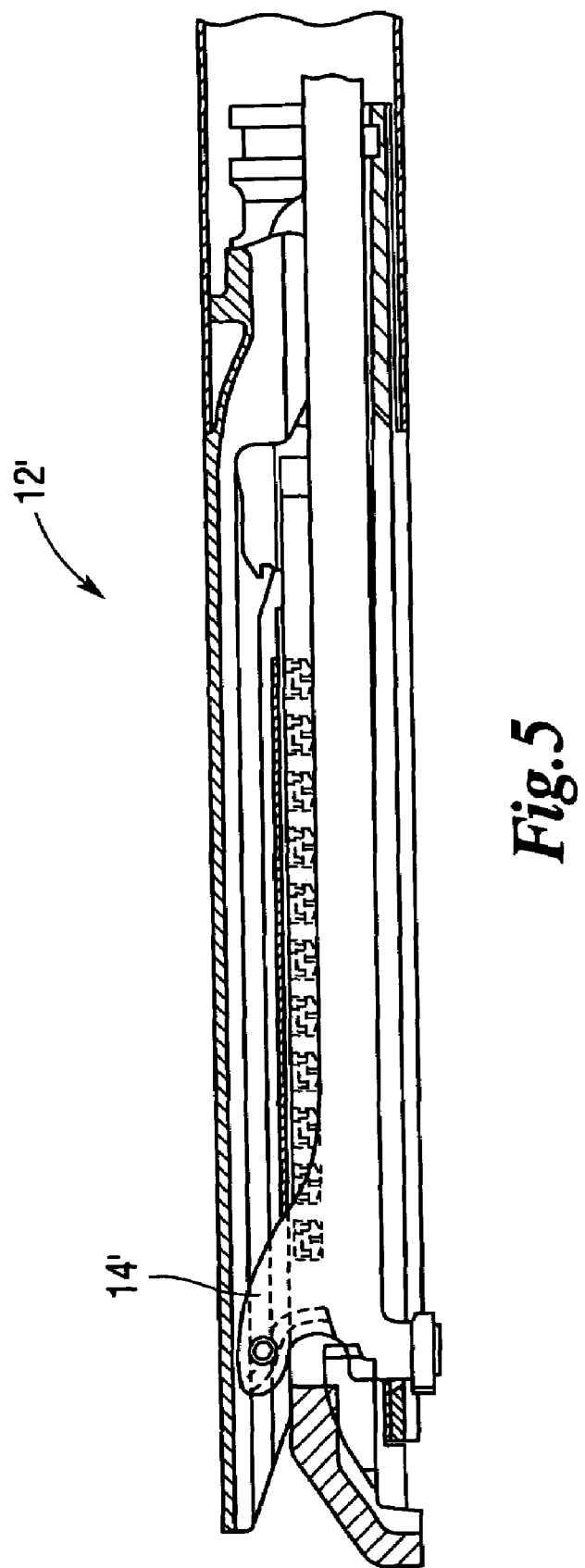
FIG. 5 depicts a cross-sectional side elevation detail view of an alternative end effector for the surgical stapling and severing instrument of FIG. 1, incorporating a firing bar that lacks a middle pin for preventing pinching of the end effector.

The firing bar 14 advantageously includes a middle pin 46 that passes through a firing drive slot 47 formed in a lower surface of the cartridge 300 and an upward surface of the elongate channel 16, thereby driving the staples therein as described below. The middle pin 46, by sliding against the elongate channel 16, advantageously resists any tendency for the end effector 12 to be pinched shut at its distal end. To illustrate an advantage of the middle pin 46, FIG. 5 depicts an alternative end effector 12' that lacks a middle pin on a firing bar 14'. In this depiction, the end effector 12' is allowed to pinch shut at its distal end, which tends to impair desired staple formation.

Returning to FIGS. 2-4, a distally presented cutting edge 48 between the upper and middle pins 38, 46 on the firing bar 14 traverses through a proximally presented, vertical slot 49 in the cartridge 37 to sever clamped tissue. The affirmative positioning of the firing bar 14 with regard to the elongate channel 16 and anvil 18 assure that an effective cut is performed.

The affirmative vertical spacing provided by the E-Beam firing bar 14 is suitable for the limited size available for endoscopic devices. Moreover, the E-Beam firing bar 14 enables fabrication of an anvil 15 with a camber imparting a vertical deflection at its distal end, similar to the position depicted in FIG. 5. This cambered anvil 15 advantageously assists in achieving the desired gap in the end effector 12 even with an anvil 15 having a reduced thickness, which may be more suited to the size limitations of an endoscopic device.

With reference to FIGS. 6-9, the handle portion 20 is comprised of first and second base sections 50 and 52, which are molded from a polymeric material such as a glass-filled polycarbonate. The first base section 50 is provided with a plurality of cylindrically-shaped pins 54. The second base section 52 includes a plurality of extending members 56, each having a hexagonal-shaped opening 58. The cylindrically-shaped pins 54 are received within the hexagonal-shaped openings 58 and are frictionally held therein for maintaining the first and second base sections 50 and 52 in assembly.

A rotating knob 60 has a bore 62 extending completely through it for engaging and rotating the implement portion 22 about its longitudinal axis. The rotating knob 60 includes an inwardly protruding boss 64 extending along at least a portion of the bore 62. The protruding boss 64 is received within a longitudinal slot 66 formed at a proximal portion of the closure sleeve 32 such that rotation of the rotating knob 60 effects rotation of the closure sleeve 32. It will be appreciated that the boss 64 further extends through frame 34 and into contact with a portion of the firing drive member 36 to effect their rotation as well. Thus, the end effector 12 (not shown in FIGS. 6-9) rotates with the rotating knob 60.

A proximal end 68 of the frame 34 passes proximally through the rotating knob 60 and is provided with a circumferential notch 70 that is engaged by opposing channel securement members 72 extending respectively from the base sections 50 and 52. Only the channel securement member 72 of the second base section 52 is shown. The channel securement members 72, extending from the base sections 50, 52 serve to secure the frame 34 to the handle portion 20 such that the frame 34 does not move longitudinally relative to the handle portion 20.

The closure trigger 26 has a handle section 74, a gear segment section 76, and an intermediate section 78. A bore 80 extends through the intermediate section 78. A cylindrical support member 82 extending from the second base section 52 passes through the bore 80 for pivotably mounting the closure trigger 26 on the handle portion 20. A second cylindrical support member 83 extending from the second base section 52 passes through a bore 81 of firing trigger 28 for pivotably mounting on the handle portion 20. A hexagonal opening 84 is provided in the cylindrical support member 83 for receiving a securement pin (not shown) extending from the first base section 50.

A closure yoke 86 is housed within the handle portion 20 for reciprocating movement therein and serves to transfer motion from the closure trigger 26 to the closure sleeve 32. Support members 88 extending from the second base section 52 and securement member 72, which extends through a recess 89 in the yoke 86, support the yoke 86 within the handle portion 20.

A proximal end 90 of the closure sleeve 32 is provided with a flange 92 that is snap-fitted into a receiving recess 94 formed in a distal end 96 of the yoke 86. A proximal end 98 of the yoke 86 has a gear rack 100 that is engaged by the gear segment section 76 of the closure trigger 26. When the closure trigger 26 is moved toward the pistol grip 24 of the handle portion 20, the yoke 86 and, hence, the closure sleeve 32 move distally, compressing a spring 102 that biases the yoke 86 proximally. Distal movement of the closure sleeve 32 effects pivotal translation movement of the anvil 18 distally and toward the elongate channel 16 of the end effector 12 and proximal movement effects closing, as discussed below.

The closure trigger 26 is forward biased to an open position by a front surface 130 interacting with an engaging surface 128 of the firing trigger 28. Clamp first hook 104 that pivots top to rear in the handle portion 20 about a pin 106 restrains movement of the firing trigger 28 toward the pistol grip 24 until the closure trigger 26 is clamped to its closed position. Hook 104 restrains firing trigger 28 motion by engaging a lockout pin 107 in firing trigger 28. The hook 104 is also in contact with the closure trigger 26. In particular, a forward projection 108 of the hook 104 engages a member 110 on the intermediate section 78 of the closure trigger 26, the member 100 being outward of the bore 80 toward the handle section 74. Hook 104 is biased toward contact with member 110 of the closure trigger 26 and engagement with lockout pin 107 in firing trigger 28 by a release spring 112. As the closure trigger 26 is depressed, the hook 104 is moved top to rear, compressing the release spring 112 that is captured between a rearward projection 114 on the hook 104 and a forward projection 116 on the release button 30.

Figure 8:
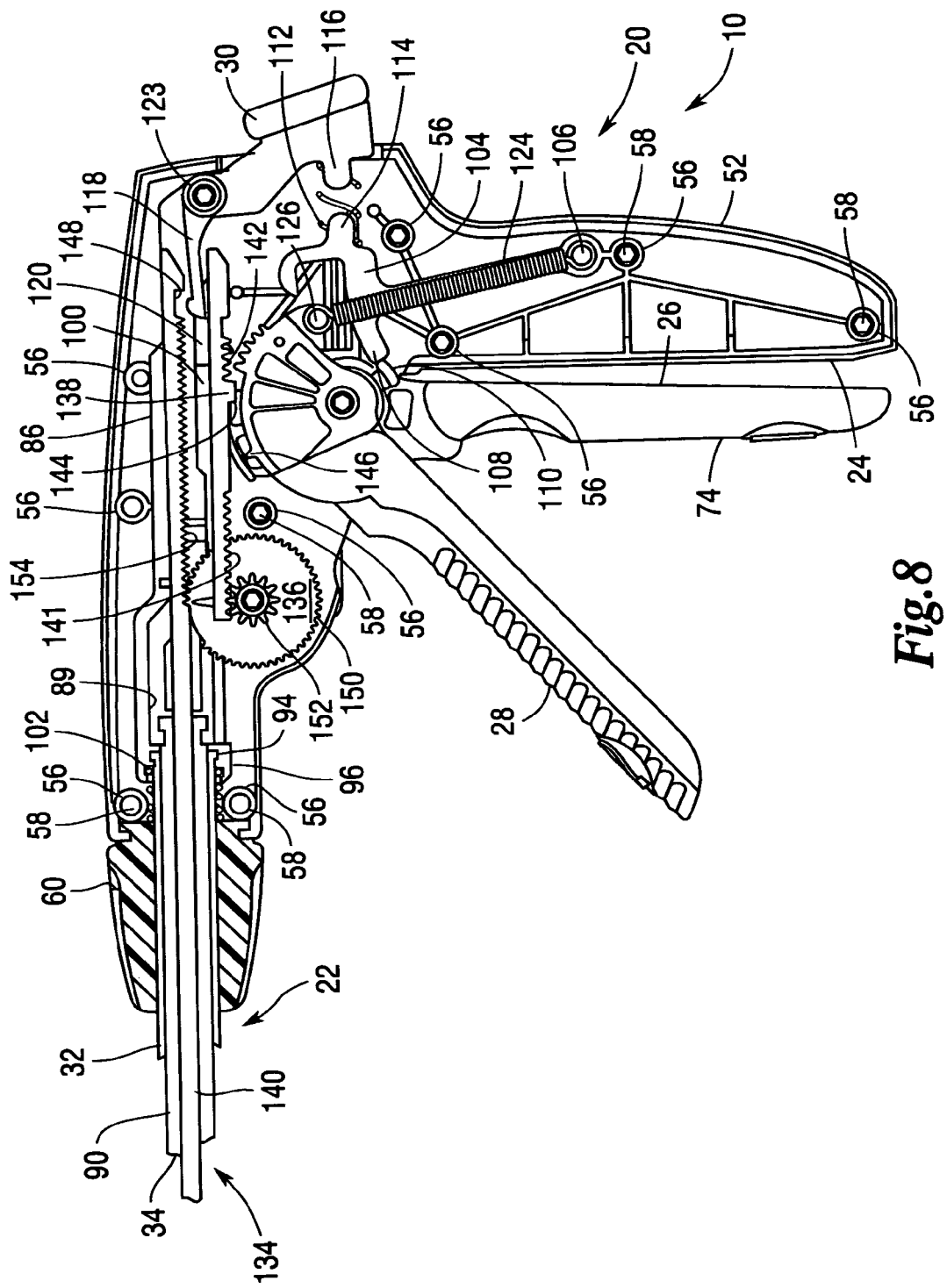
FIG. 8 depicts a side elevational view of the handle portion of the proximal end of the surgical stapling and severing instrument of FIG. 1 with the left side removed to expose interior parts in the closed ("clamped") position.

As the yoke 86 moves distally in response to proximal movement of the closure trigger 26, an upper latch arm 118 of the release button 30 moves along an upper surface 120 on the yoke 86 until dropping into an upwardly presented recess 122 in a proximal, lower portion of the yoke 86. The release spring 112 urges the release button 30 outward, which pivots the upper latch arm 118 downwardly into engagement with the upwardly presented recess 122, thereby locking the closure trigger 26 in a tissue clamping position, such as depicted in FIG. 8.

The latch arm 118 can be moved out of the recess 122 to release the anvil 18 by pushing the release button 30 inward. Specifically, the upper latch arm 118 pivots upward about pin 123 of the second base section 52. The yoke 86 is then permitted to move proximally in response to return movement of the closure trigger 26.

A firing trigger return spring 124 is located within the handle portion 20 with one end attached to pin 106 of the second base section 52 and the other end attached to a pin 126 on the firing trigger 28. The firing return spring 124 applies a return force to the pin 126 for biasing the firing trigger 28 in a direction away from the pistol grip 24 of the handle portion 20. The closure trigger 26 is also biased away from pistol grip 24 by engaging surface 128 of firing trigger 28 biasing front surface 130 of closure trigger 26.

As the closure trigger 26 is moved toward the pistol grip 24, its front surface 130 engages with the engaging surface 128 on the firing trigger 28 causing the firing trigger 28 to move to its "firing" position. When in its firing position, the firing trigger 28 is located at an angle of approximately 45° to the pistol grip 24. After staple firing, the spring 124 causes the firing trigger 28 to return to its initial position. During the return movement of the firing trigger 28, its engaging surface 128 pushes against the front surface 130 of the closure trigger 26 causing the closure trigger 26 to return to its initial position. A stop member 132 extends from the second base section 52 to prevent the closure trigger 26 from rotating beyond its initial position.

The surgical stapling and severing instrument 10 additionally includes a reciprocating section 134, a multiplier 136 and a drive member 138. The reciprocating section 134 comprises a wedge sled in the implement portion 22 (not shown in FIGS. 6-9) and a metal drive rod 140.

The drive member 138 includes first and second gear racks 141 and 142. A first notch 144 is provided on the drive member 138 intermediate the first and second gear racks 141, 142. During return movement of the firing trigger 28, a tooth 146 on the firing trigger 28 engages with the first notch 144 for returning the drive member 138 to its initial position after staple firing. A second notch 148 is located at a proximal end of the metal drive rod 140 for locking the metal drive rod 140 to the upper latch arm 118 of the release button 30 in its unfired position.

The multiplier 136 comprises first and second integral pinion gears 150 and 152. The first integral pinion gear 150 is engaged with a first gear rack 154 provided on the metal drive rod 140. The second integral pinion gear 152 is engaged with the first gear rack 141 on the drive member 138. The first integral pinion gear 150 has a first diameter and the second integral pinion gear 152 has a second diameter which is smaller than the first diameter.

Figure 6:
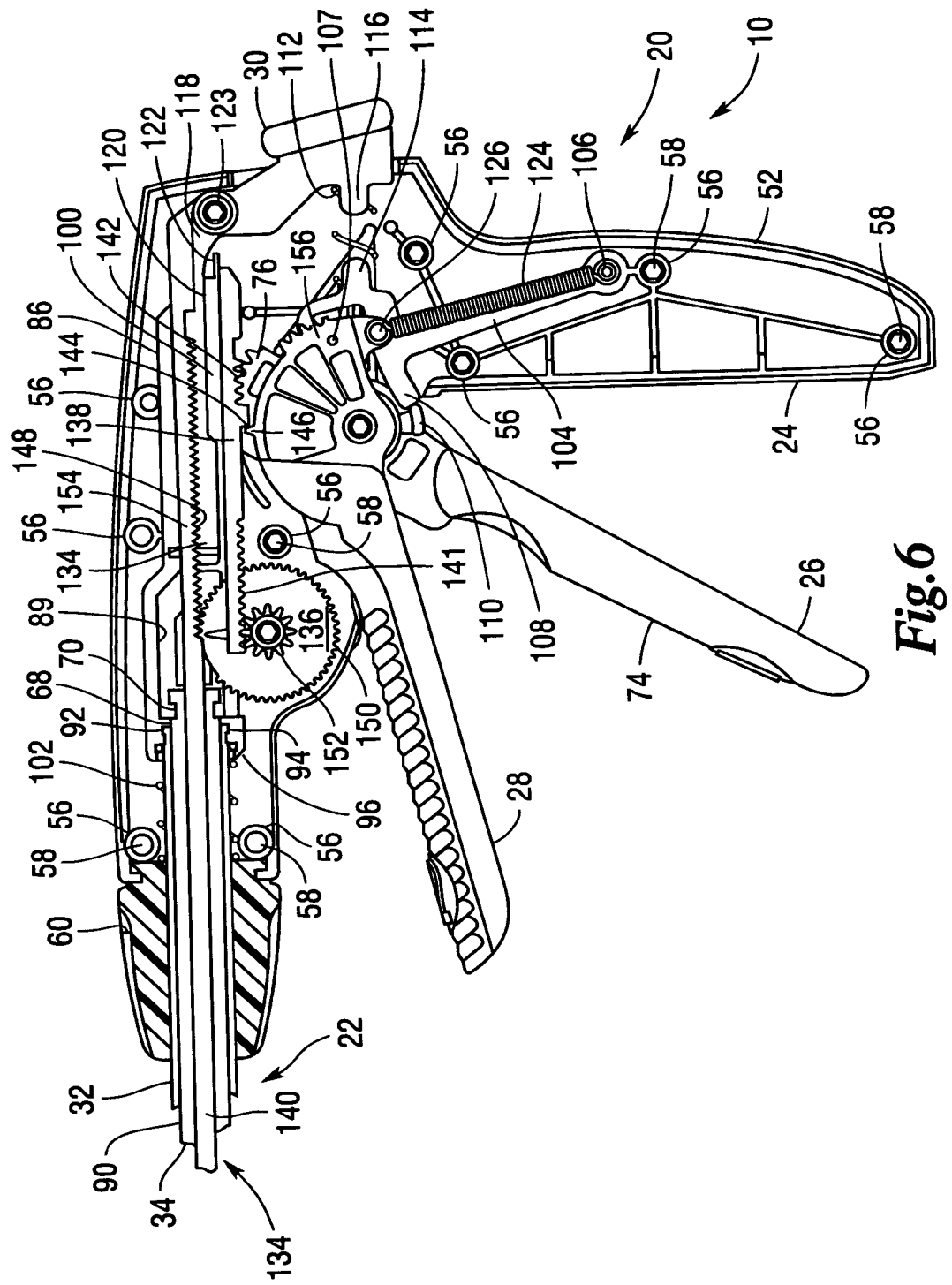
FIG. 6 depicts a side elevational view of a handle portion of a proximal end of the surgical stapling and severing instrument of FIG. 1 with a left side removed to expose interior parts in an unclamped, unfired ("start") position.
Figure 7:
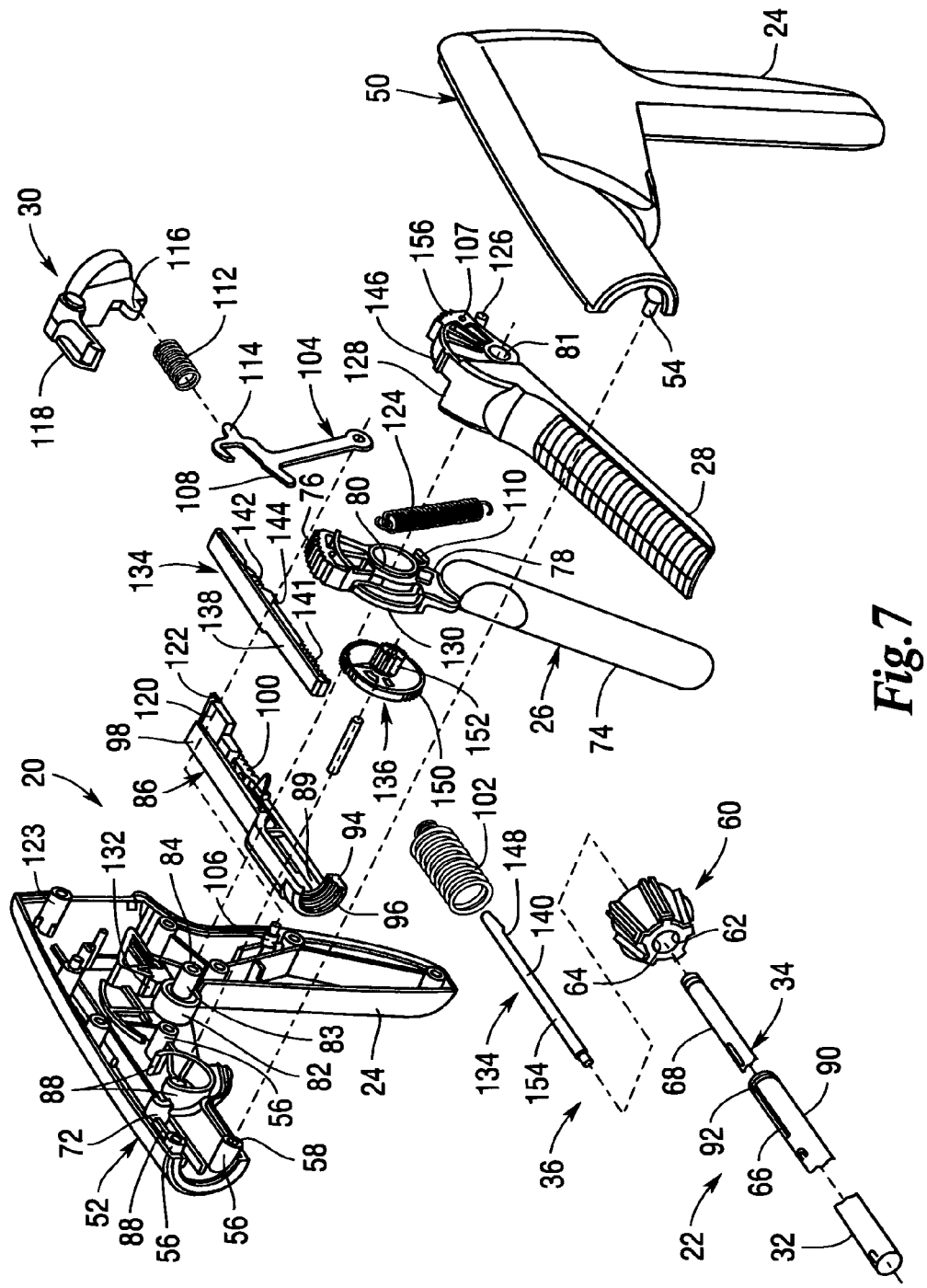
FIG. 7 depicts a perspective, exploded view of the handle portion of the proximal end of the surgical stapling and severing instrument of FIG. 1.
Figure 9:
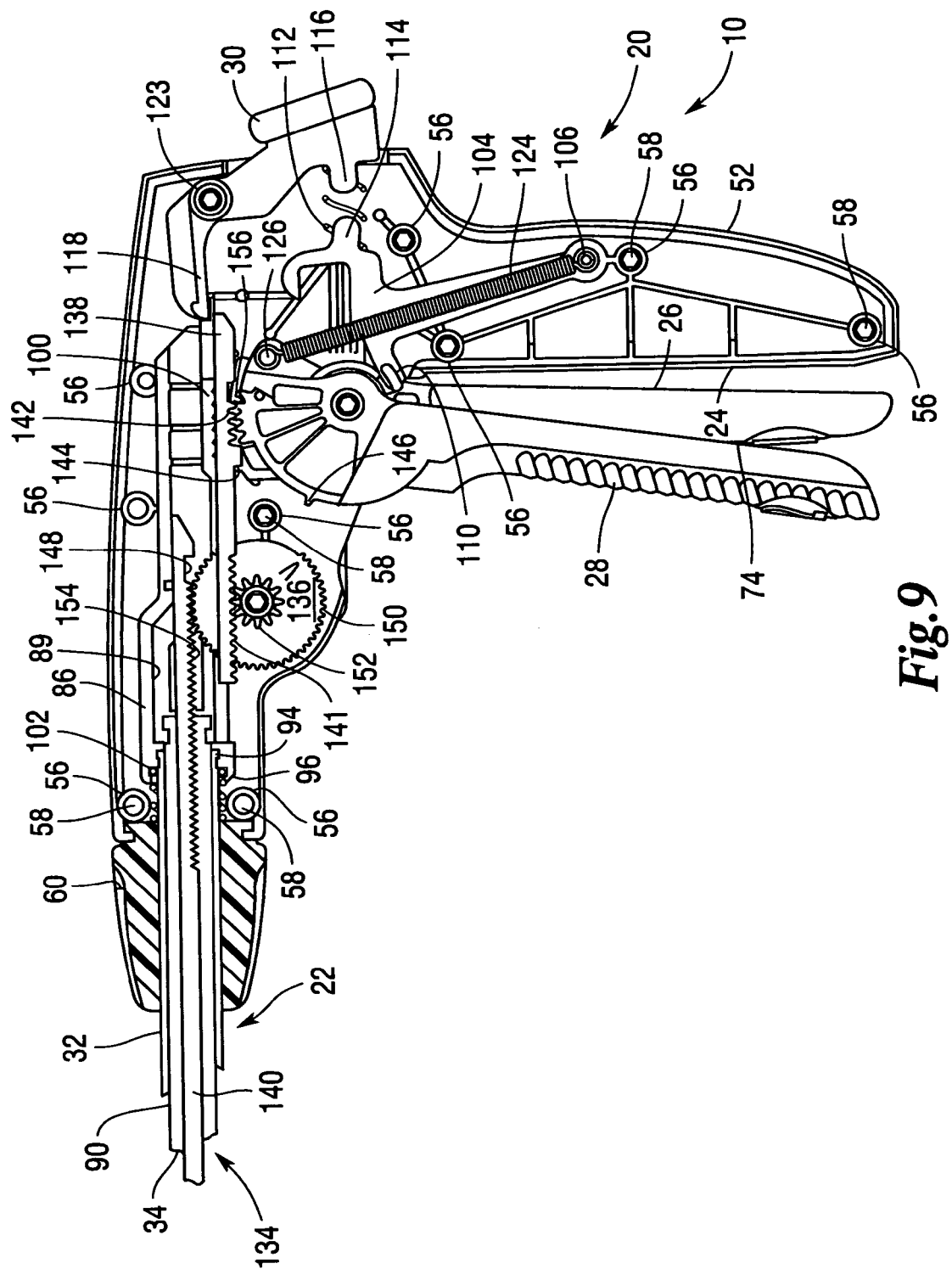
FIG. 9 depicts a side elevational view of the handle portion of proximal end of surgical stapling and severing instrument of FIG. 1 with the left side removed to expose interior parts in the stapled and severed ("fired") position.

FIGS. 6, 8 and 9 depict respectively the handle portion 20 in the start position (open and unfired), a clamped position (closed and unfired) and a fired position. The firing trigger 28 is provided with a gear segment section 156. The gear segment section 156 engages with the second gear rack 142 on the drive member 138 such that motion of the firing trigger 28 causes the drive member 138 to move back and forth between a first drive position, shown in FIG. 8, and a second drive position, shown in FIG. 9. In order to prevent staple firing before tissue clamping has occurred, the upper latch arm 118 on the release button 39 is engaged with the second notch 148 on the drive member 138 such that the metal drive rod 140 is locked in its proximal-most position, as depicted in FIG. 6. When the upper latch arm 118 falls into the recess 122, the upper latch arm 118 disengages with the second notch 148 to permit distal movement of the metal drive rod 140, as depicted in FIG. 9.

Because the first gear rack 141 on the drive member 138 and the gear rack 154 on the metal drive rod 140 are engaged with the multiplier 136, movement of the firing trigger 28 causes the metal drive rod 140 to reciprocate between a first reciprocating position, shown in FIG. 8, and a second reciprocating position, shown in FIG. 9. Since the diameter of the first pinion gear 150 is greater than the diameter of the second pinion gear 152, the multiplier 136 moves the reciprocating section 134 a greater distance than the drive member 138 is moved by the firing trigger 28. The diameters of the first and second pinion gears 150 and 152 may be changed to permit the length of the stroke of the firing trigger 28 and the force required to move it to be varied. It will be appreciated that the handle portion 20 is illustrative and that other actuation mechanisms may be employed. For instance, the closing and firing motions may be generated by automated means.

One embodiment of an end effector 12 of the surgical stapling and severing instrument 10 is depicted in further detail in FIGS. 18, 19, and 23-26. As described above, the handle portion 20 produces separate and distinct closing and firing motions that actuate the end effector 12. The end effector 12 advantageously maintains the clinical flexibility of this separate and distinct closing and firing (i.e., stapling and severing). In addition, the end effector 12 introduces the aforementioned ability to affirmatively maintain the closed spacing during firing after the clinician positions and clamps the tissue. Both features procedurally and structurally enhance the ability of the surgical stapling and severing instrument 10 by ensuring adequate spacing for instances where an otherwise inadequate amount of tissue is clamped and to enhance the clamping in instances where an otherwise excessive amount of tissue has been clamped.

Figure 10:
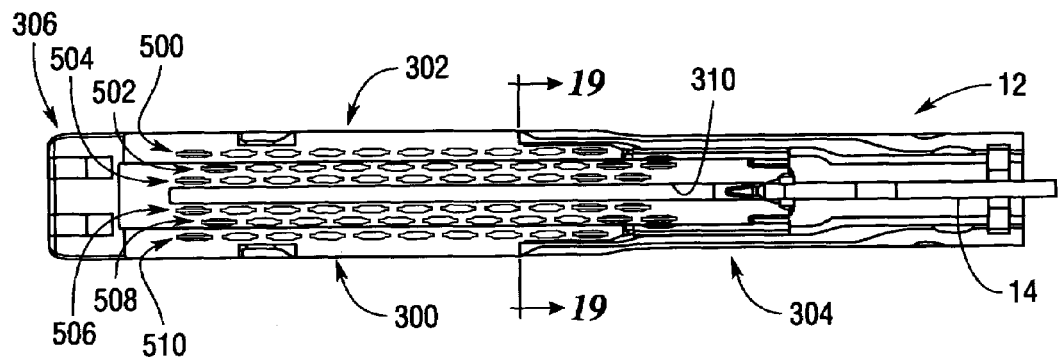
FIG. 10 depicts a plan view of a staple cartridge installed in an end effector of an embodiment of the present invention.

FIG. 10 depicts a staple cartridge embodiment 300 of the present invention installed in the end effector 12 with the firing bar 14 in its unfired, proximal position. The staple cartridge 300 has a cartridge body 302 that is divided by an elongated slot 310 that extends from a proximal end 304 of the cartridge 300 towards a tapered outer tip 306. A plurality of staple-receiving channels 320a-320f are formed within the staple cartridge body 302 and are arranged in six laterally spaced longitudinal rows 500, 502, 504, 506, 508, 510, with three rows on each side of the elongated slot 310. Positioned within the staple-receiving channels 320a-320f are the staples 222. See FIGS. 10 and 11.

Figure 11:
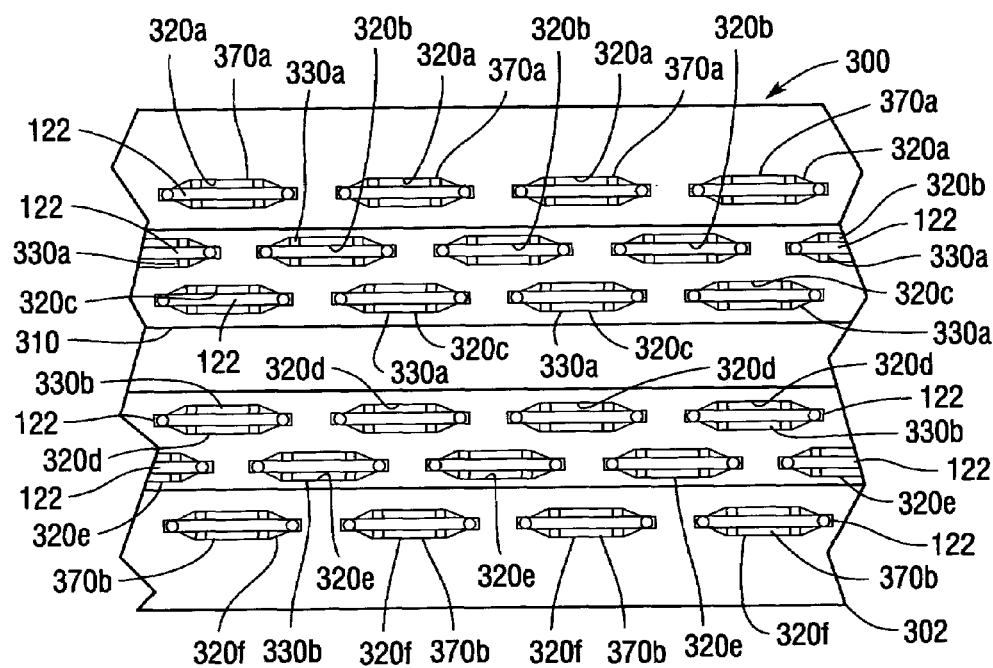
FIG. 11 is an enlarged plan view of a portion of a staple cartridge embodiment of the present invention.

The cartridge 300 further includes four laterally spaced longitudinal rows of staple drivers 330a, 330b, 370a, and 370b as shown in FIG. 11. The "first" inside staple drivers 330a are slidably mounted within corresponding channels 320b and 320c such that each driver 330a supports two staples 222, one in a channel 320b and one in a channel 320c. Likewise, the "second" inside drivers 330b are slidably mounted within channels 320d and 320e such that each driver 330b supports two staples 222, one in a channel 320d and one in a channel 320e. The "outside" drivers 370a and 370b are slidably mounted within the staple-receiving channels 320a and 320f, respectively. Each of the outside drivers 370a and 370b supports a single staple 222. Drivers 370a are referred to herein as "first" outside drivers and drivers 370b are referred to herein as "second" outside drivers.

FIG. 12 illustrates a staple 222 that may be used in connection with the various embodiments of the present invention. The staple 222 includes a main portion 223 and two prongs 225. The prongs 225 each have a length "P" and the main portion has a width "W". The reader will appreciate that a variety of different types of staples may be employed. For example, for a vascular staple, "P" may be approximately 0.102 inches; for a regular staple, "P" may be approximately 0.134 inches; and for a thick tissue staple, "P" may be approximately 0.160 inches. For all such staples, "W" may be approximately 0.120 inches. Other sizes of staples 222 may be employed in the manners discussed below.

The inside staple drivers 330a located on one side of the elongated slot 310 are referred to herein as "first" inside staple drivers and the inside staple drivers 330b located on the other side of the elongated slot 310 are referred to herein as "second" inside staple drivers. As will be discussed in further detail below, in one embodiment, the second inside staple drivers 330b are identical to the first inside staple drivers 330a, except for their orientation in their respective channels in the cartridge body 302.

Figure 14A:
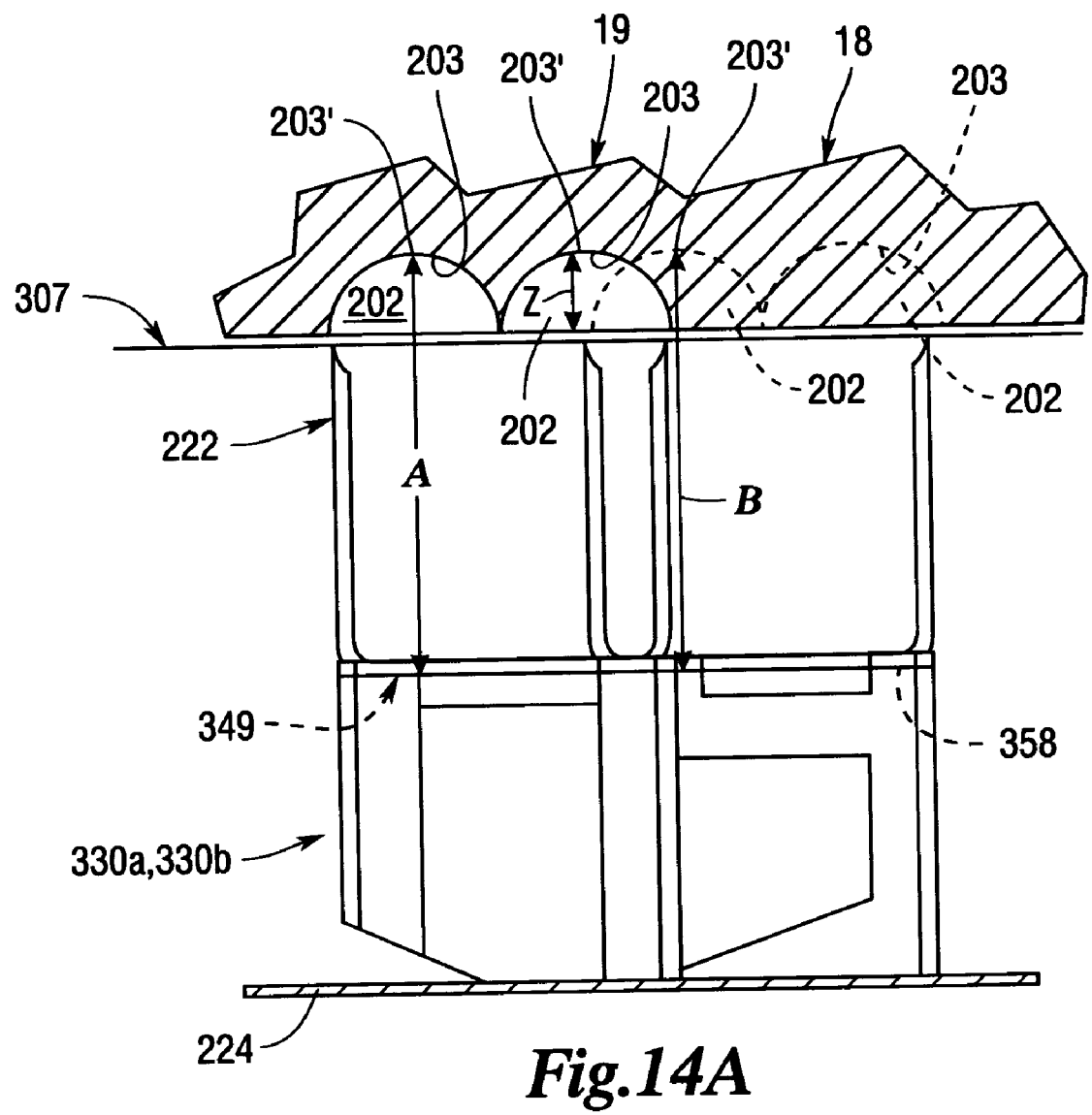
FIG. 14A is an elevational view of the inside double driver of FIG. 13 within a portion of a staple cartridge mounted in the end effector and also illustrating a corresponding portion of the anvil when in a closed position.
Figure 15:
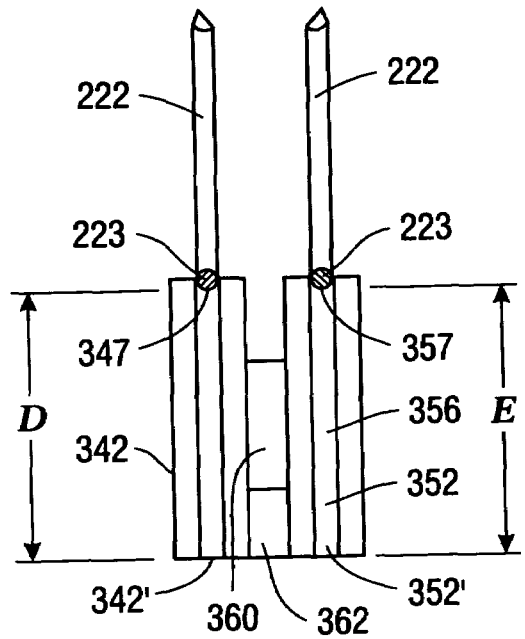
FIG. 15 is a right side elevational view of the inside double driver and staples of FIGS. 13 and 14.

FIGS. 13-15 illustrate one embodiment of a "first" inside double driver 330a for supporting and driving staples 222. As can be seen in those Figures, the staple driver 330a has a primary driver portion 340 and a secondary driver portion 350 that is connected to the first primary portion 340 by a central base member 360. The primary driver portion 340 has a primary driver base 342 that has a groove 343 therein adapted to mate with a corresponding vertically extending tongue (not shown) in the cartridge body 302 for guiding and stabilizing the driver 330a as it moves within its respective channel. The primary driver portion 340 further has a first forward support column 344 and a first rearward support column 346 protruding upward from the first driver base 342. The first forward support column 344 has a first forward staple-receiving groove 345 therein and the first rearward support column 346 has a first rearwardly staple-receiving groove 347 therein. See FIGS. 13-15. The first forward support column 344 and the first rearward support column 346 are spaced from each other and collectively form a first staple cradle 348 for supporting the main portion 223 of the staple 222 therein.

Similarly, the secondary driver portion 350 has a secondary driver base 352 and a secondary forward support column 354 and a secondary rearward support column 356 protruding out from the second driver base 352. The secondary forward support column 354 has a secondary forward staple-receiving groove 355 therein and the secondary rearward support column 356 has a secondary rearward staple-receiving groove 357 therein. The secondary forward support column 354 and the secondary rearward support column 356 are spaced from each other and collectively form a secondary staple cradle 358 for supporting the main portion 223 of another staple 222 therein.

As can be seen in FIGS. 13 and 15, the central base member 360 has an angled rearwardly facing edge 362 adapted to be engaged by a corresponding sled cam as will be discussed in further detail below. As can be seen in FIGS. 13 and 14, in this embodiment, the secondary forward support column 354 of the secondary driver portion is oriented relative to the first rearward support column 346 such that the staple 222 that is supported in the secondary staple cradle 358 is longitudinally offset from the staple 222 in the first staple cradle 348.

The reader will appreciate that the first inside drivers 330a are each installed in one orientation into a corresponding pair of channels 320b and 320c located on one side of the elongated slot 310 in the cartridge body 302. The second inside staple drivers 330b (located on the opposite side of the elongated slot 310 from the first inside staple drivers 330a) comprise inside drivers 330a rotated 180 degrees so that their respective angled surfaces 363 face towards the proximal end 304 of the cartridge 300 to enable them to be installed in pairs of corresponding channels 320d and 320e. Thus, in this embodiment, only one inside driver configuration is employed which thereby eliminates the need for two different inside staple driver configurations for channels on each side of the elongated slot 310.

Figure 17:
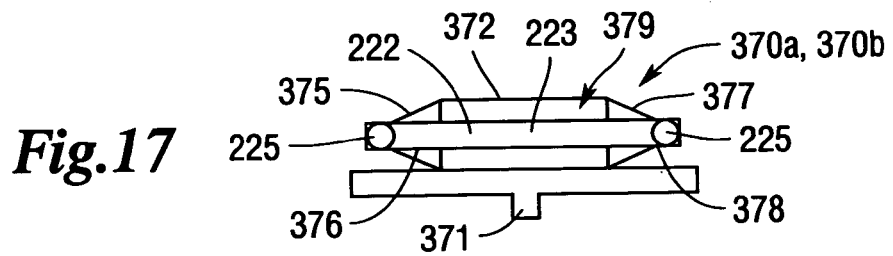
FIG. 17 is a top view of the outside single driver and staple of FIG. 16.
Figure 16:
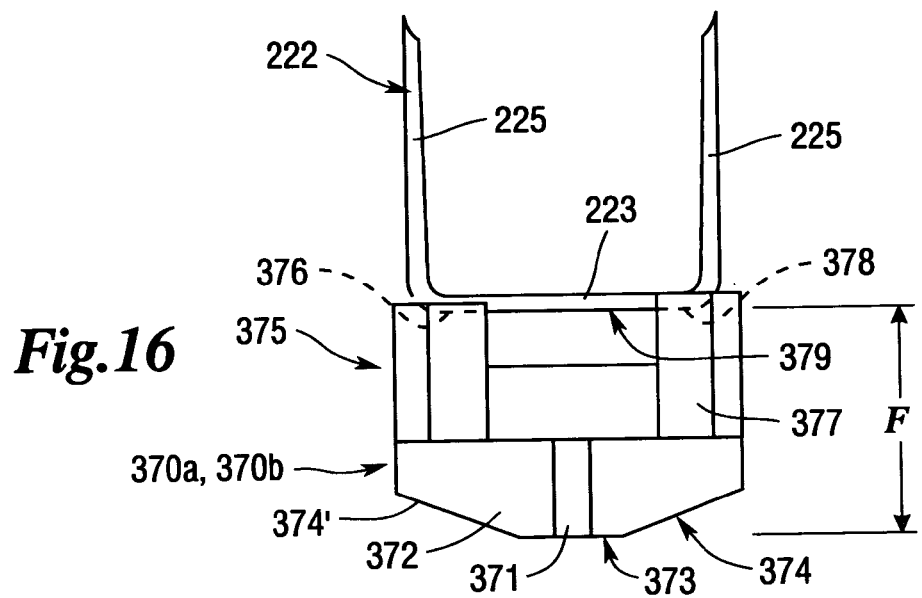
FIG. 16 is a front elevational view of one outside single driver of one embodiment of the present invention supporting a staple thereon.

FIGS. 16 and 17 illustrate one embodiment of a "first" outside staple driver 370a. As can be seen in those FIGS., a first outside staple driver 370a has a second base 372 that has an angled rearwardly facing portion 374. Protruding upward from the second base 372 is a second forward support column 375 that has a second forward staple-receiving groove 376 therein. A second rearward support column 377 also protrudes upward from the second base 372 in a spaced-apart relationship with respect to the second forward support column 375. The second rearward support column 377 has a second rearward staple-receiving groove 378 therein. The support columns 375, 377 collectively form a second staple cradle 379 that is configured to support a staple 222 therein as illustrated in FIGS. 16 and 17. The staple drivers 370a also have a laterally protruding rib 371 which is received in a corresponding groove (not shown) in the cartridge body 302 for guiding and stabilizing the driver 370a as it moves within its respective channel.

The reader will appreciate that a first outside driver 370a is installed in one orientation into a corresponding channel 320a on one side of the elongated slot 310. A second outside staple driver 370b (to be located on the opposite side of the elongated slot 310 from the first outside staple drivers 370a) comprises an outside driver 370a rotated 180 degrees so that the angled surface 374' thereon faces toward the proximal end 304 of the cartridge 300 to enable it to be installed in a corresponding channel 320f in the cartridge body 302. Thus, in this embodiment, only one outside staple driver configuration is employed which avoids the need for two different outside staple driver configurations for channels on each side of the elongated slot 310.

Figure 19:
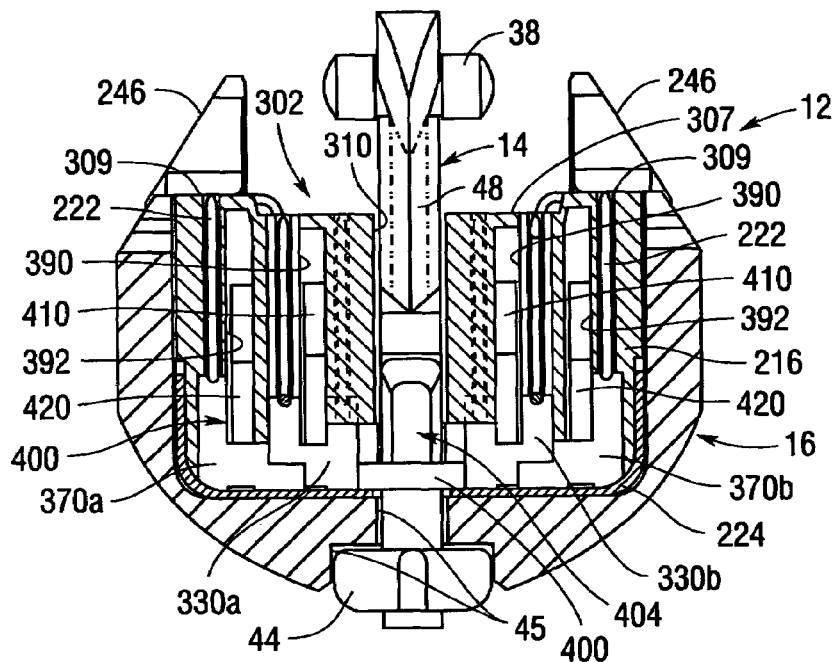
FIG. 19 is a section view taken along line 19-19 of FIG. 10 showing the cross-sectional relationship between the firing bar, elongate channel, wedge sled, staple drivers, staples and staple cartridge.
Figure 19A:
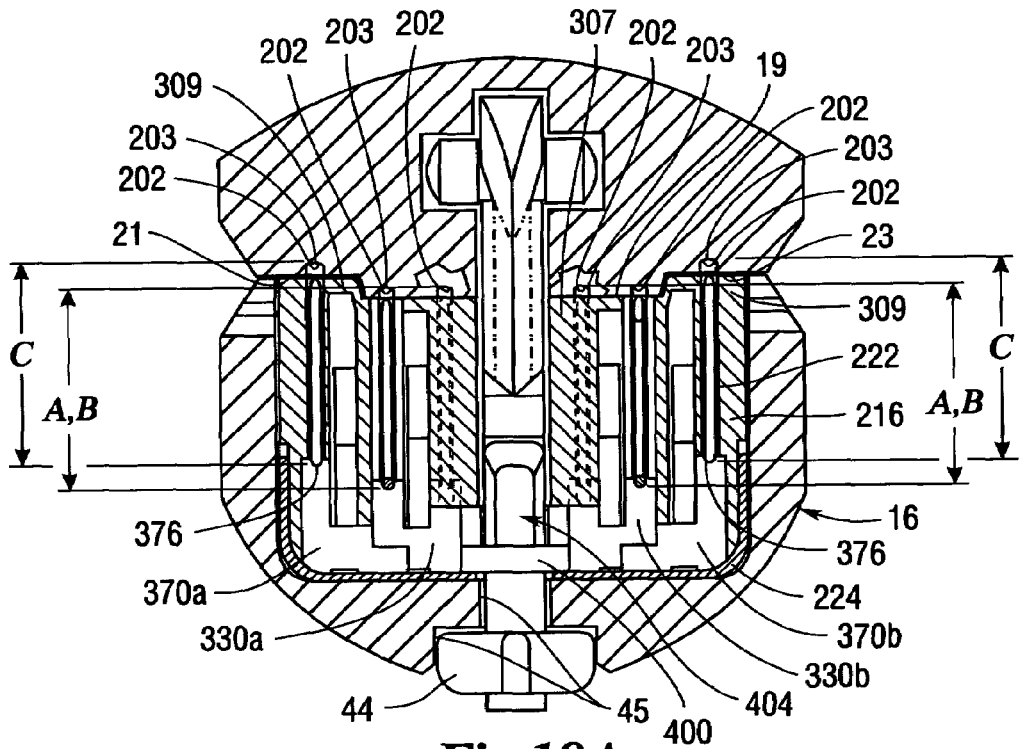
FIG. 19A is another cross-sectional view of an end effector embodiment of the present invention showing the cross-sectional relationship between the firing bar, elongate channel, wedge sled, staple drivers, staples, staple cartridge and anvil.

FIGS. 19 and 19A illustrate in cross-section one embodiment of a staple cartridge of the present invention mounted within one type of end effector 12. The end effector 12 in this embodiment employs a "stepped" anvil 18 of the type illustrated in FIGS. 23-25. In other embodiments, however, the bottom surface of the anvil is planar and not stepped. Other As can be seen in FIGS. 19A, and 23-25, the anvil 18 has a central portion 19 that is offset or not coplanar with the two lateral side portions 21, 23. Accordingly, in this embodiment, the upper surface 306 of the cartridge 300 is provided with a recessed central portion 307 and two lateral side portions 309 that are adapted to closely mate with the corresponding portions 19, 21, 23, respectively, of the anvil 18, when the anvil 18 is in the closed position. See FIG. 19A.

Figure 24:
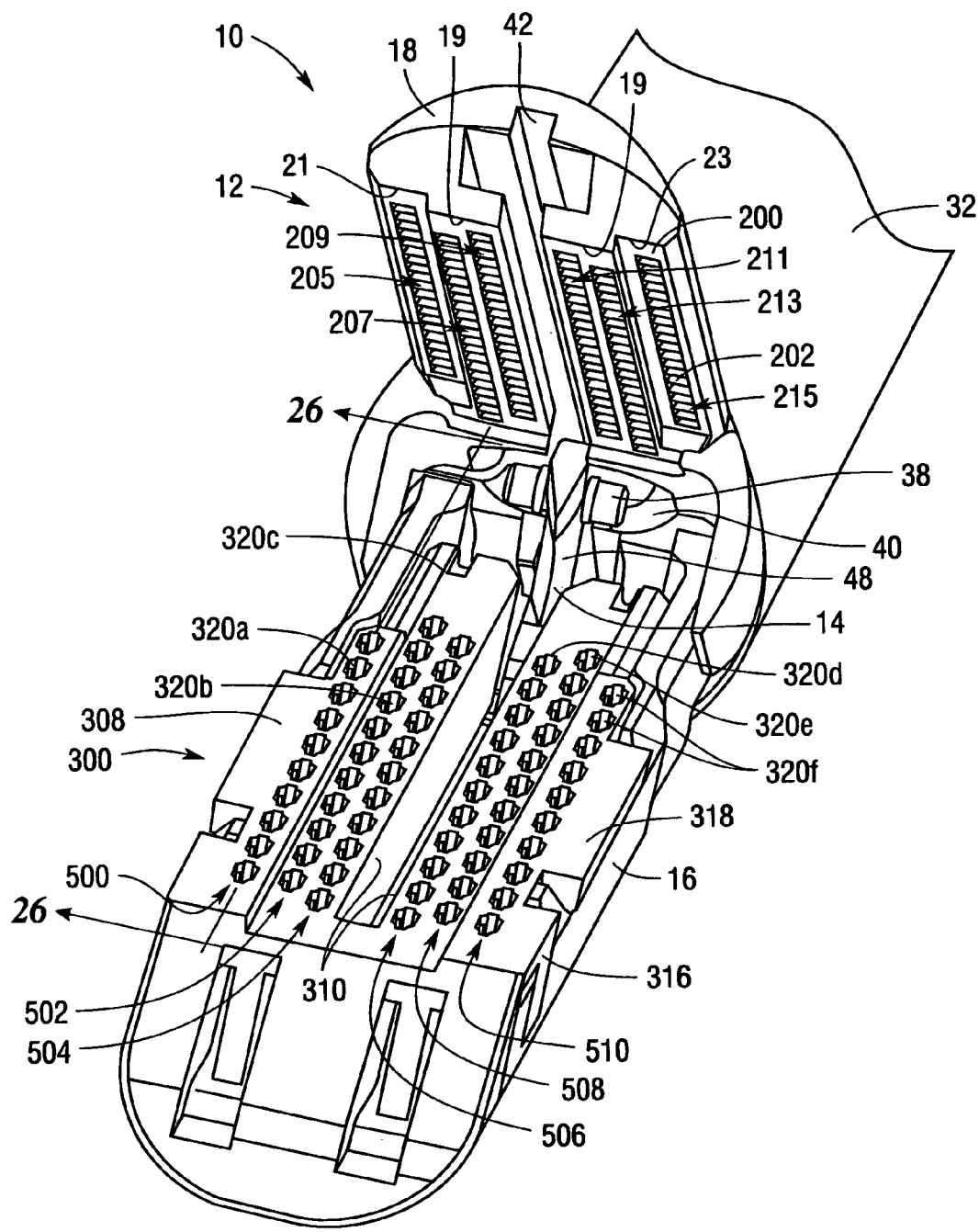
FIG. 24 is an isometric view of the end effector at the distal end of the surgical stapling and severing instrument of FIG. 1 with the anvil in the up or open position exposing the staple cartridge and cutting edge of the firing bar.

As can be seen in FIG. 24, in this embodiment, the under surfaces 200 of anvil 18 are provided with a series of forming pockets 202 that may be arranged in rows that correspond to the rows of channels in the cartridge 300. That is, row 205 of pockets 202 may correspond to channel row 500. Row 207 of pockets may correspond to channel row 502. Row 209 of pockets 202 may correspond to channel row 504. Row 211 of pockets 202 may correspond to channel row 506. Row 213 of pockets 202 may correspond to channel row 508. Row 215 of pockets 202 may correspond to channel row 510. Each pocket 202 has at least one forming surface 203 therein that is adapted to contact the ends of the staple prongs 225 being driven therein to thereby cause the prongs 225 to bend inwardly toward each other. In one embodiment, each pocket 202 has two intersecting arcuate forming surfaces 203 that are oriented as shown in FIG. 14A. Each arcuate forming surface has an apex 203' that defines a maximum pocket depth "Z". However other forming pocket configurations could be employed.

Returning to FIGS. 18 and 19, it can be seen that in one embodiment, the cartridge body 302 is mounted within the cartridge tray 224. As illustrated in FIG. 19, the cartridge body 302 is formed with two inside longitudinally extending slots 390 and two outside longitudinally extending slots 392. Slots 390 and 392 extend from the proximal end 304 of the cartridge to its tapered outer tip 306 (shown in FIG. 10). This embodiment further includes a wedge sled 400 that slidably supported on the cartridge tray 224. One wedge sled embodiment 400 includes a pair of inside sled cams 410, wherein one inside sled cam 410 corresponds to one of the inside longitudinally extending slots 390 and wherein the other inside sled cam 410 corresponds to the other inside longitudinally extending slot 390. See FIG. 19. The wedge sled 400 further includes a pair of outside sled cams 420, wherein one outside sled cam 420 corresponds to one of the outside longitudinally extending slots 392 and the other outside sled cam 420 corresponds to the other outside longitudinally extending slot 392 as shown in FIG. 19. When assembled, the cartridge tray 224 holds the wedge sled 400 and the drivers 330a, 330b, 370a, 370b inside the cartridge body 302.

Figure 18:
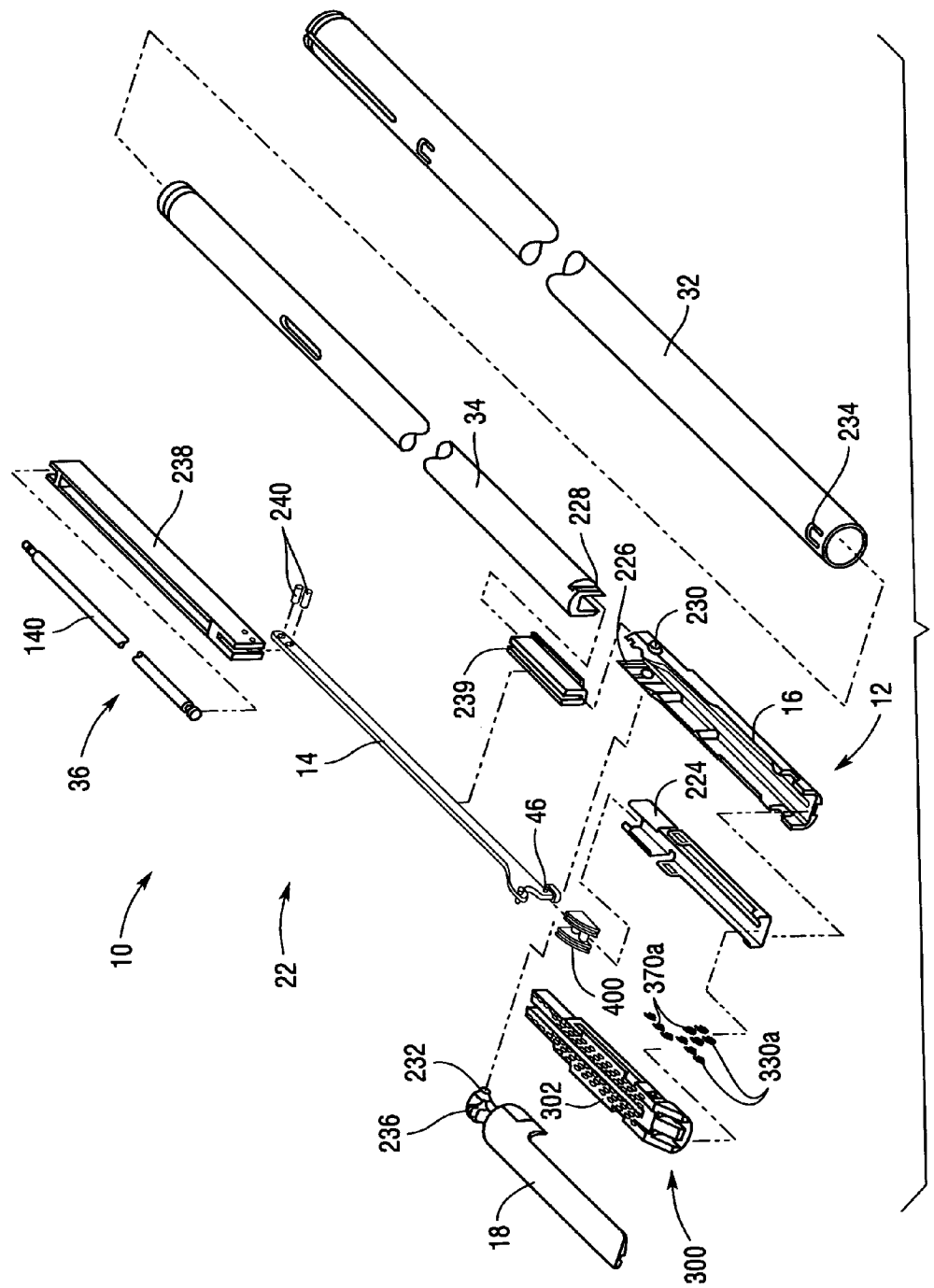
FIG. 18 is an isometric exploded view of the implement portion of the surgical stapling and severing instrument of FIG. 1.

As can be seen in FIG. 18, the elongate channel 16 has a proximally placed attachment cavity 226 that receives a channel anchoring member 228 on the distal end of the frame 34 for attaching the end effector 12 to the handle portion 20. The elongate channel 16 also has an anvil cam slot 230 that pivotally receives an anvil pivot 232 of the anvil 18. The closure sleeve 32 that encompasses the frame 34 includes a distally presented tab 234 that engages an anvil feature 236 proximate but distal to the anvil pivot 232 on the anvil 18 to thereby effect opening and closing of the anvil 18. The firing drive member 36 is shown as being assembled from the firing bar 14 attached to a firing connector 238 by pins 240, which in turn is rotatingly and proximally attached to the metal drive rod 140. The firing bar 14 is guided at a distal end of the frame by a slotted guide 239 inserted therein.

Figure 20:
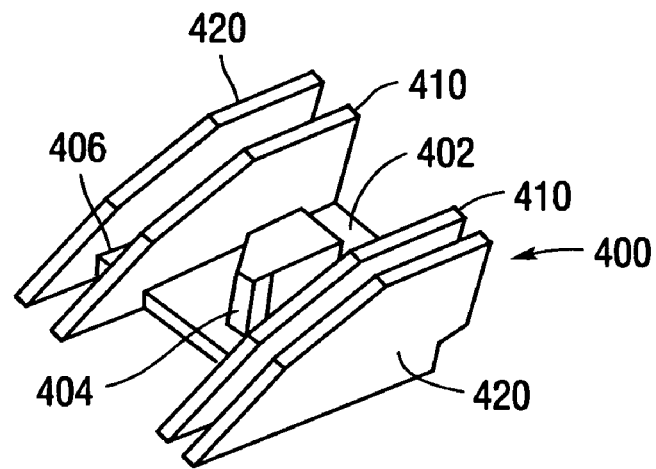
FIG. 20 is a perspective view of one wedge sled embodiment of the present invention.
Figure 21:
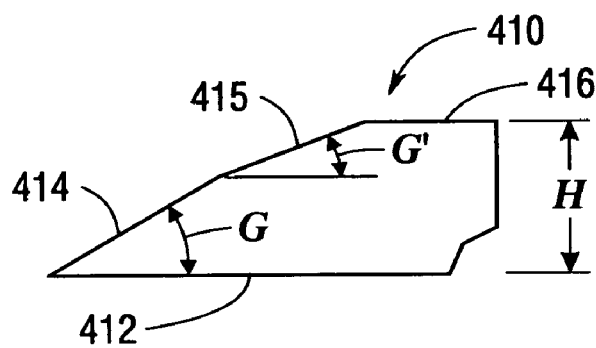
FIG. 21 is a side elevational view of an inside sled cam of the wedge sled depicted in FIG. 20.
Figure 22:
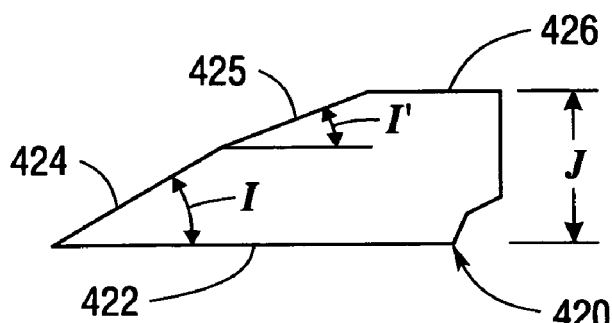
FIG. 22 is a side elevational view of an outside sled cam of the wedge sled depicted in FIG. 20.
Figure 23:
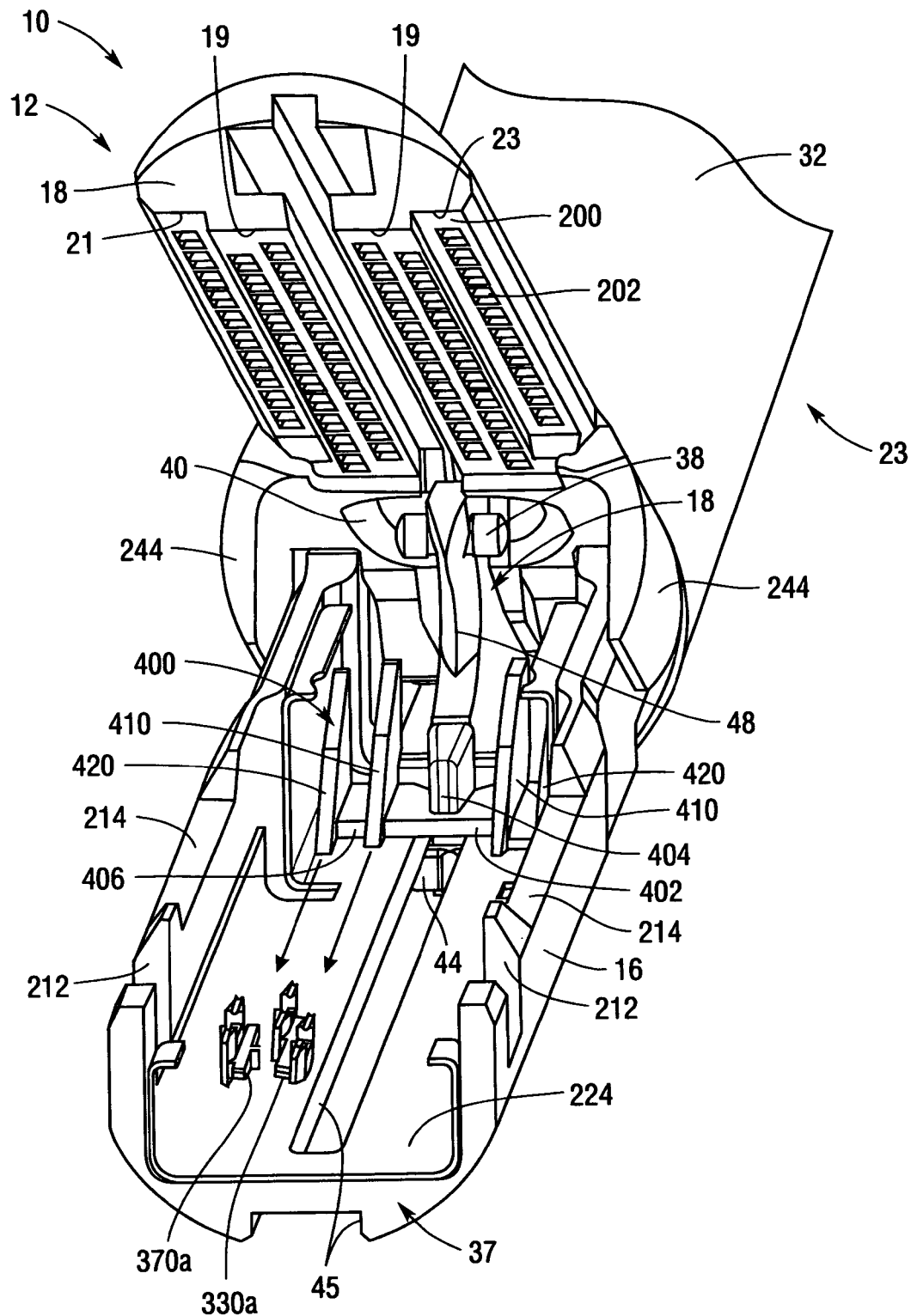
FIG. 23 is an isometric view of the end effector at the distal end of the surgical stapling and severing instrument of FIG. 1 with the anvil in the up or open position with the cartridge largely removed exposing a single staple driver and a double staple driver as exemplary and the wedge sled in its start position against a middle pin of the firing bar.

FIGS. 20-23 illustrate one embodiment of the wedge sled 400 of the present invention. As can be seen in FIGS. 20 and 23, the wedge sled 400 includes a central spacer portion 402 that extends between the inside sled cams 410. A pusher block 404 is formed on the central spacer portion 402 for engagement with the middle pin 46 of the firing bar 14. A side profile of one embodiment of an inside sled cam 410 is depicted in FIG. 21. As can be seen in that FIG., the inside sled cam 410 has a bottom surface 412, and a first camming surface 414 that forms an angle "G" with the bottom surface 412 and a second camming surface 415 that extends to a top surface 416. In one embodiment, for example, the angle "G" may be 35 degrees and the angle "G'" may be 20 degrees. The height of the inside sled cam 410 (the distance between the bottom surface 412 and the top surface 416) is represented as "first" sled cam height "H". In one embodiment, distance "H" is approximately 0.173 inches and the length of the top surface 416 may vary from embodiment to embodiment. As will be further evident as the present Detailed Description proceeds, the first sled cam height represents the vertical distance that the inside sled cams 410 will drive the corresponding inside drivers 330a, 330b toward the anvil 18 during operation.

The wedge sled 400 further comprises lateral spacer portions 406 that extend between the inside sled cams 410 and the outside sled cams 420 as shown in FIGS. 20 and 23. A side profile of one embodiment of an outside sled cam 420 is depicted in FIG. 22. In this embodiment, the outside sled cam 420 has a bottom surface 422 and a first camming surface 424 that forms an angle "I" with respect to the bottom surface 422 and a second camming surface 425 that to a top surface 426. In one embodiment, angle "I" may be approximately 35 degrees and angle "I'" may be approximately 20 degrees. The height of the outside sled cam 420 (the distance between the bottom surface 412 and the top surface 416) is represented as the "second" sled cam height "J". In one embodiment, distance "J" is approximately 0.163 inches. The second sled cam height represents the vertical distance that the outside sled cams 420 will drive the corresponding outside drivers 370a, 370b toward the anvil 18 during operation. The reader will understand that the above-recited dimensions are illustrative of one embodiment and may vary for other embodiments.

With particular reference to FIG. 23, a portion of the staple cartridge 300 is removed to expose portions of the elongate channel 16, such as recesses 212, 214 and to expose some components of the staple cartridge 300 in their unfired position. In particular, the cartridge body 302 (shown in FIG. 18) has been removed. The wedge sled 400 is shown at its proximal, unfired position with a pusher block 404 contacting the middle pin 46 (not shown in FIG. 23) of the firing bar 14. The wedge sled 400 is in longitudinal sliding contact upon the cartridge tray 224 and includes wedges sled cams 410, 420 that force upward the double drivers 330a, 330b and the single drivers 370b, 370b as the wedge sled 400 moves distally. Staples 222 (not shown in FIG. 23) resting upon the drivers 330a, 330b, 370a, 370b are thus also forced upward into contact with the anvil forming pockets 202 in anvil 18 to form closed staples. Also depicted is the channel slot 45 in the elongate channel 16 that is aligned with the elongated slot 310 in the staple cartridge 300.

FIG. 24 depicts the end effector 12, which is in an open position by a retracted closure sleeve 32, with a staple cartridge 300 installed in the elongate channel 16. The firing bar 14 is at its proximal position, with the upper pin 38 aligned in a non-interfering fashion with the anvil pocket 40. The anvil pocket 40 is shown as communicating with the longitudinal anvil slot 42 in the anvil 18. The distally presented cutting edge 48 of the firing bar 14 is aligned with and proximally from removed from the vertical slot 49 in the staple cartridge 300, thereby allowing removal of a spent cartridge and insertion of an unfired cartridge, which may be "snapfit" into the elongate channel 16. Specifically, in this embodiment, extension features 316, 318 of the staple cartridge 300 engage recesses 212, 214, respectively (shown in FIG. 23) of the elongate channel 16.

Figure 25:
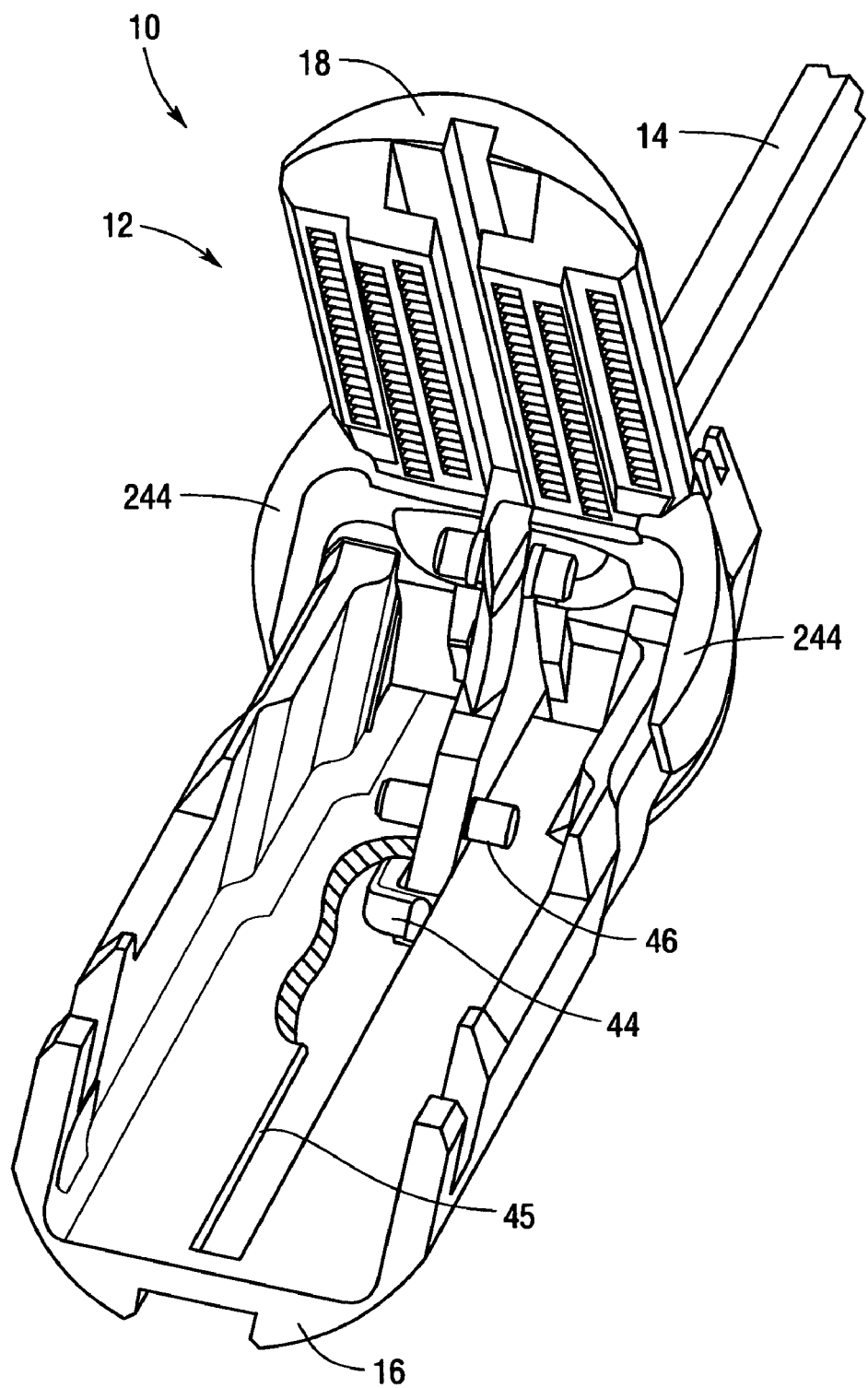
FIG. 25 is an isometric view of the distal end of the surgical stapling and severing instrument of FIG. 1 with the anvil in the up or open position with the staple cartridge completely removed and a portion of an elongate channel removed to expose a lowermost pin of the firing bar.

FIG. 25 depicts the end effector 12 of FIG. 23 with all of the staple cartridge 300 removed to show the middle pin 46 of the firing bar 14 as well as portion of the elongate channel 16 removed adjacent to the channel slot 45 to expose the firing bar cap 44. In addition, portions of the shaft 23 are removed to expose a proximal portion of the firing bar 14. Projecting downward from the anvil 18 near the pivot is a pair of opposing tissue stops 244 which serve to prevent tissue from being positioned too far up into the end effector 12 during clamping.

Figure 26:
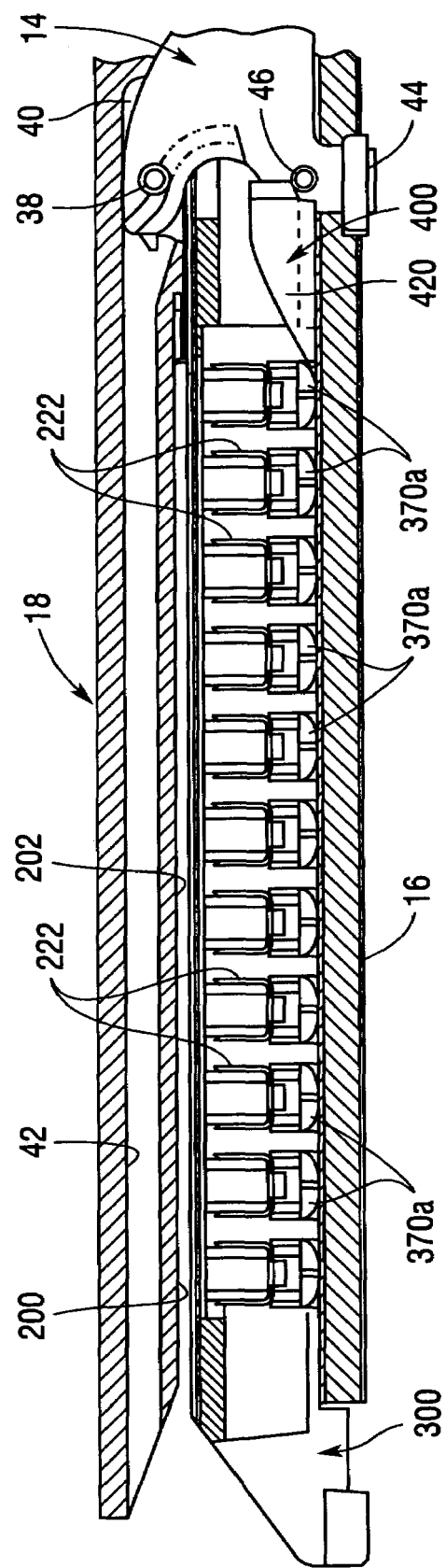
FIG. 26 is a side elevation view in section showing a mechanical relationship between the anvil, elongate channel, and staple cartridge in the closed position of the surgical stapling and severing instrument of FIG. 1, the section generally taken along lines 26-26 of FIG. 24 to expose wedge sled, staple drivers and staples but also depicting the firing bar along the longitudinal centerline.

FIG. 26 depicts the end effector 12 in a closed position with the firing bar 14 in an unfired position. The upper pin 38 is in the anvil pocket 40 and is vertically aligned with the anvil slot 42 for distal longitudinal movement of the firing bar 14 during firing. The middle pin 46 is positioned to push the wedge sled 400 distally so that the sled cams 410, 420 contact and lift double drivers 330a, 330b and the single drivers 370a, 370b, respectively, to drive them upwardly toward the anvil 18.

Figure 15A:
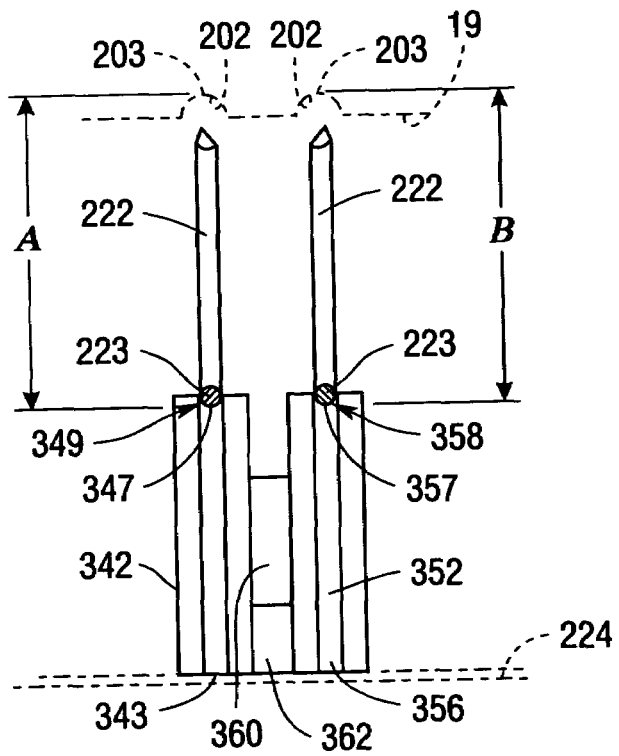
FIG. 15A is another side elevational view of the inside double driver of FIG. 15 wherein corresponding portions of the cartridge tray and anvil are illustrated in broken lines to depict the relationships therebetween.

As can be appreciated from reference to FIGS. 14A, 15A and 19A, in one embodiment of the present invention, the distance between the bottom of the first staple-receiving grooves 345, 347 forming the first staple cradle 349 and the apex 203' of forming surfaces 203 of the corresponding forming pocket 202 of anvil 18, when the anvil 18 is in the closed position and when the inside driver 330a, 330b is supported on the cartridge tray 224, is referred to herein as the first staple forming distance "A". The distance between the bottom of the secondary staple-receiving grooves 345, 347 forming the secondary staple cradle 349 and the apex 203' of the forming surface 203 of the corresponding forming pocket 202 in the anvil 18 when the anvil 18 is in the closed position and the inside driver 330a, 330b is supported on the cartridge tray 224 is referred to herein as the secondary staple forming distance "B". In one embodiment, the first staple forming distance "A" and the secondary staple forming distance "B" are substantially equal to each other. In other embodiments, those distances "A" and "B" may differ from each other.

Figure 16A:
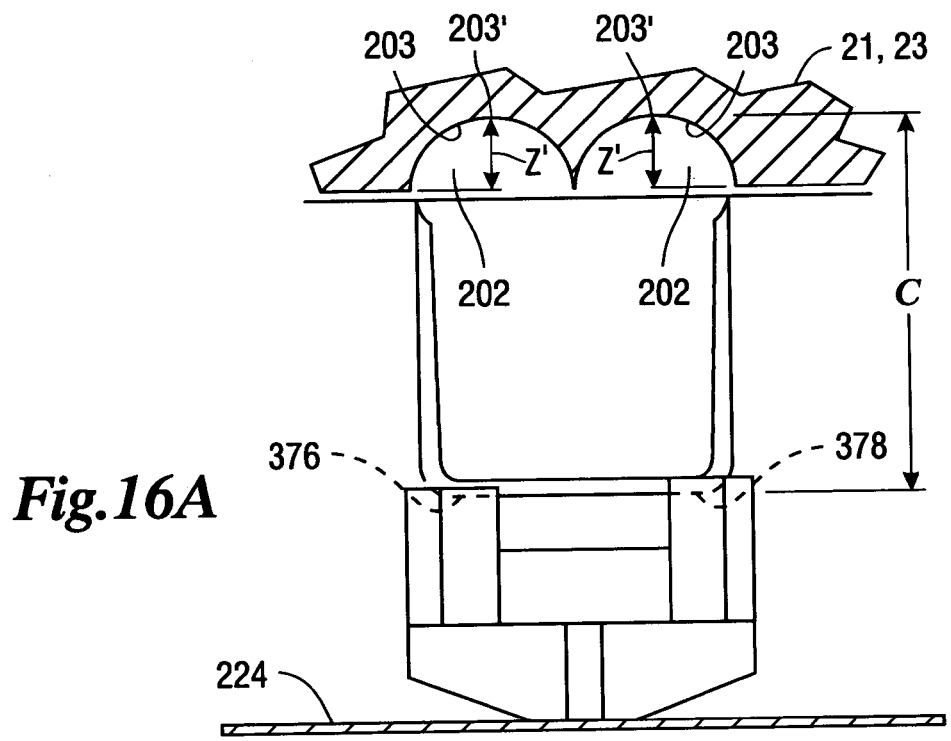
FIG. 16A is another front view of the outside single driver of FIG. 16 with portions of the cartridge tray and anvil shown to illustrate the relationships therebetween.

As illustrated in FIGS. 16A and 19A the distance between the bottom of the second staple-receiving grooves 376, 378 that form the second staple cradle 379 and the apex 203' of the forming surface 203 of a corresponding forming pocket 202 in anvil 18 when the anvil 18 is in the closed position and the outside drivers 370a, 370b are supported on the cartridge channel 224, is referred to herein as a "second" staple forming distance "C".

Figure 27:
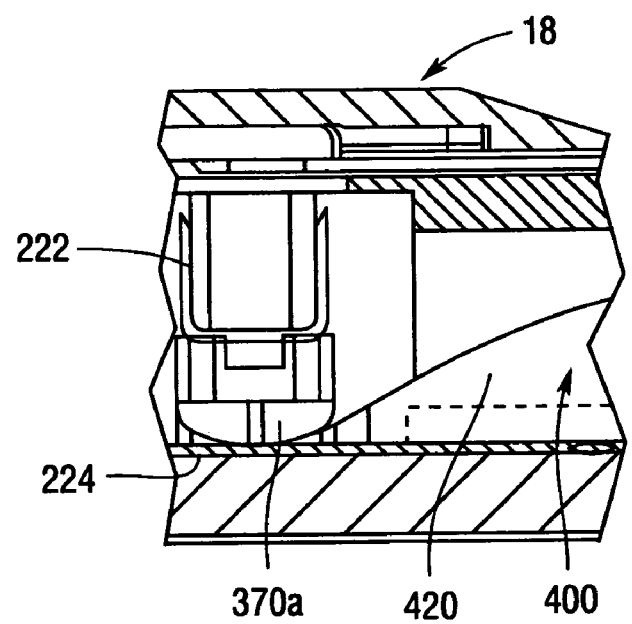
FIG. 27 is a cross-sectional view of a portion of one embodiment of a staple cartridge of the present invention wherein an outside cam of a wedge is adjacent to an outside single driver.
Figure 28:
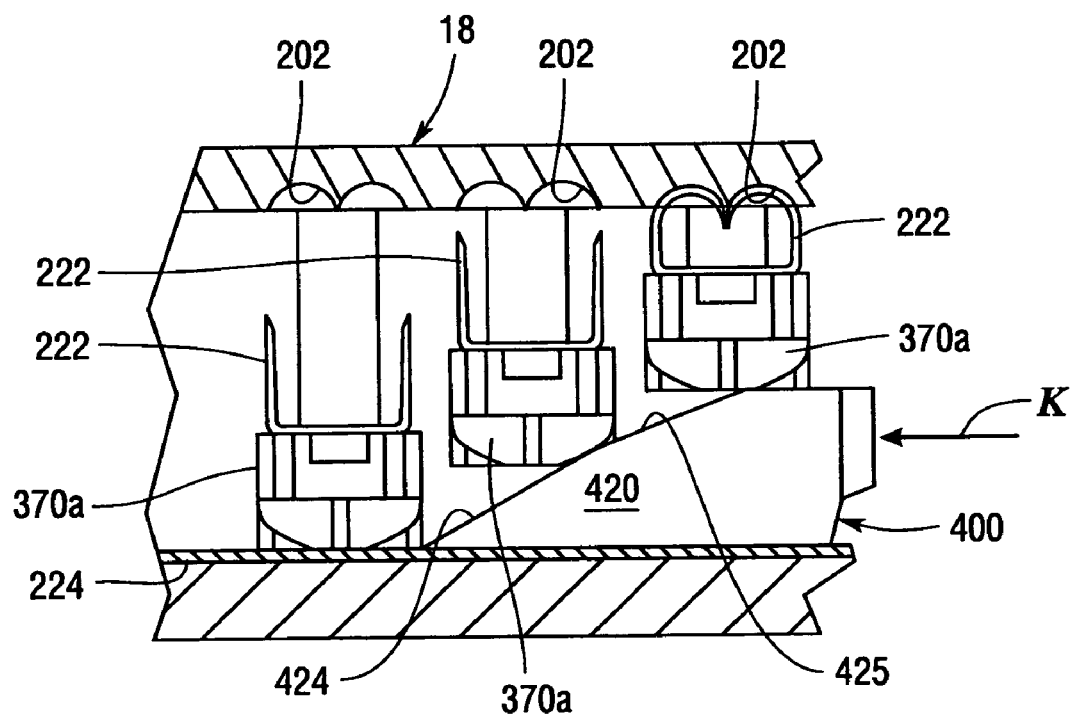
FIG. 28 is a cross-sectional view of a portion of one embodiment of a staple cartridge of the present invention wherein an outside cam of a wedge sled is engaging three outside single drivers.

FIGS. 27 and 28 illustrate the forming of staples supported on some of the first outside drivers 370a. In FIG. 27, one of the outside sled cams 420 of the wedge sled 400 is initially contacting one of the outside drivers 370a. As the wedge sled 400 continues in the driving direction represented by arrow "K" in FIG. 28, the outside sled cam 420 causes the outside drivers 370a drive the staples 222 supported thereby into the staple forming pockets 202 in the anvil 18. Likewise, as the wedge sled 400 is driven in the driving direction "K", the inside sled cams 410 contact the inside drivers 330a, 330b and causes them to drive the staples 222 supported thereby into the corresponding staple forming pockets 202 in the anvil 18.

As indicated above, in some applications involving an area of varied tissue composition, it can be desirable to form rows of staples wherein the formed (final) heights of the staples in a row that is the farthest distance away from the cut line are greater than the formed (final) heights of those staples in the row that is closest to the cut line. In other applications, it may be desirable for the formed heights of the staples in a single row to increase (or decrease) from staple to staple. Another clinical benefit would be to have the formed heights of the staples in the outermost rows larger than formed heights of the staples in the inside rows. The various embodiments of the subject invention can provide these results while employing identical staples in all of the rows.

As the present Detailed Description proceeds, those staples 222 in the outermost rows 520, 530 of staples (those staples formed using the outside staple drivers 370a, 370b) will be referred to hereinafter as staples 222' and those staples in the innermost rows 522, 524, 526, 528 of staples (those staples formed using the inside staple drivers 330a, 330b) will be referred to hereinafter as staples 222". It will be understood, however, that staples 222' and 222" are identical to each other prior to being formed by the various embodiments of the present invention. That is, staples 222' and 222" each have identical prong lengths "P" and widths "W".

Returning to FIGS. 14A-16A and 21 and 22, the above desired effects may be attained by altering the staple forming distances "A", "B", and "C" relative to each other and/or the sled cam heights "H" and "J". In one embodiment of the subject invention, for example, the height "H" of each of the inside sled cams 410 is substantially equal to the sled height "J" of each of the outside sled cams 420. See FIGS. 21 and 22. In this embodiment, the staple forming distances "A" and "B" are substantially equal to each other, but distances "A" and "B" are less than the staple forming distance "C". The distance "D" between the bottoms of the first staple-receiving grooves 345, 347 and the bottom surface 342' of the primary driver base 342 is substantially equal to the distance "E" between the bottoms of the secondary staple-receiving grooves 356, 357 and the bottom surface 352' of the secondary driver base portion 352. See FIG. 15. Also in this embodiment, the distance "F" between the bottoms of the second staple-receiving grooves 376 and 378 and the bottom surface 373 of the third base 372 of the outside drivers 370a, 370b (FIG. 16) is less than distances "D" and "E" (FIG. 15). Because the forming distance "C" is greater than the forming distances "A" and "B", the staples 222 supported and formed by the outside drivers 370a, 370b are not compressed as much as the staples supported and formed by the inside drivers 330a, 330b. It will be understood that similar results may be attained on the opposite side of the elongated slot 310 and the cut line 600 formed in the tissue by using the same arrangements and sizes of inside drivers 330b and outside drivers 370b. In an alternative embodiment, the same effect may be achieved by altering the depths of the forming pockets 202 corresponding to the drivers 330a and 370b such that forming distance "C" is greater than the forming distances "A" and "B". That is, the depth (distance "Z'" in FIG. 16A) of the those forming pockets 202 corresponding to the outside drivers 370a. 370b may be greater than the depth (distance "Z" in FIG. 14A) of the forming pockets 202 that correspond to the inside drivers 330a, 330b.

Figure 29:
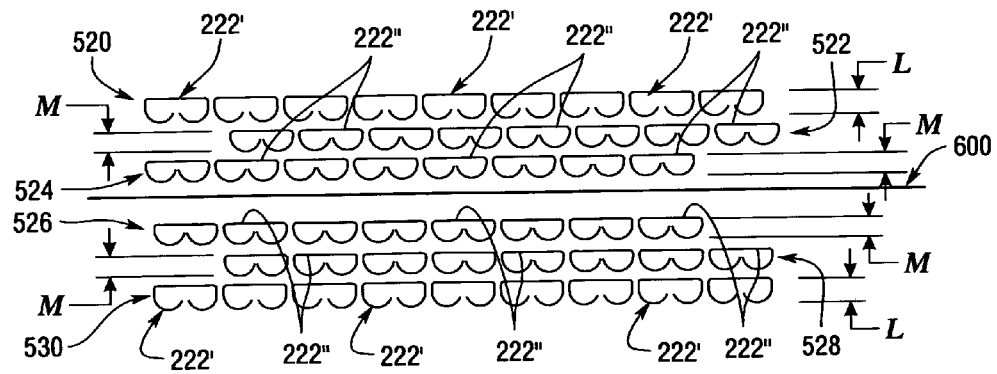
FIG. 29 is a diagrammatic representation of lines of staples installed on each side of a cut line using a surgical stapling and severing instrument of one embodiment of the present invention.
Figure 31:
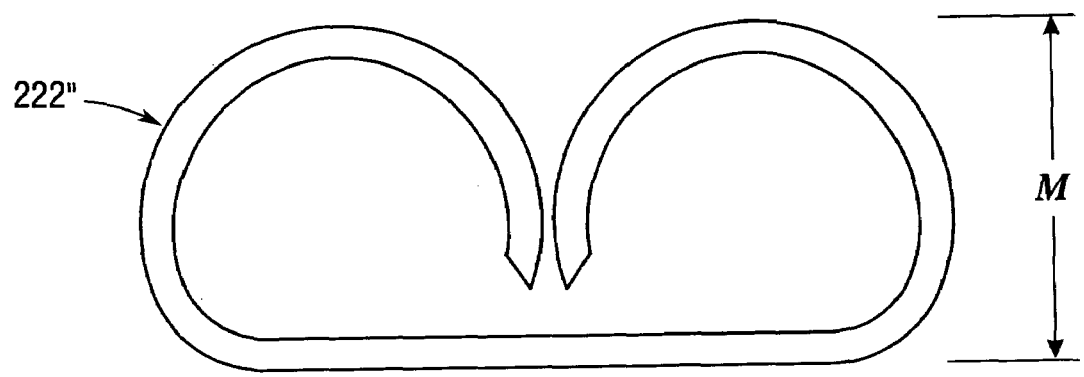
FIG. 31 depicts another staple formed by one outside driver embodiment of the present invention.
Figure 30:
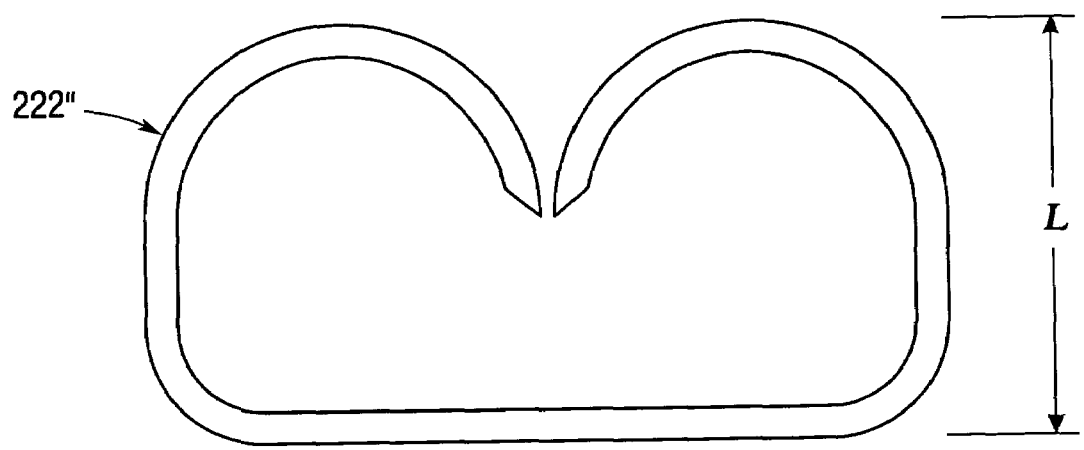
FIG. 30 depicts a staple formed by one inside driver embodiment of the present invention.

FIG. 29 illustrates the rows of staples formed on each side of a cut line 600 utilizing this embodiment of the present invention wherein the forming distances "A" and "B" are equal to each other and the forming distance "C" is greater than the forming distances "A" and "B". For example, if forming distance "C" is 0.020" greater than forming distances "A" and "B", the formed height of the outside staples 222' (represented as dimension "L" in FIG. 30) in rows 520 and 530 would be 0.020 inches is greater than the formed height of the inside staples 222" (represented as dimension "M" in FIG. 31) in rows 522. 524, 526, 528.

The same result may be achieved by utilizing another embodiment of the present invention wherein the forming distances "A", "B" and "C" are essentially equal. In this embodiment, however, the height of each of the inside sled cams 410 (distance "H" in FIG. 21) is greater than the height of each of the outside sled cams 420 (distance "J" in FIG. 22).

Thus, because the height "H" of the inside sled cams 410 is greater than the height "J" of the outside sled cams 420, the inside sled cams 410 will drive the corresponding inside drivers 330a, 330b further towards the anvil than the outside sled cams 420 will drive the corresponding outside drivers 370a, 370b. Such driving action will cause the staples supported by the inside drivers 330a, 330b to be compressed to a greater extent than those staples supported by the outside drivers 370a, 370b. For example, if distance "H" is 0.020 inches greater than distance "J", the formed height of staples 222' in lines 520, 530 would be 0.020" greater than the formed height of staples 222" in lines 522, 524, 526, 528.

Figure 32:
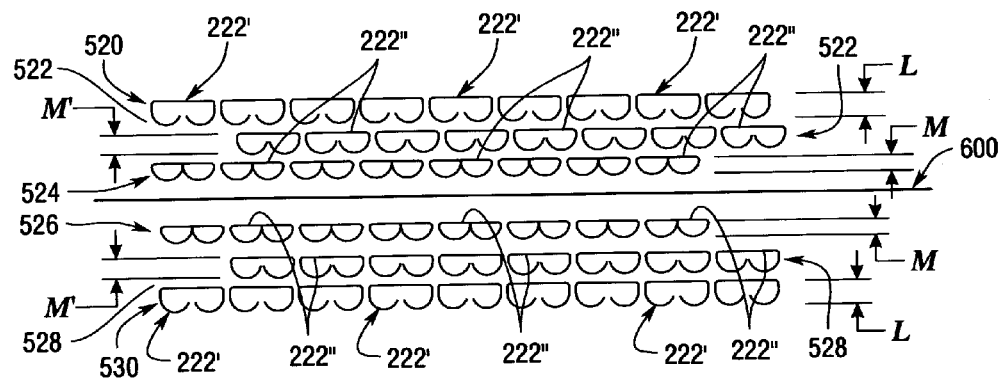
FIG. 32 is a diagrammatic representation of lines of staples installed on each side of a cut line using a surgical stapling and severing instrument of another embodiment of the present invention.

When employing yet another embodiment of the present invention, the outside rows 520, 530 of staples 222' and the inside rows 522, 528 of staples 222" may be formed with heights that are greater than the formed heights of the staples 222" in the inside rows 524, 526. See FIG. 32. This result is achieved by making the forming distances "C" greater than the forming distance "A" and making forming distance "A" greater than secondary forming distance "B".

Figure 33:
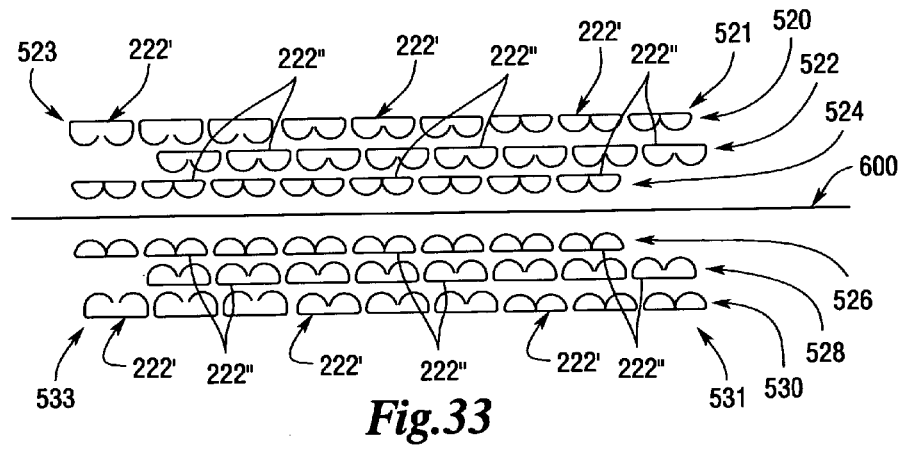
FIG. 33 is a diagrammatic representation of lines of staples installed on each side of a cut line using a surgical stapling and severing instrument of another embodiment of the present invention.
Figure 34:
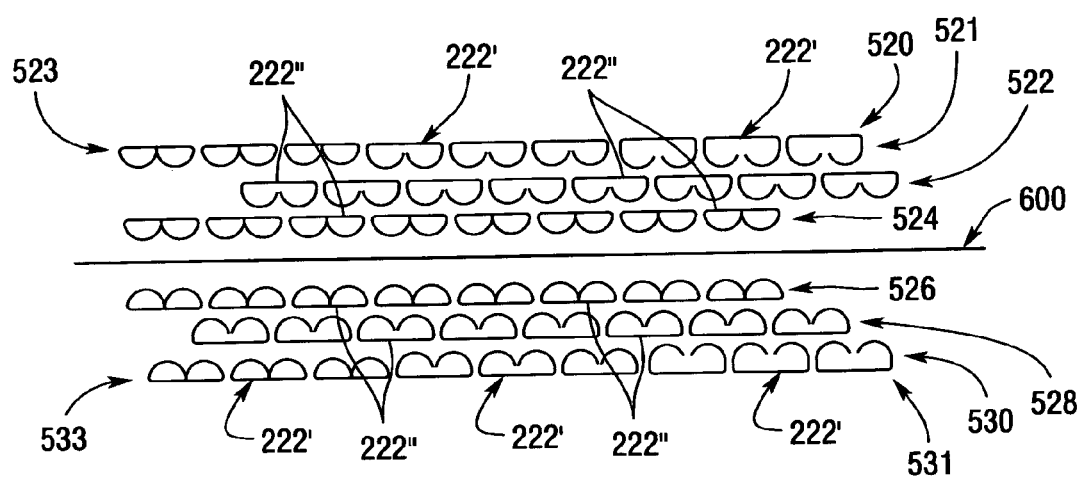
FIG. 34 is a diagrammatic representation of lines of staples installed on each side of a cut line using a surgical stapling and severing instrument of another embodiment of the present invention.

Another embodiment of the present invention can be used to install staples where it is desirable for the formed heights of staples in a single row to vary. One such arrangement is depicted in FIG. 33. As can be seen in FIG. 33, the formed heights of the staples 222' in the outside rows 520, 530 increase when moving from the proximal ends 521, 531 of each row 520, 530, respectively to the distal ends 523, 533 of each row 520, 530, respectively. This effect may be accomplished by decreasing the forming distance "C" for each succeeding driver 370a, 370b. That is, the driver 370a closest the proximal end of the cartridge 300 would be sized to establish a forming distance "C" that is greater than the forming distance "C" achieved by the adjacent driver 370a and so on to achieve a condition wherein each succeeding staple 222' (moving in the direction from the proximal end to the distal end of the cartridge 300) would have larger formed heights. This result could also be attained in the staples 222" in rows 522, 524, 526, 528 by similarly altering the forming distances "A" and/or "B" attained by each driver 330a, 330b. Likewise, formed heights of the staples 222' in the outside rows 520, 530 could be made to decrease when moving from the proximal ends 521, 531 of each row 520, 530, respectively, to the distal ends 523, 533 of each row 520, 530, respectively. This result may be attained by increasing the forming distance of each succeeding driver 370a, 370b. That is, the driver 370a closest the proximal end of the cartridge 300 would have a forming distance "C" that is less than the forming distance "C" of the adjacent driver 370a and so on to achieve a condition wherein each succeeding staple 222' (moving in the direction from the proximal end to the distal end of the cartridge) would have smaller formed heights. See FIG. 34.

Figure 35:
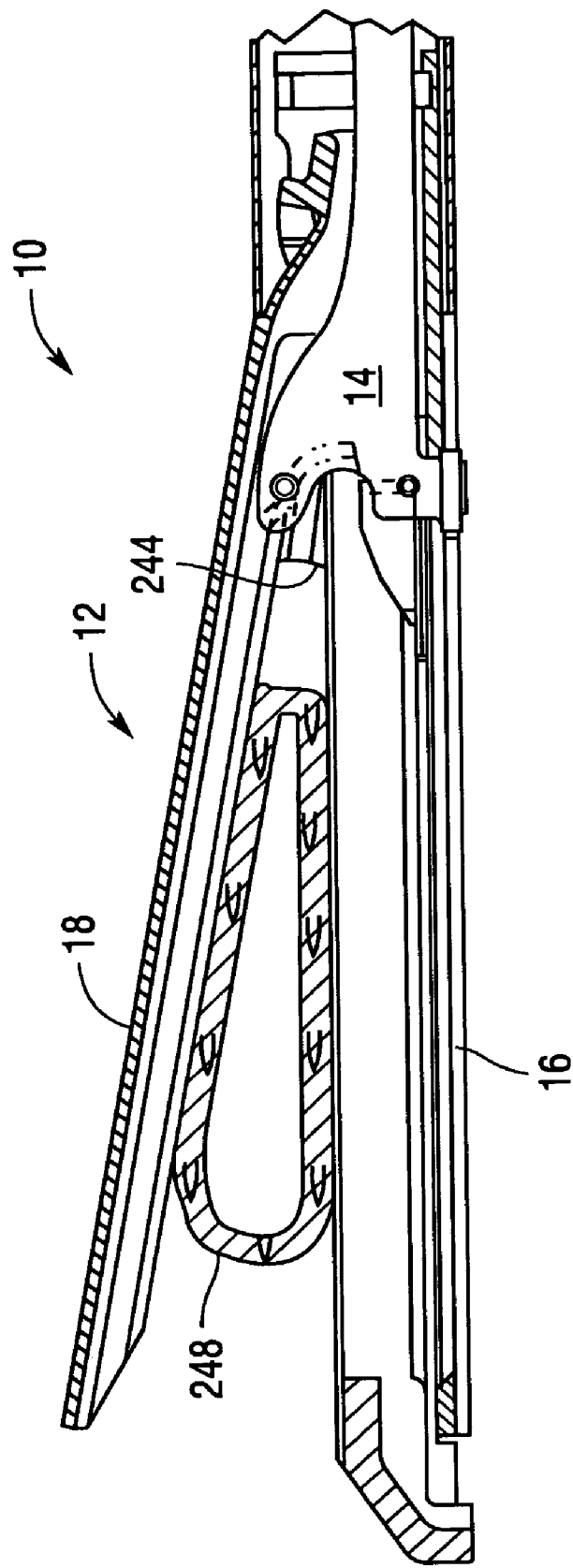
FIG. 35 is a side elevation section view of the surgical stapling and severing instrument of FIG. 1 taken along the longitudinal centerline of the end effector in a partially closed but unclamped position gripping tissue.

In use, the surgical stapling and severing instrument 10 is used as depicted in FIGS. 1-2 and 35-41. In FIGS. 1-2, the instrument 10 is in its start position, having had an unfired, fully loaded staple cartridge 300 snap-fitted into the distal end of the elongate channel 16. Both triggers 26, 28 are forward and the end effector 12 is open, such as would be typical after inserting the end effector 12 through a trocar or other opening into a body cavity. The instrument 10 is then manipulated by the clinician such that tissue 248 to be stapled and severed is positioned between the staple cartridge 300 and the anvil 18, as depicted in FIG. 35.

Figure 36:
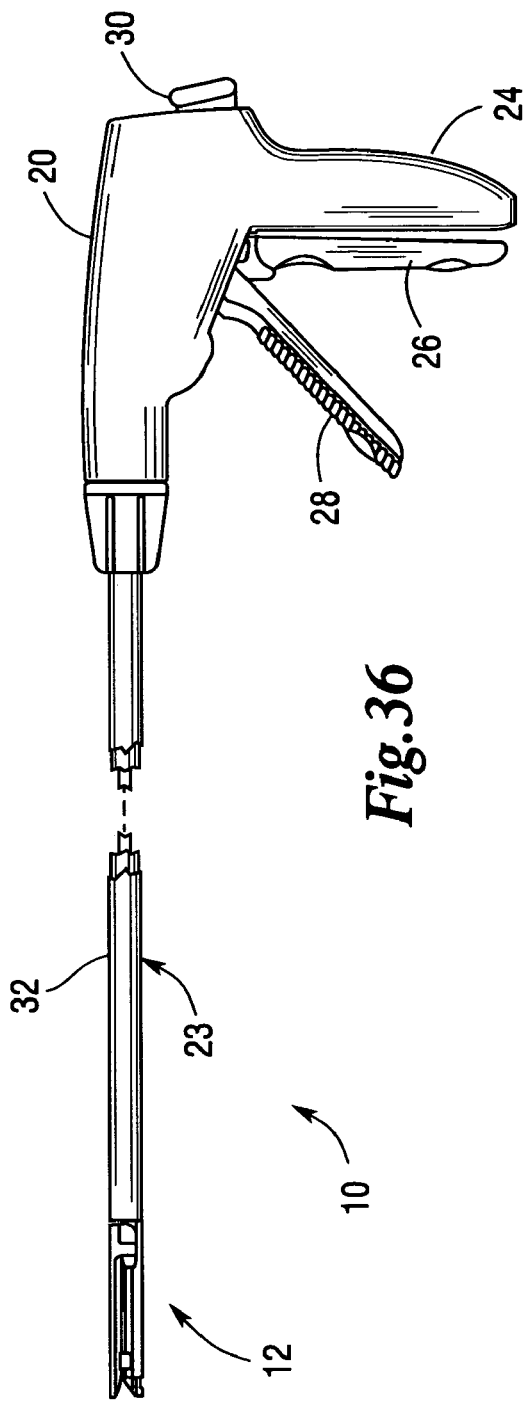
FIG. 36 depicts a partially cut away side elevational view of the surgical stapling and severing instrument of FIG. 1 in the closed or clamped position.
Figure 37:
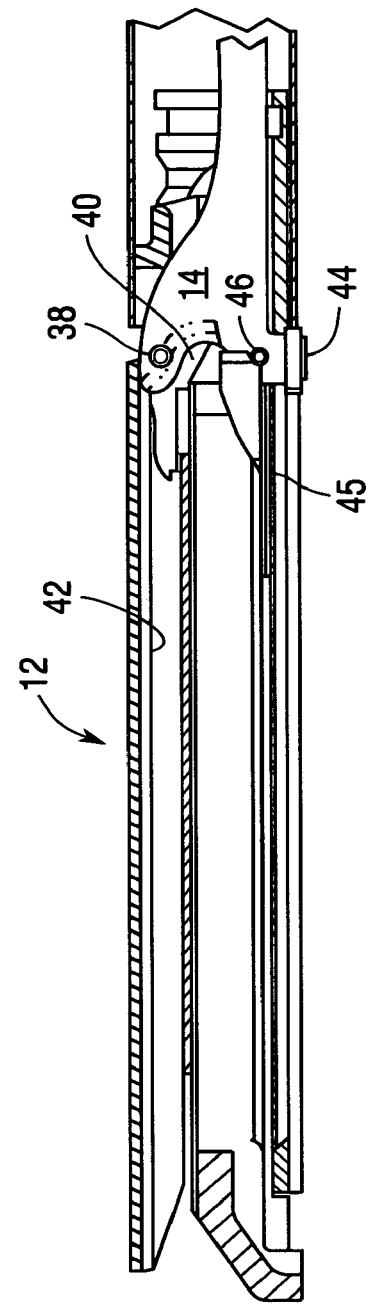
FIG. 37 depicts a side elevation view of the surgical stapling and severing instrument of FIG. 1 in the closed or clamped position with tissue properly compressed.

With reference to FIGS. 36 and 37, the clinician then moves the closure trigger 26 proximally until positioned directly adjacent to the pistol grip 24, locking the handle portion 20 into the closed and clamped position. The retracted firing bar 14 in the end effector 12 does not impede the selective opening and closing of the end effector 12, but rather resides within the anvil pocket 40. With the anvil 18 closed and clamped, the E-beam firing bar 14 is aligned for firing through the end effector 12. In particular, the upper pin 38 is aligned with the anvil slot 42 and the elongate channel 16 is affirmatively engaged about the channel slot 45 by the middle pin 46 and the firing bar cap 44.

With reference to FIGS. 38 and 39, after tissue clamping has occurred, the clinician moves the firing trigger 28 proximally causing the firing bar 14 to move distally into the end effector 12. In particular, the middle pin 46 enters the staple cartridge 300 through the firing drive slot 47 to effect the firing of the staples 222 (not shown in FIGS. 38 and 39) via wedge sled 400 toward the anvil 18. The lowermost pin, or firing bar cap 44, cooperates with the middle pin 46 to slidingly position cutting edge 48 of the firing bar 14 to sever tissue. The two pins 44, 46 also position the upper pin 38 of the firing bar 14 within longitudinal anvil slot 42 of the anvil 18, affirmatively maintaining the spacing between the anvil 18 and the elongate channel 16 throughout its distal firing movement.

Figure 40:
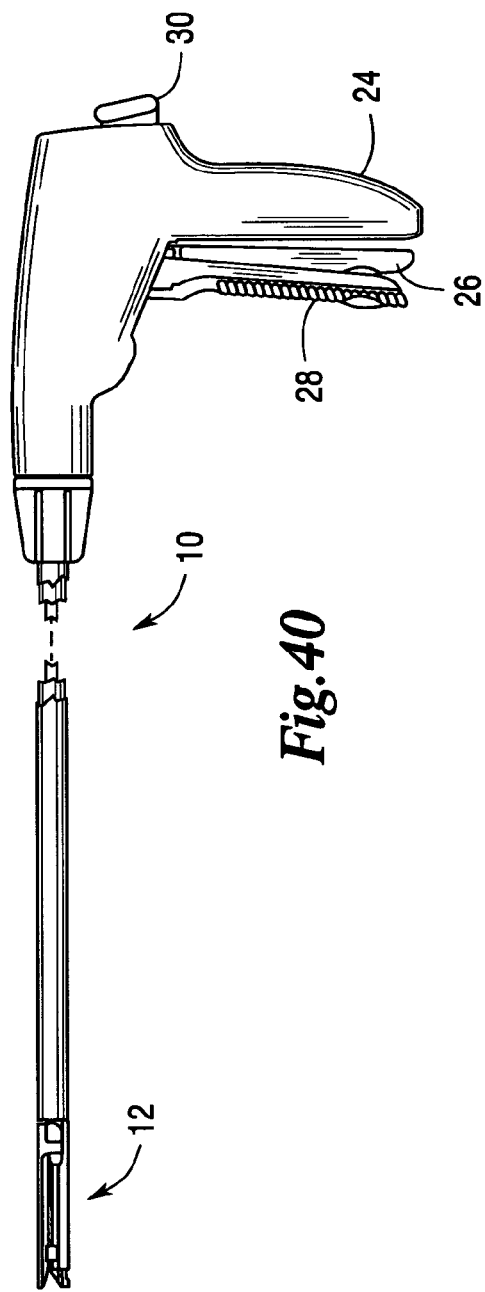
FIG. 40 depicts a view in centerline section of the distal end of the surgical stapling and severing instrument of FIG. 1 in a fully fired position.
Figure 41:
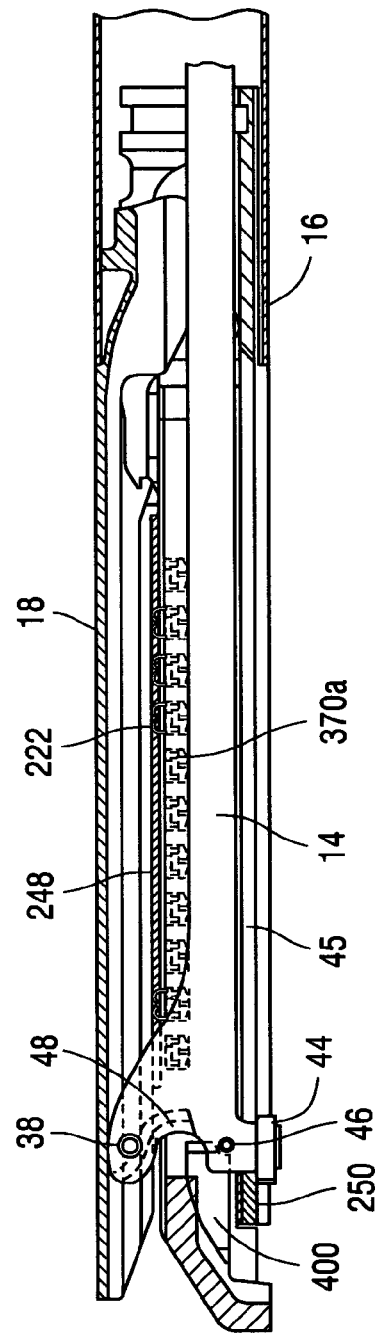
FIG. 41 is a partially cut-away side elevational view of the surgical stapling and severing instrument of FIG. 1 in a full fired position.

With reference to FIGS. 40 and 41, the clinician continues moving the firing trigger 28 until brought proximal to the closure trigger 26 and pistol grip 24. Thereby, all of the ends of the staples 222 are bent over as a result of their engagement with the anvil 18. The firing bar cap 44 is arrested against a firing bar stop 250 projecting toward the distal end of the channel slot 45. The cutting edge 48 has traversed completely through the tissue. The process is complete by releasing the firing trigger 28 and by then depressing the release button 30 while simultaneously squeezing the closure trigger 26 to open the end effector 12.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art. The various embodiments of the present invention represent vast improvements over prior staple methods that require the use of different sizes of staples in a single cartridge to achieve staples that have differing formed (final) heights.

Accordingly, the present invention has been discussed in terms of endoscopic procedures and apparatus. However, use herein of terms such as "endoscopic" should not be construed to limit the present invention to a surgical stapling and severing instrument for use only in conjunction with an endoscopic tube (i.e., trocar). On the contrary, it is believed that the present invention may find use in any procedure where access is limited to a small incision, including but not limited to laparoscopic procedures, as well as open procedures. Moreover, the unique and novel aspects of the various staple cartridge embodiments of the present invention may find utility when used in connection with other forms of stapling apparatuses without departing from the spirit and scope of the present invention.

What is claimed is:

1. A staple cartridge for use with a stapling device that has an actuator and cutting portion and an anvil that is selectively movable between open and closed positions for forming a plurality of like-sized staples, said staple cartridge comprising:

a cartridge body supportable within the stapling device for selective confronting relationship with the anvil when the anvil is in a closed position, said cartridge body configured to operably receive the actuator and cutting portion therein to enable said actuator and cutting portion to be longitudinally advanced through said cartridge from a proximal end to a distal end;

a plurality of first staple drivers movably supported within said cartridge body and being sequentially movable from an unactuated position to an actuated position upon sequential interaction with the actuator, each said first staple driver defining a first staple support cradle therein for supporting a staple thereon, each said first staple support cradle located a first staple forming distance from a corresponding portion of the closed anvil; and a plurality of second staple drivers movably supported within said cartridge body and being laterally spaced from said first staple driver, said at least one second staple driver being sequentially movable from another unactuated position to another actuated position upon sequential interaction with the actuator, each said second staple driver defining a second staple support cradle therein for supporting another staple thereon that, when unformed, is substantially similar in size to said staple supported on said first staple support cradle, each said second staple support cradle located a second staple forming distance from another portion of the closed anvil that corresponds to the second staple support cradle and wherein said second staple forming distance differs in magnitude from said first staple forming distance.

2. The staple cartridge of claim 1 wherein each said first staple driver supports at least two of said staples thereon.

3. The staple cartridge of claim 2 wherein said first staple support cradle is in a primary driver portion of said first staple driver and wherein each said first staple driver further comprises a secondary driver portion attached to said primary driver portion and defining a secondary staple support cradle located a secondary staple forming distance from another corresponding portion of the anvil when the anvil is in a closed position, said secondary support cradle supporting another one of said staples thereon.

4. The staple cartridge of claim 3 wherein said secondary staple forming distance is substantially equal to said first staple forming distance.

5. The staple cartridge of claim 3 wherein said secondary staple forming distance differs in magnitude from said first staple forming distance and said second staple forming distance.

6. The staple cartridge of claim 1 wherein said at least one first staple driver comprises a plurality of first staple drivers axially aligned in a first row of first staple drivers and wherein said at least one said second staple driver comprises a plurality of second staple drivers aligned in a second row of said second staple drivers.

7. The staple cartridge of claim 6 wherein said first staple forming distance of one said first staple drivers in said first row of said first staple drivers differs in magnitude from said first staple forming distance of another one of said first staple drivers in said first row of first staple drivers.

8. The staple cartridge of claim 7 wherein said second staple forming distance of one of said second staple drivers in said second row of said second staple drivers differs in magnitude from said second staple forming distance of another one of said second staple drivers in said second row of said second staple drivers.

9. A staple cartridge for use with a surgical instrument having an end effector that has an anvil portion pivotally attached thereto for travel between open and closed positions and further including a firing bar that is selectively reciprocatable therein for forming a plurality of like-sized unformed staples, said staple cartridge comprising:

a cartridge body sized to be supported within the end effector, said cartridge body having a longitudinally extending slot therein for reciprocatingly receiving the firing bar therein;

a first plurality of inside staple drivers axially aligned in a first row of inside staple drivers in a portion of said cartridge body adjacent a first side of said longitudinally extending slot and a second plurality of inside staple drivers axially aligned in a second row of inside staple drivers in another portion of said cartridge body adjacent a second side of said longitudinally extending slot, said inside staple drivers movably supported within said cartridge body for selective movement toward the anvil when the anvil is in a closed position, each said inside staple driver defining a first staple support cradle for supporting a staple thereon, each said first staple support cradle located a first staple forming distance from a corresponding portion of the anvil when the anvil is in a closed position;

a first plurality of outside staple drivers axially aligned in a first row of outside staple drivers adjacent to said first row of said inside staple drivers and a second plurality of outside staple drivers axially aligned in a second row of outside staple drivers and adjacent to said second row of inside staple drivers, each of said outside staple drivers movably supported within said cartridge body for selective driving movement toward the anvil when the anvil is in the closed position, each of said outside staple drivers defining a second staple support cradle for supporting another staple thereon that, when unformed, is substantially similar in size to said staple supported on said first staple support cradle, each said second staple support cradle located a second staple forming distance from another corresponding portion of the anvil when the anvil is in the closed position, said second staple forming distance differing in magnitude from said first staple forming distance; and a wedge sled supported within said cartridge body for driving contact by the firing bar and actuating contact with said first and second pluralities of said inside staple drivers and said first and second pluralities of said outside staple drivers such that, as said firing bar moves within said elongated slot in said cartridge body in a first axial direction, said wedge sled drives each of said inside and outside drivers towards the anvil to bring the staples supported thereon into forming contact with the anvil when the anvil is in the closed position.

10. The staple cartridge of claim 9 wherein each of said inside staple drivers support two of said staples thereon.

11. The staple cartridge of claim 10 wherein said two staples supported on at least one of said inside staple drivers are longitudinally offset from each other.

12. The staple cartridge of claim 10 wherein said first staple support cradle is in a primary driver portion of said inside driver and wherein each said inside driver further comprises a secondary driver portion attached to said primary driver portion, said secondary driver portion defining a secondary staple support cradle therein that is located a secondary staple forming distance from another corresponding portion of the anvil when the anvil is in the closed position, each said secondary staple support cradle supporting one of said staples thereon.

13. The staple cartridge of claim 12 wherein said secondary staple forming distance is substantially equal to said first staple forming distance.

14. The staple cartridge of claim 12 wherein said secondary staple forming distance differs in magnitude from said first staple forming distance and said second staple forming distance.

15. The staple cartridge of claim 9 wherein said second staple forming distance of at least one of said outside staple drivers in said first row of said first outside staple drivers differs in magnitude from said second staple forming distance of at least one other said outside staple driver in said first row of said outside staple drivers.

16. The staple cartridge of claim 15 wherein said second staple forming distance of at least one of said outside staple drivers in said second row of said outside staple drivers differs in magnitude from said second staple forming distance of at least one other said outside staple driver in said second row of said outside staple drivers.

17. The staple cartridge of claim 15 wherein said first staple forming distance of at least one of said inside staple drivers in said second row of said inside staple drivers differs in magnitude from said first staple forming-distance of at least one other said inside staple driver in said second row of said inside staple drivers.

18. The staple cartridge of claim 9 wherein said first staple forming distance of at least one of said first staple drivers in said first row of said inside staple drivers differs in magnitude from said first staple forming distance of at least one other said inside staple driver in said first row of said inside staple drivers.

19. A staple cartridge for use with a surgical instrument having an end effector that has an anvil portion pivotally attached thereto for travel between open and closed positions and further including a firing bar that is selectively axially reciprocatable therein, said staple cartridge comprising:
a cartridge body sized to be supported within the end effector, said cartridge body having a longitudinally extending slot therein for reciprocatingly receiving the firing bar therein;
a plurality of first inside staple drivers axially aligned in a first row of first inside staple drivers on a first side of said longitudinally extending slot, each of said first inside staple drivers movably supported within said cartridge body for selective movement toward the anvil when the anvil is in a closed position and supporting at least one staple thereon;
a plurality of first outside staple drivers aligned in a first row of first outside staple drivers on said first side of said longitudinally extending slot and adjacent to said first row of said first inside staple drivers, each of said first outside staple drivers movably supported within said cartridge body for selective driving movement toward the anvil when the anvil is in the closed position and supporting another one of said staples thereon; and
a wedge sled supported within said cartridge body for contact with said firing bar, said wedge sled comprising:
a first inside sled cam having a first maximum sled cam height measured from a bottom-most drive surface of said first inside cam to an upper-most portion of said first inside cam, said first inside sled cam oriented for sequential sliding actuating contact with said first inside staple drivers in said first row of said first inside staple drivers when said firing bar is axially advanced through said elongated slot in a first axial direction such that said first inside staple drivers are driven towards the anvil a first distance equal to said first maximum sled cam height; and
a first outside sled cam having a second maximum sled cam height measured from a bottom-most drive surface of said first outside cam to an upper-most portion of said first outside cam, said second maximum sled cam height differing in magnitude from said first maximum sled cam height, said first outside sled cam oriented for sequential sliding actuating contact with said first outside staple drivers in said first row of said first outside staple drivers when said firing bar is advanced through said elongated slot in the first direction such that said first outside staple drivers are driven towards the anvil a second distance equal to said second maximum sled cam height.

20. The staple cartridge of claim 19 further comprising:
a plurality of second inside staple drivers aligned in a second row of second inside staple drivers on a second side of said longitudinally extending slot, each of said second inside staple drivers movably supported with said cartridge body for selective driving movement towards the anvil when the anvil is in the closed position and supporting another one of said staples thereon;
a plurality of second outside staple drivers aligned in a second row of second outside staple drivers on said second side of said longitudinally extending slot and adjacent to said second row of said second inside staple drivers, each of said second outside staple drivers movably supported within said cartridge body for driving movement towards the anvil when the anvil is in the closed position and supporting another one of said staples thereon and wherein said wedge sled further comprises:
a second inside sled cam having a primary maximum sled cam height measured from a bottom-most drive surface of said second inside sled cam to an upper-most portion of said second inside sled cam, said second inside sled cam oriented for sequential sliding actuating contact with said second inside staple drivers in said second row of said second inside staple drivers when said firing bar is axially advanced through said elongated slot in the first direction such that said second inside staple drivers are driven towards the anvil a primary distance equal to said primary maximum sled cam height; and
a second outside sled cam having a secondary maximum sled cam height measured from a bottom-most drive surface of said second outside sled cam to an upper-most portion of said second outside sled cam, said second outside sled cam oriented for sequential sliding actuating contact with said second outside staple drivers in said second row of said second outside staple drivers when said firing bar is axially advanced through said elongated slot in the first direction such that said second outside staple drivers are driven towards the anvil a secondary distance equal to said secondary maximum sled cam height.

21. The staple cartridge of claim 20 wherein said primary maximum sled cam height is substantially equal to said first maximum sled cam height and wherein said secondary maximum sled cam height is substantially equal to said second maximum sled cam height.

22. The staple cartridge of claim 20 wherein said primary maximum sled cam height is not equal to said first, second, or secondary maximum sled cam heights.

23. A staple cartridge for use with a stapling device that has an actuator and cutting member that is selectively actuatable in an axial direction and an anvil portion that is selectively movable between open and closed positions, said staple cartridge comprising:

a cartridge body supportable within the stapling device for selective confronting relationship with the anvil portion thereof when in a closed position, said cartridge body configured to axially receive the actuator and cutting member therein;

a plurality of first staple drivers movably supported within said cartridge body for sequential contact by the actuator such that, as the actuator is axially advanced through said cartridge body, said first staple drivers are sequentially driven in a direction toward the anvil when the anvil is in the closed position, each said first staple driver defining a first staple support cradle therein for supporting a staple thereon, said first staple support cradle located a first staple forming distance from a corresponding portion of the closed anvil;

a plurality of second staple drivers movably supported within said cartridge body for sequential contact by the actuator such that as the actuator is axially advanced through said cartridge body, said second staple drivers are sequentially driven in said direction toward the closed anvil, each said second staple driver defining a second staple support cradle therein for supporting another staple thereon, said second staple support cradle located a second staple forming distance from another portion of the closed anvil that corresponds to the second staple support cradle and wherein said second staple forming distance differs from said first staple forming distance;

a plurality of third staple drivers movably supported within said cartridge body and being sequentially movable from a third unactuated position to a third actuated position upon sequential interaction with the actuator, each said third staple driver defining a third staple support cradle therein that is located a third maximum staple forming distance from another portion of the closed anvil that corresponds to the third staple support cradle when the closed anvil is substantially parallel to said top cartridge surface, and wherein said first maximum staple forming distance differs from at least one of said second and third maximum staple forming distances;

a first staple disposed in at least one of said first staple support cradles;

a second staple disposed in at least one of said second staple support cradles; and a third staple in each of said third staple in at least one of said third staple support cradles, said first, second, and third staples having substantially the same unformed size.

* * * * *